US012523661B2

(12) United States Patent
Gunawardena

(10) Patent No.: US 12,523,661 B2
(45) Date of Patent: Jan. 13, 2026

(54) MATERIALS AND METHODS FOR DIFFERENTIAL CHARACTERIZATION OF MOLECULAR CONJUGATES AND CONJUGATION

(71) Applicant: JANSSEN BIOTECH, INC., Horsham, PA (US)

(72) Inventor: Harsha Gunawardena, Lafayette Hill, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 889 days.

(21) Appl. No.: 17/761,432

(22) PCT Filed: Sep. 19, 2020

(86) PCT No.: PCT/US2020/051686
§ 371 (c)(1),
(2) Date: Mar. 17, 2022

(87) PCT Pub. No.: WO2021/055894
PCT Pub. Date: Mar. 25, 2021

(65) Prior Publication Data

US 2022/0373558 A1 Nov. 24, 2022

Related U.S. Application Data

(60) Provisional application No. 62/902,958, filed on Sep. 19, 2019.

(51) Int. Cl.
*G01N 33/68* (2006.01)
*C07K 1/13* (2006.01)

(52) U.S. Cl.
CPC .......... *G01N 33/6848* (2013.01); *C07K 1/13* (2013.01); *G01N 2458/15* (2013.01)

(58) Field of Classification Search
None
See application file for complete search history.

(56) References Cited

U.S. PATENT DOCUMENTS

| | | | |
|---|---|---|---|
| 2013/0309689 A1 | 11/2013 | Rogers et al. | |
| 2016/0356786 A1 | 12/2016 | Li et al. | |

(Continued)

FOREIGN PATENT DOCUMENTS

| | | |
|---|---|---|
| CN | 109477819 | 3/2019 |
| JP | 2017526682 A | 9/2017 |

(Continued)

OTHER PUBLICATIONS

Thermo Fisher, Achieving robust, accurate TMT quantitation efficiency with Tribrid technology, The Analytical Scientist, Proteomics, Mass Spectrometry, Retrieved from internet, https://theanalyticalscientist.com/app-notes/achieving-robust-accurate-tmt-quantitation-efficiency-with-tribrid-technology (Year: 2017).*

(Continued)

*Primary Examiner* — Xiaoyun R Xu
(74) *Attorney, Agent, or Firm* — Riverside Law LLP

(57) ABSTRACT

Methods of analyzing a drug polypeptide conjugate using tandem mass spectrometry involving dual tandem mass tags (TMTs) are described. Provided herein is an integrated method using TMTs to obtain three analytical measurements, termed "triple play", which enables identification of the drug occupancy, normalization between multiple samples and triggering of additional MS/MS to identify and localize conjugation site(s) of the payload. Also described is a method of multiplexing conjugation reactions in a single run with TMT labeling for enhanced throughput capability, while maintaining the same sensitivity with current mass spectrometry instrumentation.

19 Claims, 52 Drawing Sheets

(56) References Cited

U.S. PATENT DOCUMENTS

2018/0299464 A1 10/2018 Li et al.
2019/0041394 A1 2/2019 Chen et al.

FOREIGN PATENT DOCUMENTS

JP 2018536175 A 12/2018
JP 2018538511 A 12/2018

OTHER PUBLICATIONS

Bachor et al., 2019, "Trends in the Design of New Isobaric Labeling Reagents for Quantitative Proteomics," Molecules, 24(4):701 (19 pages).

Dan et al., 2018, "Antibody-Drug Conjugates for Cancer Therapy: Chemistry to Clinical Implications," Pharmaceuticals (Basel), 11(2):32 (22 pages).

Friese et al., 2018, "Practical approaches for overcoming challenges in heightened characterization of antibody-drug conjugates with new methodologies and ultrahigh-resolution mass spectrometry," MAbs, 10(3):335-345.

Hill et al., 2018, "An accurate TMT-based approach to quantify and model lysine susceptibility to conjugation via N-hydroxysuccinimide esters in a monoclonal antibody," Sci. Rep., 8(1):17680 (14 pages).

Huggins et al., 2019, "Site Selective Antibody-Oligonucleotide Conjugation via Microbial Transglutaminase," Molecules, 24(18):3287 (13 pages).

International Searching Authority, International Search Report and Written Opinion for International Patent Application No. PCT/US2020/051686 (Pub No. WO 2021055894) mailed Feb. 10, 2021 (11 pages).

Janin-Bussat et al., 2015, "Characterization of antibody drug conjugate positional isomers at cysteine residues by peptide mapping LC-MS analysis," J. Chromatogr. B. Analyt. Technol. Biomed. Life Sci., 981-982:9-13 (Epub 2014).

Le et al., 2012, "Profiling antibody drug conjugate positional isomers: a system-of-equations approach," Anal. Chem., 84(17):7479-7486.

Lim et al., 2017, "Improved Method for Determining Absolute Phosphorylation Stoichiometry Using Bayesian Statistics and Isobaric Labeling," J. Proteome. Res., 16(11):4217-4226.

Liu et al., 2012, "Disulfide bond structures of IgG molecules: structural variations, chemical modifications and possible impacts to stability and biological function," MAbs, 4(1):17-23.

Mcalister et al., 2014, "MultiNotch MS3 enables accurate, sensitive, and multiplexed detection of differential expression across cancer cell line proteomes," Anal. Chem., 86(14):7150-7158.

Mcpherson et al., 2020, "Pushing the Envelope: Advancement of ADCs Outside of Oncology," Methods Mol. Biol., 2078:23-36.

Nagy et al., 2020, "Rapid and Simultaneous Characterization of Drug Conjugation in Heavy and Light Chains of a Monoclonal Antibody Revealed by High-Resolution Ion Mobility Separations in SLIM," Anal. Chem., 92(7):5004-5012.

Polakis, 2016, "Antibody Drug Conjugates for Cancer Therapy," Pharmacol. Rev., 68(1):3-19.

Savitski et al., 2013, "Measuring and managing ratio compression for accurate iTRAQ/TMT quantification," J. Proteome. Res., 12(8):3586-3598.

Wu et al., 2011, "A large-scale method to measure absolute protein phosphorylation stoichiometries," Nat. Methods, 8(8):677-683.

* cited by examiner

General Chemical Structure

TMT10plex reagent

TMT16plex reagent

Fig. 4

| mAb or Peptides | Drug or Mimic | Chemical Structure | Conjugation Chemistry | Drug Load |
|---|---|---|---|---|
| NIST | IAA | 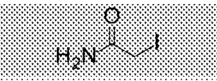 | Alkylation @ Cysteine | Different ratios |
| NIST or HSA peptide | Biotin PEO Iodo Acetamide | 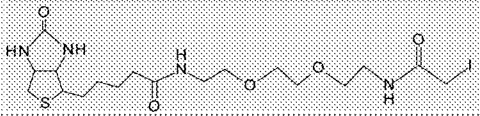 | Alkylation @ Cysteine | Different ratios |
| NIST or HSA peptide | IAA, DACM-3 | 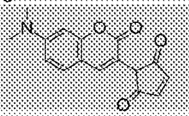 | Maleimide @ Cysteine | Different ratios |
| Sigma mAb (MSQC4) | Dansyl Fluorophore | 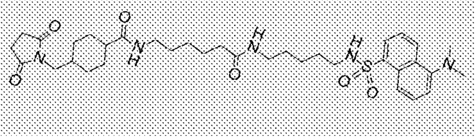 | Maleimide @ Cysteine | Standard (MSQC8) Avg. DAR of 4 |

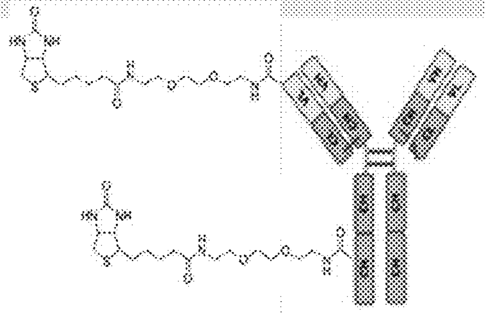

NIST mAb-Biotin PEO Acetamide

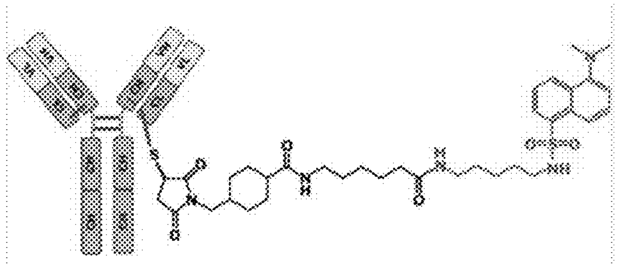

Sigma MSQC4 conjugated to dansyl fluorophore (MSQC8)

$$\%\,ADC\ Occupancy = \frac{A2 - A1}{A2} \times 100$$

$$\%\,ADC\ Occupancy = \frac{B2 - B1}{B2} \times 100$$

Transfer of precursor ions from Ion Routing Multipole (IRM) to Ion trap ( IT)

Fig. 20B

| Sample (Replicate) | Peak # | Ratio | % Occupancy | % Normalized Occupancy |
|---|---|---|---|---|
| MSQC8 (1) | 1 | --- | 75 | 56 |
| MSQC4:MSQC8 (1) | 2 | 2 | 55 | 33 |
| MSQC4:MSQC8 (2) | 3 | 2 | 90 | 31 |
| MSQC8 (2) | 4 | --- | 25 | 64 |

MATERIALS AND METHODS FOR DIFFERENTIAL CHARACTERIZATION OF MOLECULAR CONJUGATES AND CONJUGATION

The present application is a U.S. National Stage Application under 35 U.S.C. § 371 of International Patent Application No. PCT/US2020/051686, filed Sep. 19, 2020, which claims the benefit of U.S. Provisional Application No. 62/902,958, filed on Sep. 19, 2019, the disclosure of each of which is incorporated by reference herein in its entirety.

FIELD OF THE INVENTION

The application relates to methods and reagents for, inter alia, characterizing molecular conjugates, including, for example quantifying, normalizing, detecting and/or identifying conjugated molecules. As taught in the application, the present invention is useful for use with various types of molecules, including, for example, molecular conjugates, drug conjugates, such as antibody-drug conjugates (ADCs), and the like.

BACKGROUND OF THE INVENTION

Conjugation of molecules can be advantageous. For example, drug conjugates, such as antibody-drug conjugates (ADCs), are a growing class of therapies for treating cancers (Polakis, *Pharmacological reviews* 68, 3-19 (2016)) and immunological disorders (McPherson. *Methods in molecular biology* 2078, 23-36 (2020)). A general structure of an ADC contains a monoclonal antibody (mAb) connected to a drug via a cleavable or a non-cleavable linker. For example, the ADC can have a humanized/human mAb connected to biologically active payloads, such as cytotoxics, steroids and anti-sense oligonucleotides, via a non-cleavable or cleavable linker, such as an acid labile linker, protease cleavable linker, or disulfide linker. The linker can be covalently linked to the mAb at a conjugation site via lysine coupling, cysteine alkylation or an enzymatic reaction. The ADC binds to its target cell-surface antigen receptor, which enables targeted delivery of the drug to a target site and minimizes systemic toxicity effects to healthy tissue, resulting in increased selectivity, improved efficacy and safety over alternative chemotherapeutic methods or other first generation mAbs (see, e.g., Dan et al., 2018, *Pharmaceuticals* (*Basel*) 11).

Perfected conjugation is difficult to achieve. Incomplete conjugation processes can result in free or non-conjugated drug, drug-linker, or drug related impurities. Degradation products can occur over time in formulations as well as in vivo. Characterization and quantification of ADCs are important for the safety, efficacy, and uniformity of the ADCs.

BRIEF SUMMARY OF THE INVENTION

The present application provides improved, such as more accurate, reliable, sensitive, etc., materials and methods for efficient identification and quantification of molecular conjugates, including therapeutic conjugates, such as drug conjugates. The present invention teaches materials and methods for, for example, such improved characterization.

The present application relates to, inter alia, a method of analyzing a conjugate comprising a drug covalently linked to a polypeptide by using Tandem Mass Tag (TMT).

In one aspect, the application relates to a method of analyzing a conjugate comprising a drug covalently linked to a polypeptide, comprising:

(i) contacting a sample comprising the conjugate with a first tandem mass tag (TMT) to thereby label the polypeptide of the conjugate with the first TMT;

(ii) digesting the polypeptide of the conjugate labeled with the first TMT to generate a first mixture comprising one or more unlabeled peptides and one or more peptides labeled with the first TMT;

(iii) contacting the first mixture with a second tandem mass tag (TMT) to thereby obtain a second mixture comprising one or more peptides labeled with at least one of the first TMT and the second TMT, optionally one or more unlabeled peptides, wherein the first TMT and the second TMT do not have the same reporter ion mass;

(iv) subjecting the second mixture to a liquid chromatography (LC) to generate elutes of the LC; and (v) subjecting the elutes to a tandem mass spectrometry to obtain a mass spectrum of a peptide comprising at least one reporter ion of the first TMT and the second TMT; and (vi) detecting the mass-to-charge ratio (m/z) associated with the at least one reporter ion to thereby analyze the conjugate in the sample.

In another aspect, a sample comprising a conjugate of a drug covalently linked to a polypeptide is analyzed together with a control sample comprising the polypeptide not covalently linked to the drug. The method comprises:

(i) contacting a sample comprising the conjugate with a first tandem mass tag (TMT) to thereby label the polypeptide of the conjugate with the first TMT;

(ii) digesting the polypeptide of the conjugate labeled with the first TMT to generate a first mixture comprising one or more unlabeled peptides and one or more peptides labeled with the first TMT;

(iii) contacting the first mixture with a second tandem mass tag (TMT) to thereby obtain a second mixture comprising one or more peptides labeled with at least one of the first TMT and the second TMT, optionally one or more unlabeled peptides;

(iv) contacting a control sample comprising the polypeptide not covalently linked to the drug with a third TMT to thereby label the polypeptide not covalently linked to the drug with the third TMT;

(v) digesting the polypeptide not covalently linked to the drug labeled with the third TMT to generate a third mixture comprising one or more unlabeled peptides and one or more peptides labeled with the third TMT;

(vi) contacting the third mixture with a fourth tandem mass tag (TMT) to thereby obtain a fourth mixture comprising one or more peptides labeled with at least one of the third TMT and the fourth TMT, optionally one or more unlabeled peptides;

(vii) combining the second mixture with the fourth mixtures and subjecting the combination to a liquid chromatography (LC) to generate elutes of the LC; and (viii) subjecting the elutes to a tandem mass spectrometry to obtain a mass spectrum of a peptide comprising at least one reporter ion of the first TMT, the second TMT, the third TMT and the fourth TMT; and (ix) detecting the mass-to-charge ratio associated with the at least one reporter ion to thereby analyze the conjugate in the sample, wherein none of the first TMT, the second TMT, the third TMT and the fourth TMT has the same reporter ion mass, the first TMT and the third TMT are selected from a first isobaric set of TMTs, the second TMT and the fourth TMT are selected from a second isobaric set of TMTs, and the first isobaric set of TMTs are reactive to an unconjugated amino acid residue that is capable of forming a covalent bond with the drug, and the second isobaric set of TMTs are reactive to lysine or free amine at the N-terminus of a peptide.

In one aspect, a method of the application is used to determine the occupancy ratio of a site of conjugation in a conjugate. For example, the individual site occupancy of a conjugate can be determined by: 1) obtaining a mass spectrum for a peptide labeled with both of the first TMT and the second TMT and a peptide labeled with both of the third TMT and the fourth TMT using a method of the application, wherein the mass spectrum comprises a reporter ion of the first TMT, a reporter ion of the third TMT, a reporter ion of the second TMT and a reporter ion of the fourth TMT; 2) detecting the mass-to-charge ratio (m/z) associated with the reporter ions in the mass spectrum; and 3) determining the occupancy ratio of a site of conjugation in the conjugate based on the intensity of the reporter ion of the first TMT and the intensity of the reporter ion of the third TMT, or the intensity of the reporter ion of the second TMT and the intensity of the reporter ion of the fourth TMT in the mass spectrum, preferably the occupancy ratio is determined by the following equation:

(the intensity of the reporter ion of the third TMT−the intensity of the reporter ion of the first TMT)/the intensity of the reporter ion of the third TMT, or (the intensity of the reporter ion of the fourth TMT−the intensity of the reporter ion of the second TMT)/the intensity of the reporter ion of the fourth TMT.

In certain embodiments, the occupancy ratio of the site of conjugation in the conjugate is determined at various time points, wherein additional TMTs are used to label the polypeptides at different time points.

In another embodiment, a method of the application is used to normalize a conjugate sample with a control sample. For example, a conjugate sample is normalized with a control sample by a method comprising: 1) obtaining a mass spectrum for a peptide labeled with only the second TMT and a peptide labeled with only the fourth TMT using the method of claim 2, wherein the mass spectrum comprises a reporter ion of the second TMT and a reporter ion of the fourth TMT, but not a reporter ion of the first TMT or third TMT; 2) detecting the mass-to-charge ratio (m/z) associated with the reporter ions; and 3) normalizing the sample with the control sample by the ratio of the intensity of the reporter ion of the second TMT to that of the reporter ion of the fourth TMT.

In yet another embodiment, a method of the application is used to localize the drug conjugation site, e.g., the site where the drug covalently binds to the polypeptide, in a conjugate. For example, the drug conjugation site can be localized by a method comprising: 1) obtaining a mass spectrum of a peptide labeled only with the second TMT using a method of the application, wherein the mass spectrum comprises only a reporter ion of the second TMT, but not a reporter ion of the first, third or fourth TMT; and 2) triggering a second tandem mass spectrometry analysis on the peptide labeled only with the reporter ion of the second TMT to thereby localize the drug conjugation site. In certain embodiments, the peptide labeled only with the reporter ion of the second TMT, which is obtained after the digestion of the second mixture, is completely conjugated to the drug, e.g., all amino acid residues on the peptide that are capable of conjugating to the drug have been covalently linked to the drug. The peptide can be conjugated to only one drug, when the peptide contains only one amino acid residue (e.g., Cys or Lys) capable of forming a covalent bond with the drug. The peptide can also be conjugated to more than one drugs, when the peptide contains more than one amino acid residues (e.g., Cys or Lys) capable of forming a covalent bond with the drug.

In certain embodiment, a method of localizing the drug conjugation site in the conjugate, comprises: 1) obtaining a mass spectrum of a peptide labeled only with the first and the second TMTs using a method of the application, wherein the mass spectrum comprises only reporter ions of the first and the second TMTs, but not a reporter ion of the third or fourth TMT; and 2) triggering a second tandem mass spectrometry analysis on the peptide labeled only with the first and the second TMTs to thereby localize the drug conjugation site. In certain embodiments, the peptide labeled only with the first and second TMTs, which is obtained after the digestion of the second mixture, is incompletely conjugated to the drug, e.g., only some, but not all, amino acid residues capable of conjugating to the drug have been covalently linked to the drug.

In one embodiment of the application, the conjugate is a drug antibody conjugate (ADC), more preferably, the ADC comprises a drug covalently linked to one or more cysteine (Cys) or lysine (Lys) residues of a monoclonal antibody.

As a person of ordinary skill in the art would appreciate, various suitable tandem mass spectrometry can be used in a method of the application in view of the present disclosure. See, e.g., Friese et al., *MAbs* 10, 335-345 (2018), for a review of tandem mass spectrometry, the content of which is incorporated herein by reference in its entirety. In certain embodiments, a high energy collision-induced dissociation tandem mass spectrometry (HCD-MS2) is used to obtain the mass spectrum of a peptide comprising at least one reporter ion of the first TMT, the second TMT, the third TMT and the fourth TMT. In other embodiments, after one or more TMT reporter ions are detected from a peptide from the HCD-MS2 analysis, additional dissociation analysis is triggered for additional characterization of the peptide, e.g., to localize the drug conjugation site in the peptide. The additional dissociation can be conducted by a second tandem mass spectrometry analysis. Examples of second tandem mass spectrometry useful for such a method include, but are not limited to, an electron transfer dissociation tandem mass spectrometry (ETD-MS2) or an electron-capture dissociation tandem mass spectrometry (ECD-MS2).

In other embodiments, a higher trigger intensity threshold and/or a narrow isolation window is used to improve the triggering of the second tandem mass spectrometry. In certain embodiments, synchronous precursor selection with tribrid technology is applied to the tandem mass spectrometry to improve the specificity and accuracy of the detection and quantification.

Any suitable TMTs can be used in view of the disclosure in the application. See, e.g., Bachor et al., *Molecules* 2019, 24, 701, for a review of TMTs, the content of which is incorporated herein by reference in its entirety. In some embodiments of the application, the first isobaric set of TMTs comprises two or more TMTs reactive to reduced cysteine. Preferably, the first isobaric set of TMTs comprises two, three, four, five, six or more TMTs reactive to reduced cysteine. In some embodiments, the first isobaric set comprises two, three, four, five, six or more isobaric isomers (e.g., same mass and structure) that are iodoacetyl-activated for covalent, irreversible labeling of sulfhydryl (—SH) groups. In some embodiment, the first isobaric set comprises two, three, four, five or six isobaric isomers of the IodoTMTsixplex isobaric label reagent set, which is available from ThermoFisher Scientific (Catalog No. 90101).

In certain embodiments, each of the first TMT and the third TMT comprises a mass reporter, a mass normalizer and a cysteine reactive group that are covalently linked to each other. Thus, each of the first and third TMTs labels reduced cysteine in the polypeptide of the conjugate, and can be used for the analysis of a conjugate containing a drug covalently linked to one or more cysteine residues of the polypeptide. Preferably, each of the first and third TMT is selected from the isobaric set of IodoTMTsixplex.

In some embodiments of the application, the second isobaric set of TMTs comprises two, three, four, five, six or more TMTs reactive with lysine or the primary amine at the N-terminus of a peptide. In one embodiment of the application, the second isobaric set of TMTs comprises two, three, four, five, six, seven, eight, nine, ten or more isobaric compounds having an amine-reactive NHS-ester group, a spacer arm and a mass reporter. For example, the second isobaric set can comprise two, three, four, five, six or more isobaric isomers of the TMT10Plex™ (ThermoFisher, Catalog No. 90110), the TMTsixplex™ (ThermoFisher, Catalog No. 90061), or the TMTpro™ 16 plex (ThermoFisher, Catalog No. A44520) label reagent sets.

In certain embodiments, each of the second TMT and the fourth TMT comprises a mass reporter, a mass normalizer and an amine reactive group that are covalently linked to each other. Thus, each of the second and fourth TMTs labels lysine or the N-terminus of the polypeptide of the conjugate, and can be used together with the first and third TMTs for the analysis of a conjugate containing a drug covalently linked to one or more cysteine residues of the polypeptide. Preferably, each of the second TMT and the fourth TMT is selected from an isobaric set of TMT6plex, TMT10plex or TMT pro16 plex.

In some embodiments, the first isobaric set and the second isobaric set of TMTs each independently comprise two, three, four, five, six or more TMTs reactive with lysine or the primary amine at the N-terminus of a peptide. In certain embodiments, each of the first, second, third and fourth TMTs comprises a mass reporter, a mass normalizer and an amine reactive group that are covalently linked to each other. The TMTs can be used for the analysis of a conjugate containing a drug covalently linked to one or more lysine residues of the polypeptide.

In some embodiments, a multiplex of samples comprising one or more conjugates are analyzed together. In certain embodiments, the drug conjugation site in the conjugate is characterized by a mass spec bar code comprising (2n+2) reporter ions, and the conjugate is normalized by a mass spec bar code comprising n+1 reporter ions, and n is the number of samples analyzed by the method.

Other aspects of the application relate to a system for conducting any of the method of claims 1-19.

Yes another aspect of the application relates to a composition comprising a mixture of peptides labeled with at least one of a first TMT and a second TMT, optionally one or more unlabeled peptides, wherein the first TMT and the second TMT do not have the same reporter ion mass, and the mixture of peptides comprises at least one peptide that is conjugated to a drug and labeled with the at least one of the first TMT and the second TMT.

Other aspects, features and advantages of the invention will be apparent from the following disclosure, including the detailed description of the invention and its preferred embodiments and the appended claims, which are exemplary and nonlimiting, as would be appreciated by a person having ordinary skill in the art.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

Unless indicated otherwise, in all the drawings herein, the reporter ion of IdoTMT is represented by ◎ the reporter ion of TMT6 is represented by ✸ the analyzed peptide is represented by ●, and the drug is represented by ■

FIG. 1A—IodoTMTsixplex set, FIG. 1B—TMTsixplex set, FIG. 1C—TMT10plex set, FIG. 1D—TMTpro 16 plex, including the chemical structures and 13C and 15N stable isotope positions (*) of the TMTs;

FIG. 4 shows several exemplary experimental ADC systems that are analyzed by methods of the invention, which includes NIST monoclonal antibody (mAb) cysteine conjugated to iodoacetamide (IAA) and Biotin-PEO acetamide conjugate formed by conjugation with Biotine PEO Iodoacetamide, NIST mAb or HSA peptides containing 1-3 cysteine conjugated to N-(7-dimethylamino-4-methyl-3-coumarinyl)malemide (DACM-3), and the ADC standard MSQC8 (Dansyl fluorophore LC-SMCC crosslinker) from Sigma;

FIG. 12A shows MS2 TMT reporters for the synchronous precursor ion selection (top 5 fragments);

FIG. 12B shows the SPS-MS3 improves quantification sensitivity and accuracy when co-solation of interferences; and FIG. 12C shows the reporter quantification, wherein the ADC is SigmaMAb ADC mimic (MSQC8)—human universal mAb standard conjugated to dansyl fluorophore, and the mock is the human universal mAb standard (MSQC4, an IgG1 mAb) Sigma mAb not conjugated to a drug;

FIG. 20B shows the normalized occupancies obtained for the four samples in a single acquisition.

DETAILED DESCRIPTION OF THE INVENTION

Figure 1A:
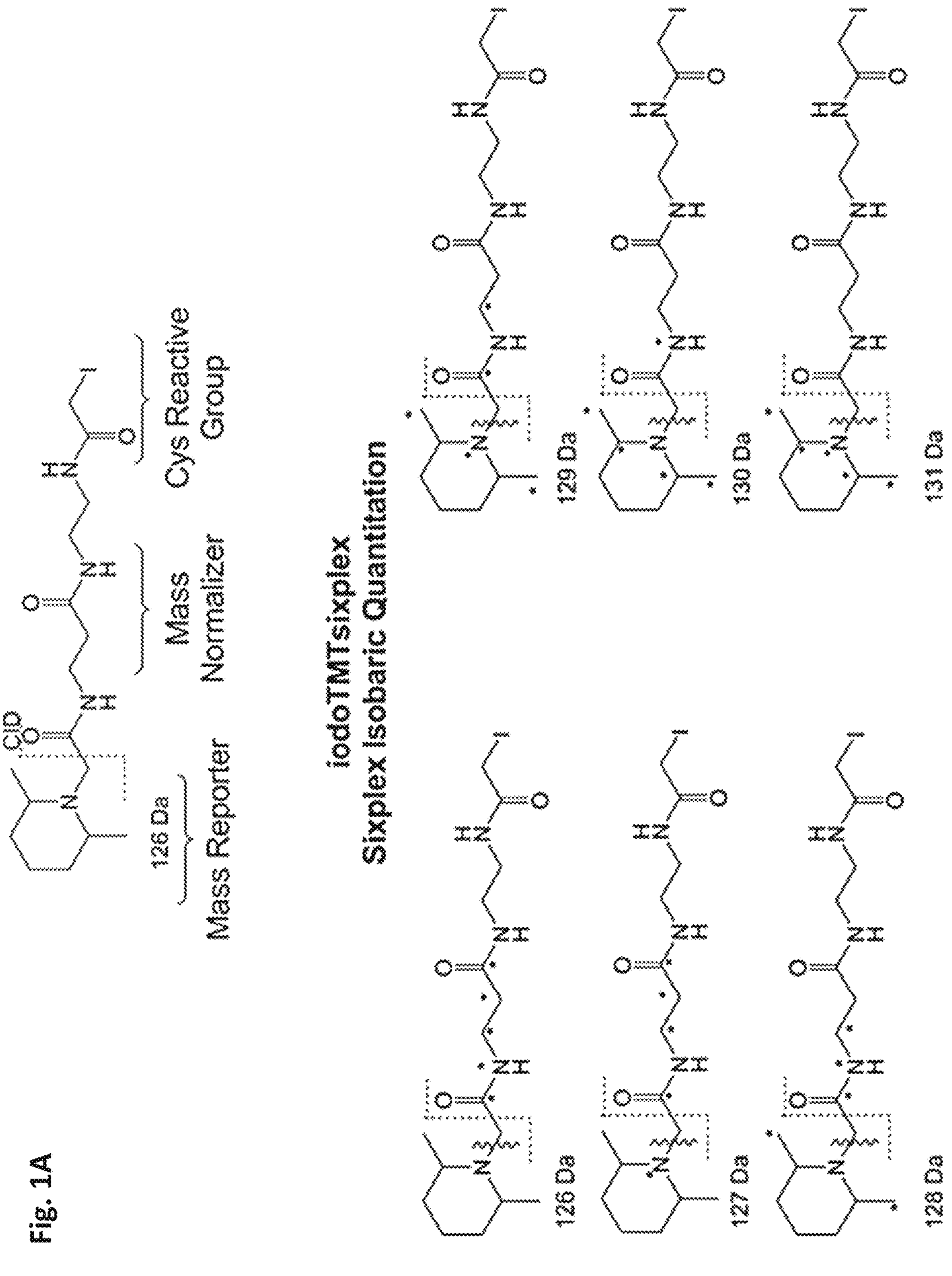
FIG. 1A-1D illustrate the structure of exemplary tandem mass tags (TMTs) useful to label cysteines in a polypeptide.

Unless defined otherwise, all technical and scientific terms used herein have the same meaning as is commonly understood by one of ordinary skill in the art to which this invention pertains. Otherwise, certain terms used herein have the meanings as set in the specification. All patents, published patent applications and publications cited herein are incorporated by reference as if set forth fully herein.

Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

It must be noted that as used herein and in the appended claims, the singular forms “a,” “an,” and “the” include plural reference unless the context clearly dictates otherwise.

Unless otherwise stated, any numerical value, such as a concentration or a concentration range described herein, are to be understood as being modified in all instances by the term “about.” Thus, a numerical value typically includes ±10% of the recited value. For example, an amount of about 50 ppm or less includes 45 ppm or less to 55 ppm or less. As used herein, the use of a numerical range expressly includes all possible subranges, all individual numerical values within that range, including integers within such ranges and fractions of the values unless the context clearly indicates otherwise.

Throughout this specification and the claims which follow, unless the context requires otherwise, the word “comprise,” and variations such as “comprises” and “comprising,” will be understood to imply the inclusion of a stated integer or step or group of integers or steps but not the exclusion of any other integer or step or group of integer or step. When used herein the term “comprising” can be substituted with the term “containing” or “including” or sometimes when used herein with the term “having.”

When used herein “consisting of” excludes any element, step, or ingredient not specified in the claim element. When used herein, “consisting essentially of” does not exclude materials or steps that do not materially affect the basic and novel characteristics of the claim. Any of the aforementioned terms of “comprising”, “containing”, “including”, and “having”, whenever used herein in the context of an aspect or embodiment of the application can be replaced with the term “consisting of” or “consisting essentially of” to vary scopes of the disclosure.

As used herein, the conjunctive term “and/or” between multiple recited elements is understood as encompassing both individual and combined options. For instance, where two elements are conjoined by “and/or,” a first option refers to the applicability of the first element without the second. A second option refers to the applicability of the second element without the first. A third option refers to the applicability of the first and second elements together. Any one of these options is understood to fall within the meaning, and therefore satisfy the requirement of the term “and/or” as used herein. Concurrent applicability of more than one of the options is also understood to fall within the meaning, and therefore satisfy the requirement of the term “and/or.”

As used herein, “MS/MS” or “$MS^2$” or “MS2” refers to tandem mass spectrometry. Tandem mass spectrometry is a technique in instrumental analysis where two or more mass analyzers are coupled together using an additional reaction step to increase their abilities to analyze samples. Tandem use of mass analysis can be done where the reaction steps are separated in space (tandem in space) and/or reaction steps are separated in time (tandem in time). A common use of tandem mass spectrometry is the analysis of biomolecules, such as proteins, peptides, organic and inorganic molecules, lipid, metabolites, and oligonucleotides.

As used herein, “reporter ion” or “diagnostic ion” refers to a characteristic product ion of a labeled peptide containing an N-terminal tag or label, which is observed in the ETD mass spectrum. Usually, it is the most dominant product ion in the mass spectrum, and it is used to trigger subsequent MS/MS events to further sequence the labeled peptide.

As used herein, “tribrid technology” refers to a technology that uses hybrid mass spectrometers having more than a single type of mass analyzer. It enables the performance of tandem mass spectrometry experiments with great flexibility for TMT sample multiplexing. The tribrid technology can be used for characterization of challenging samples including low-abundance peptides in complex matrices, determination of positional and posttranslational isoforms of intact proteins, resolution of isobaric metabolites, and protein structure characterization using chemical crosslinking.

As used herein, “orbitrap” or “OT” refers to an ion trap mass analyzer that consists of two outer electrodes and a central electrode. This setup enables the orbitrap to function as both an analyzer and detector. Ions that enter the orbitrap are captured and oscillate around the central electrode and in between the two outer electrodes. Different ions oscillate at different frequencies, which results in their separation. The oscillation frequencies that induced by ions on the outer electrodes are measured and the mass spectra of the ions are acquired using image current detection.

As used herein, “isobaric” refers to having the same nominal molecular weight or formula weight. Preferably, isobaric TMTs useful for an invention of the application have the same mass and structure, and they are also called isotopomers.

As used herein, “ion” refers to a molecule that has a net electric charge due to the loss or gain of one or more electrons. Examples of an ion can be a, b, or y-type product ions that are the result of cleaved amide bonds along the backbone of a protein due to collision-induced dissociation (CID).

As used herein, “sequence ion” refers to an ion (or ions) that correspond to the product of a particular peptide that is split at a given peptide bond.

As used herein, “immonium ion” refers to an ion (or ions) that correspond to an internal fragment of a peptide that has a single side chain formed by a combination of -type or y-type cleavage.

As used herein, “reporter ion” refers to an ion that is cleaved from an isobaric tagged peptide by methods known in the art (e.g., $MS^2$).

As used herein, “isotopologue” refers to a molecule that differs from its parent molecule in that at least one atom has a different number of neutrons.

As used herein, “multipole” refers to an ion guide that is comprised of metal rods to transport ions through a vacuum system.

As used herein, “conjugate” refers to a protein or peptide covalently linked to one or more heterologous molecule(s). Examples of the protein or peptide that can be covalently linked to the heterologous molecule(s) include, but are not limited to, a therapeutic peptide or protein, an antibody or a fragment thereof. Examples of the heterologous molecule(s) that can be covalently linked to the protein or peptide include, but are not limited to, one or more small molecule compounds, a label, etc.

As used herein, “peptide” refers to an amino acid based polymer usually composed of some combination of the twenty common naturally-occurring amino acids, but can also contain or be completely composed of unnatural amino-acid monomer residues. It can include a linear amino acid polymer configuration, or can include a cyclic peptide, or a branched one, or any combination of all three configurations. A peptide can also have any combination of naturally occurring modifications (e.g., phosphorylation or glycosylation) or unnaturally occurring modifications (e.g., carbamidomethylation).

“Antibody” shall include, without limitation, (a) an immunoglobulin molecule comprising two heavy chains and two light chains and which recognizes an antigen; (b) a polyclonal or monoclonal immunoglobulin molecule; and (c) a monovalent or divalent fragment thereof. Immunoglobulin molecules can derive from any of the commonly known classes, including but not limited to IgA, secretory IgA, IgG, IgE and IgM. IgG subclasses are well known to those in the art and include, but are not limited to, human IgG1, IgG2, IgG3 and IgG4. Antibodies can be both naturally occurring and non-naturally occurring. Furthermore, antibodies include multi-specific antibodies, such as bi-specific antibodies, tri-specific antibodies, tetra-specific antibodies, wholly synthetic antibodies, single chain antibodies, and fragments thereof. Antibodies can be human or nonhuman. Antibody fragments include, without limitation, Fab fragments, Fv fragments and other antigen-binding fragments.

As used herein, a "tandem mass tag" or "TMT" refers a chemical label that can be used for mass spectrometry (MS)-based quantification and identification of a molecule. Any molecule that has free thiols or primary amines or glycans can be tagged. For example, the molecule can be a protein or peptide. The TMT tags typically contain at least three regions, e.g., a mass reporter region, a mass normalization or balance region, and a reactive group. The reporter mass can be incremented to create unique masses while the balance mass is used to-offset the total mass of the reagent to make a series of reagents that have the same overall mass yet having a distinct reporter mass. The reactive group facilitates the addition reaction of amines, thiols, oxonium or other functional groups. It can be, for example, free thiol or reduced cysteine reactive, primary amine or lysine reactive, or aminoxy reactive. Optionally, the TMT can also contain one or more cleavable linker regions.

An isobaric set of TMTs enable concurrent identification and multiplexed quantitation of proteins in different samples using tandem mass spectrometry. An isobaric set of n TMTs can contain a TMT and TMTs with n−1 isotopic substitutions. The chemical structures of all the tags within an isobaric set of TMTs are identical, but each contains isotopes substituted at various positions, such that the mass reporter and mass normalization regions have different molecular masses in each tag, while the TMTs have the same total molecular weights (isobaric) and structure so that during chromatographic or electrophoretic separation and in single MS mode, molecules labelled with different tags are indistinguishable. For example, each isobaric reagent can contain a different number of heavy isotopes in the mass reporter region, which results in a unique reporter mass during tandem MS/MS for sample identification and relative quantitation. Upon fragmentation in MS/MS mode, sequence information is obtained from fragmentation of the peptide back bone and quantification data are simultaneously obtained from fragmentation of the tags, giving rise to mass reporter ions. Each TMT within an isobaric set generate a unique reporter mass on the MS/MS spectrum.

TMT labels, such as those commercially available TMT labels, can multiplex samples (such as 6-plex, 10-plex or more) and are reactive toward cysteine or amines, respectively. Shifting the location of the heavy isotopes between the reporter group and the spacer, the total mass and chemical structure of each tag can be kept the same (isobaric). For example, the cysteine reactive IodoTMTsixplex reagents and amine reactive TMTsixplex reagents each have six identical reporter ion masses. However, each reporter ion is unique in mass to charge ratio (m/z), or the reporter mass, also called reporter ion mass. For example, the nominal reporter masses of 6 TMTs within the isobaric TMT6 set range from 126-131 Da (Dalton).

An isobaric label reagent set of "IodoTMTsixplex", also called "CysTMT", "IodoTMT", "IodoTMT6" or "IodoTMT$^6$", refers to an isobaric set of six TMTs that are iodoacetyl-activated for covalent, irreversible labeling of sulfhydryl (—SH) groups, and have the chemical structures shown in FIG. 1A. The TMTs contain a signature reporter group containing 13C and/or 15N isotopes (shown as * in FIGS. 1A-1D) connected to a reactive group by a spacer arm. The IodoTMTsixplex isobaric label reagent set is commercially available from ThermoFisher Scientific (Catalog No. 90101). The IodoTMT reagents react specifically with reduced cysteines (Cys) in peptides and proteins. IodoTMT Reagents can be differentiated by mass spectrometry (MS), enabling quantitation of the relative abundance of cysteine modifications, such as S-nitrosylation, oxidation and disulfide bonds, in cultured cells grown or treated with different conditions.

Figure 1B:
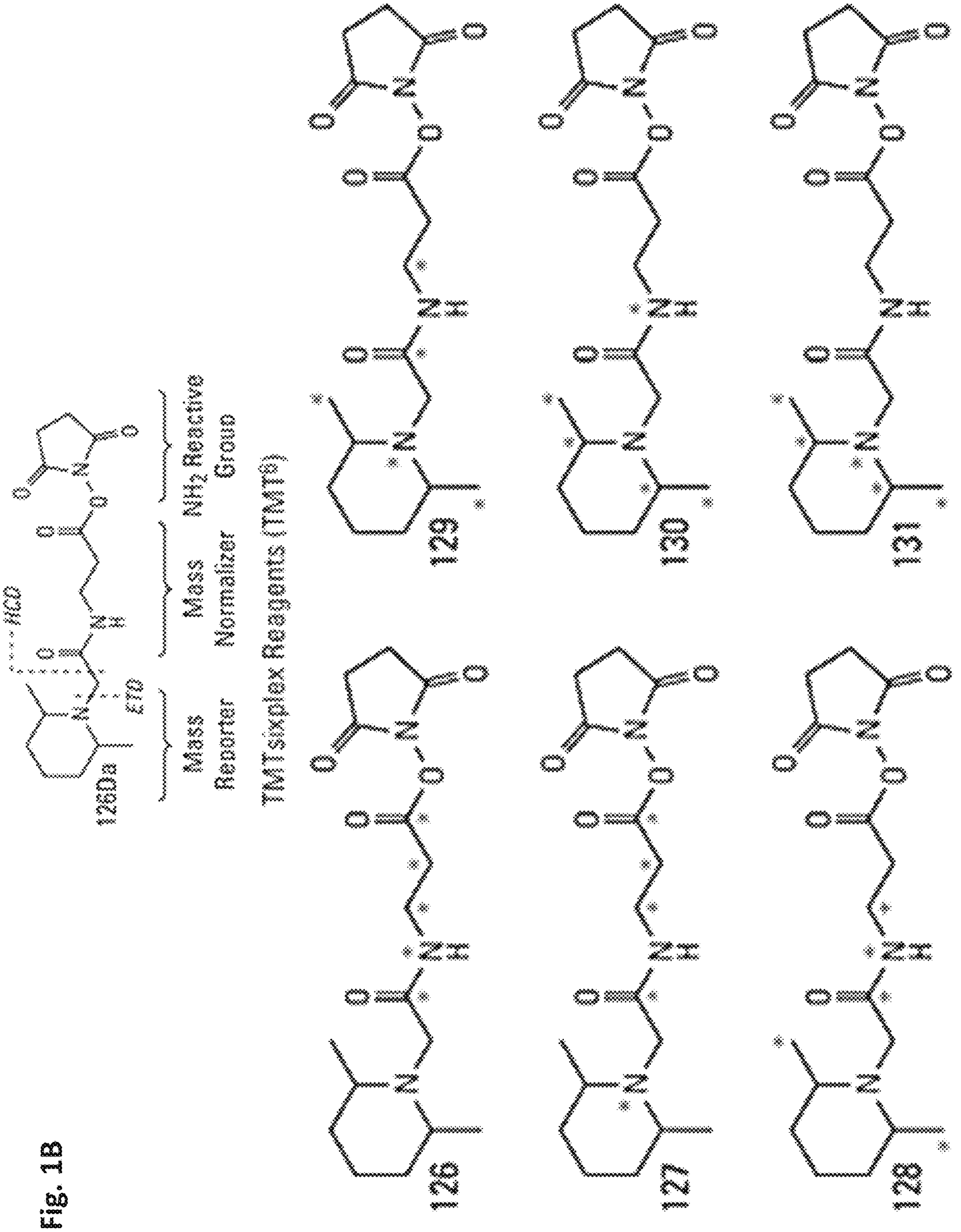

An isobaric label reagent set of "TMTsixplex", also referred to herein as "TMT6", "TMT$^6$", "TMT6 plex" refers to an isobaric set of six TMTs that are NHS-activated for covalent, irreversible labeling of primary amines (—NH2) groups and have the chemical structures shown in FIG. 1B. The TMTsixplex isobaric label reagent set is commercially available from ThermoFisher Scientific (Catalog No. 90061). The reagents label all peptides prepared from cell or tissue samples for analysis of up to six samples in a single MS analysis. According to ThermoFisher Scientific, the TMT6 reagents are optimized for use with high resolution Thermo Scientific MS/MS platforms, such as the Q Exactive, Orbitrap Elite™ and Orbitrap Fusion™ Tribrid™ Orbitrap Lumos™ instruments with data analysis fully supported by Proteome Discoverer™ 1.0 and above.

Figure 1C:
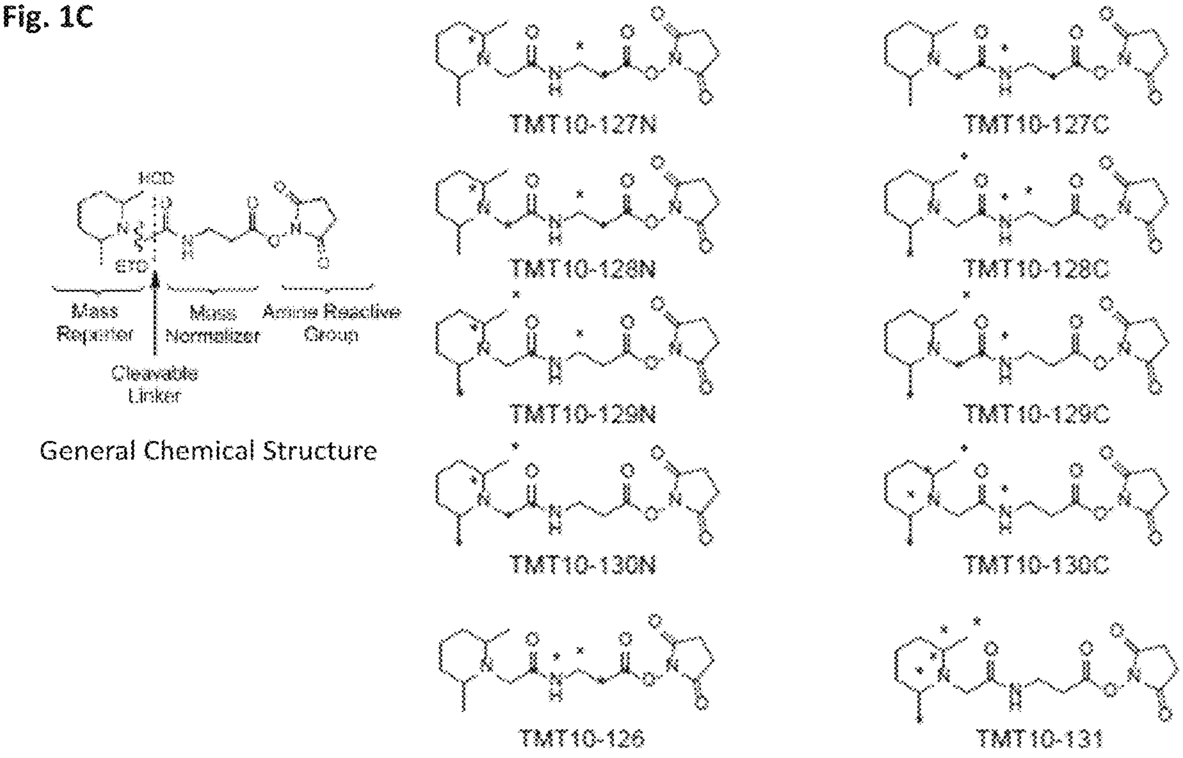

An isobaric label reagent set of "TMT10plex", also referred to herein as "TMT10", "TMT$^{10}$", or "TMT10 plex", refers to an isobaric set of ten TMTs each having an amine-reactive NHS-ester group, a spacer arm and a mass reporter, and having the chemical structures shown in FIG. 1C. The amine reactive TMT10plex can multiplex up to 10 separate samples (10-plex). The TMT10plex isobaric label reagent set is commercially available from ThermoFisher Scientific (Catalog No. 90110). It is important to note that the 10-plex reagents still have six nominal masses (126-131 Da), however, four of the six reporter masses (127-130 Da) each have two unique reporter ion masses that differ by 6.32 mDa (milli Dalton) where a $C^{12}$, $N^{15}$ atom pair is substituted with $C^{13}$, $N^{14}$. High-resolution mass spectrometry enables accurate relative quantitation of baseline resolution of these reporter ion masses and their isotopologues. The reagent set enables up to ten different peptide samples prepared from cells or tissues to be labeled in parallel and then combined for analysis. For each sample, a unique reporter mass (i.e., TMT10 126-131 Da) in the low-mass region of the high-resolution MS/MS spectrum can be used to measure relative protein expression levels during peptide fragmentation and tandem mass spectrometry. According to ThermoFisher Scientific, TMT10 reagents are optimized for use with high resolution Thermo Scientific MS/MS platforms, such as the Q Exactive, Orbitrap Elite™ and Orbitrap Fusion™ Orbitrap Elite™ Tribrid™ instruments with data analysis fully supported by Proteome Discoverer™ 1.4.

Figure 1D:
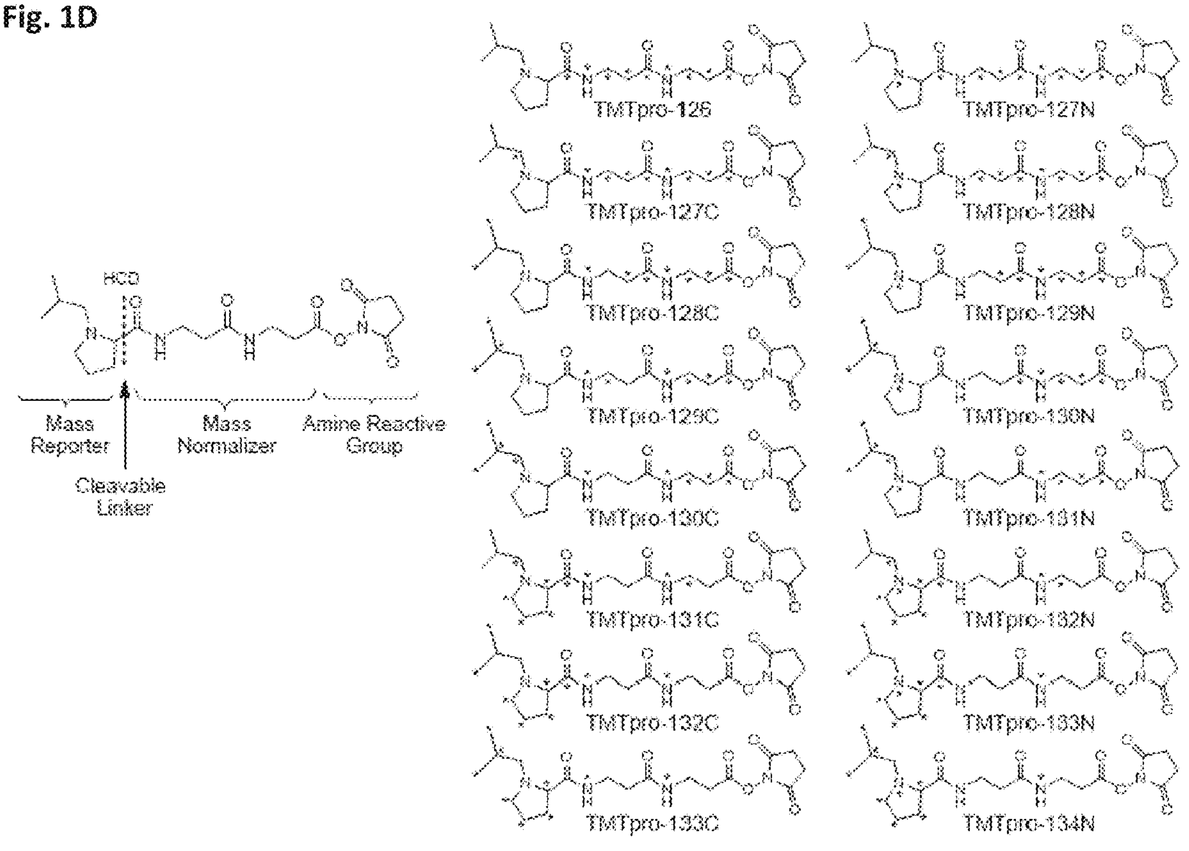

An isobaric label reagent set of "TMTpro 16plex", also referred to herein as "TMT16", "TMT$^{16}$", "TMTpro" or "TMTpro16 plex", refers to an isobaric set of 16 amine-reactive NHS ester-activated reagents having the chemical structures shown in FIG. 1D. The 16 TMTs each have a group reactive with lysine or primary amine at the N-terminus. The TMTpro 16 plex is commercially available from ThermoFisher Scientific (Catalog No. A44520). According to ThermoFisher Scientific, TMTpro label reagents are the next generation of tandem mass tags that are optimized for use with high resolution Thermo Scientific MS/MS platforms, such as the Q Exactive and Orbitrap Fusion Tribrid instrument series, including the Orbitrap Eclipse Tribrid and Orbitrap Exploris 480 mass spectrometers with data analysis fully supported by Proteome Discoverer 2.3.

A set of 6 reporters (TMT-6 plex), set of 10 reporters (TMT-10 plex), set of 11 reporters (TMT-11 plex) and up to 16 reporters (TMT-16 plex) of such TMTs can be used in methods of the invention. Other examples of TMTs can also be used in the invention in view of the present disclosure. In particular, TMT16-plex and future n-plex reagents where n>16 would increase the number of samples that can be labeled with dual TMT labeling. The TMTs can be made using methods known in the art or obtained from commercial sources such as ThermoFisher Scientific. When two TMTs are used in tandem, however, they cannot have the same reporter ion mass. For example, because IodoTMT and TMT6 have the same series of reporter masses, when the isobaric sets of IodoTMT and TMT6 are used for dual labeling, the selected IodoTMT(s) and TMTs must not have the same reporter mass when they are used for dual labeling. Similarly, when more than two TMTs are used in the same analysis, such as the TMTs used for the analysis of the sample and mock together or for the analysis of multiple samples together, each of the TMTs used in the analysis must have unique reporter mass, or none of the TMTs used in the same assay can have the same reporter mass.

An important metric for ADC efficiency, safety, and selectivity is determined by drug-antibody ratios (DARs). Chromatographic approaches, e.g., size exclusion chromatography (SEC), hydrophobic interaction chromatography (HIC), and reversed phase liquid chromatography (RPLC), can possibly be used to obtain the DAR value and characterize ADCs. However, these approaches have significant disadvantages, for example they, for example, they usually exhibit low throughput due to the long separation and column regeneration times. Moreover, certain required mobile phases prevent online coupling to mass spectrometry (MS). Native MS-based approaches preserve non-covalent interactions and consequently can obtain information on the array of possible drug conjugate species.

Another approach is ion mobility spectrometry coupled with mass spectrometry (IMS-MS). IMS-MS obtains both structural and mass information in a single assay. It has demonstrated agreement in DAR characterization between IMS-MS and MS. Therefore, IMS-MS can be used to study the drug load distributions of ADCs and characterize mAbs.

However, the conventional methods for quantification and identification of drug conjugates have the drawbacks of arbitrary, low sensitivity, insufficient selectivity and/or relative long analysis time or high costs. For example, native MS, chromatographic, and IMS-MS approaches provide little information on site-specific drug conjugation of the mAb and whether the occupancy and location of drugs bound to the antibody alters the selectivity or efficacy of the ADC. Identification of the peptide with the complete drug molecule is challenging due to the size of the small molecule and the linker.

A ratio can be obtained to quantify conjugated peptides by normalizing the conjugated peptide intensity with the sum intensities of the unmodified peptide counterpart and the conjugated peptide. This Ad hoc ratio facilitates relative estimation of the conjugate-levels across samples for the site of interest. Stoichiometry-based approaches can also be used where the occupancy of a modification is indirectly determined by chemically removing the modifications or using a stable isotope labeled synthetic peptides and stable isotope labeled cell lines (See, e.g., Wu et al., *Nature methods* 8, 677-683 (2011); Lim et al., *Journal of proteome research* 16, 4217-4226 (2017)). Isobaric labeling specific to primary amines have been utilized to study occupancy of model NIST mAb to show the utility of a stoichiometry-based approach based on isobaric labeling (Hill et al., *Sci Rep* 8, 17680 (2018)). Nonetheless, stoichiometry-based quantification methods have not been integrated into the pharmaceutical pipeline for quantification or ADC analysis due to, for example, complex and challenging sample preparation, elaborate analytical schemes required to obtain compositional differences based on drug conjugation, etc. (Janin-Bussat et al., *Journal of chromatography. B, Analytical technologies in the biomedical and life sciences* 981-982, 9-13 (2015); Le et al., *Anal Chem* 84, 7479-7486 (2012)).

An isobaric set of TMTs can be used to label and study a set of drug polypeptide conjugates, such as ADCs. Using high-resolution mass spectrometry, baseline resolution of these reporter ion masses and their isotopologues are possible for accurate relative quantitation. In one aspect of the application, TMTs are used in tandem mass spectrometry ($MS^2$) analysis of a sample, particularly a drug conjugate, for the characterization of the sample based on a mass spec bar code of the sample.

A mass spectrum is a histogram acquired using a mass spectrometer. The mass spectrum of an analysis is usually plotted as intensity (Y) vs. m/z (mass-to-charge) ratio (X) plot. A reporter ion for a TMT can be detected by its m/z ratio on a mass spectrum. The Y-axis represents the signal intensity of the ions.

Depending on the instruments and software, the signal intensity can be measured and expressed differently. For example, when using counting detectors the intensity is often measured in counts per second (cps). When using analog detection electronics the intensity is typically measured in volts. In Fourier-transform ion cyclotron resonance mass spectrometry and Orbitraps, the frequency domain signal (the y-axis) is related to the power (~amplitude squared) of the signal sine wave (often reduced to an rms power). Some software calculates reporter area rather than intensity. As used herein, with respect to a mass spectrum, the term "intensity" encompasses signal intensity of ions measured by any method and expressed in any format. For example, the "intensity" of a reporting ion can include reporter intensity, reporter area, or any other variations of signal intensity of ions from mass spectrometry analysis.

As used herein, a "mass spec bar code", "MS bar code", "reporter ions masses barcode," "barcode" or "mass barcode" of a sample refers to a measurement of the sample from a tandem mass spectrometry ($MS^2$) analysis that contains information of a set of reporter ions and the measurement is unique to the sample. A unique barcode for a sample can be based on the intensity and/or the presence (pattern) or absence of the set of TMT reporter ions detected from the tandem $MS^2$. One or more barcodes can be used in the triple play analysis of the sample.

Figure 2:
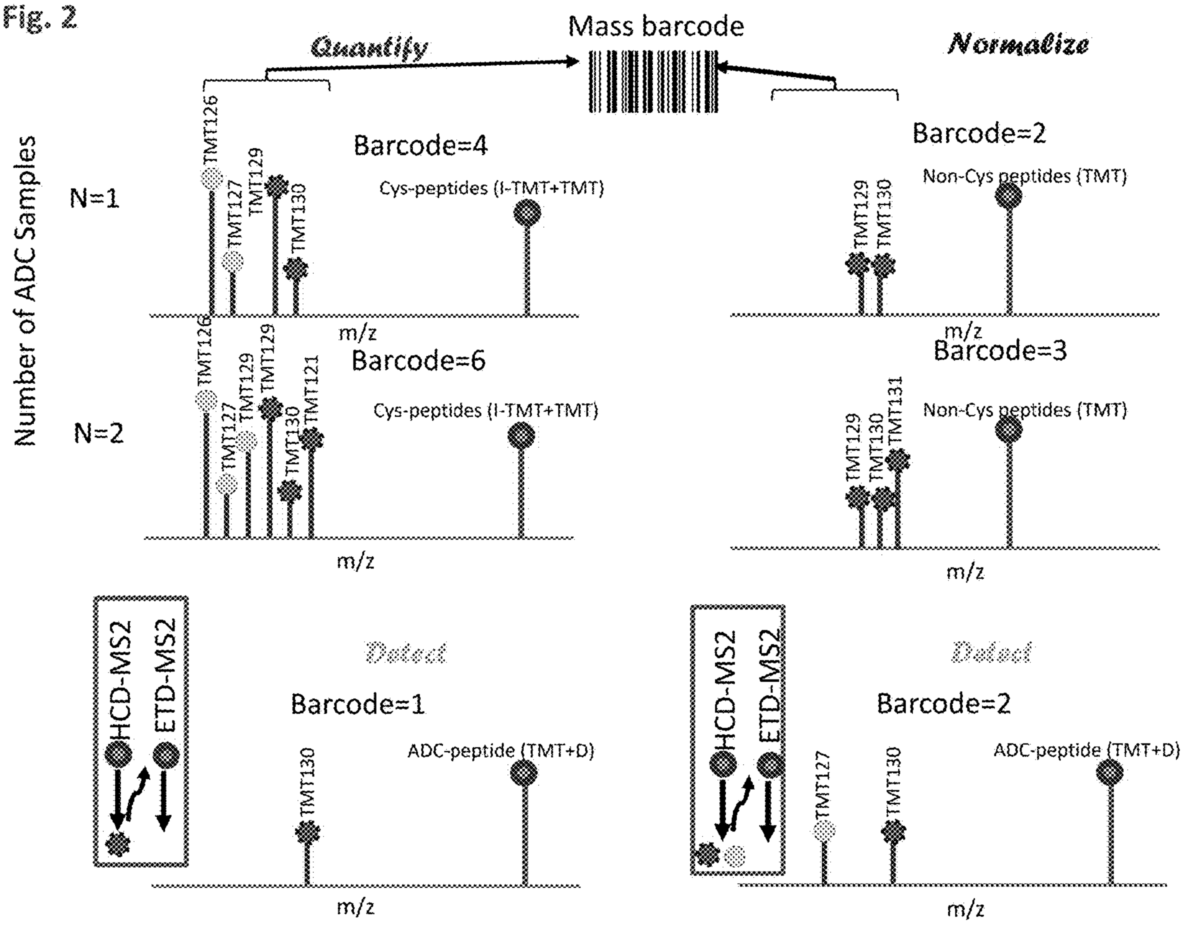
FIG. 2 shows the creation of unique bar codes according to embodiments of the application for sample characterizations, e.g., to quantify (e.g., occupancy of the drug), normalize (e.g., normalize mock vs. conjugate), and detect (e.g., localize the drug conjugation site) the samples based on the intensity and combination of the predetermined TMT reporters (pattern) detected from a tandem mass spectrometry ($MS^2$) analysis.

FIG. 2 illustrates the use of IodoTMTsixplex and TMT6 to multiplex 6 different cell lysates where labeling can be performed on the proteins prior to digestion or on the surrogate peptides that have cysteines after digestion of each sample. Each of the six samples can be labeled with a TMT within the IodoTMT set, combined and subject to a LC-$MS^2$ analysis together to obtain a distinct barcode for each of the six samples. The barcode is defined by the intensity and pattern of the m/z of the reporter ions generated by the TMT on the tandem mass spectrum. In particular, the labeling generates isobaric mass of the same peptide for each cell-line which is indistinguishable by mass. However, after dissociation by either collision (HCD) or via electron-based dissociation (ETD), unique reporter ions are generated. It is important to note that HCD generates a series of charged fragment where the entire reporter is dissociated, while ETD generates a second series of unique reporter ion masses. Similar, TMT labeling can also be used in proteomics to compare 6, 10, 11, and 16 sets of reporters of different samples of any peptide, because every peptide has an N-terminus and TMT reagents can label the N-terminus amine and/or lysine to thereby attach to all peptides.

Accordingly, the present application provides an improved method for accurate, sensitive and efficient identification and quantification of drug conjugates. In one aspect of the invention, a drug polypeptide conjugate, such as an ADC, is sequential labeled with a first TMT, such as a Cys reactive IodoTMT, and a second TMT, such as a TMT reactive to the Lys or primary amine at the N-terminus, and the labeled drug conjugate is subject to tandem mass spectrometry analysis. The sequential labeling scheme helps interrogate drug conjugates. Two parallel sample preparation arms can be used to label the drug conjugate (conjugate sample) and unconjugated mock (reference or control sample) according to embodiments of the application. Both labels facilitate encoding of unique reporter ion signatures that distinguish the sample and mock or reference. The reference sample produces reference reporter ion channels and the conjugate sample produces sample reporter ion channels. Unique reporter ions are generated after dissociation by either HCD or via electron-based dissociation such as ETD. The number of channels in the reporter ion region, their ratios and/or other mass spec performing specifics associated with the TMTs can be used to create a unique barcode to characterize the drug conjugate. For example, the bar code can comprise a distinct set of reporter ion and/or mass barcodes.

Figure 3A:
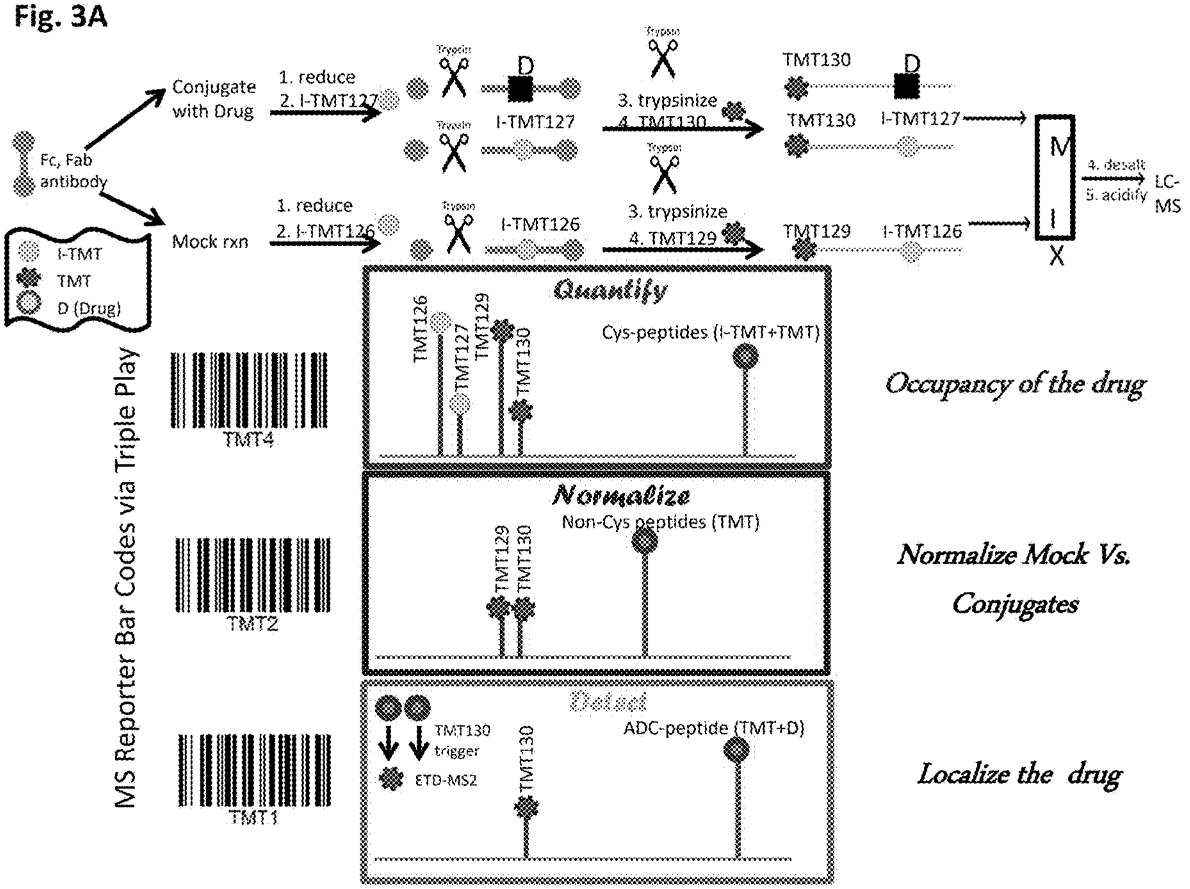
FIG. 3A illustrates an embodiment of the application that creates MS barcodes via triple play by sequential dual TMT labeling of the conjugate with Drug (D), such as an antibody or fragment thereof conjugated with a drug, and a Mock, such as the antibody or fragment thereof not conjugated with a drug, using an analysis scheme that can quantify, normalize, and localize.

As illustrated in FIG. 3A, a method of the application can be used to quantify the occupancy of a drug in the conjugate, e.g., by comparing the mass spectrum of the lower m/z regions reporter ion intensities of the Cys-containing peptides in the conjugate with that in a mock control containing the polypeptide that is not conjugated to the drug. The method can also be used to normalize the mock control and the conjugate.

Another aspect of the application relates to a method of localizing the conjugation site on the polypeptide, e.g., by using one or two TMT reporter ions to trigger additional dissociation step to further characterize the peptide covalently linked to the drug. In one embodiment of the application, one or two TMT reporter ions are produced using a first tandem mass spectrometry analysis, such as an HCD analysis. The reporter ion(s) is then used to trigger an ETD scan of the peptide to obtain an ETD spectrum. The ETD spectrum complements the HCD spectrum for characterizing the conjugate such that ETD provides sequence ions that assist in the localization of the residue with the drug conjugate. Alternatively, the reporter ion(s) is then used to trigger an ECD scan to obtain an ETD spectrum for further analysis of the peptide.

Figure 3B:
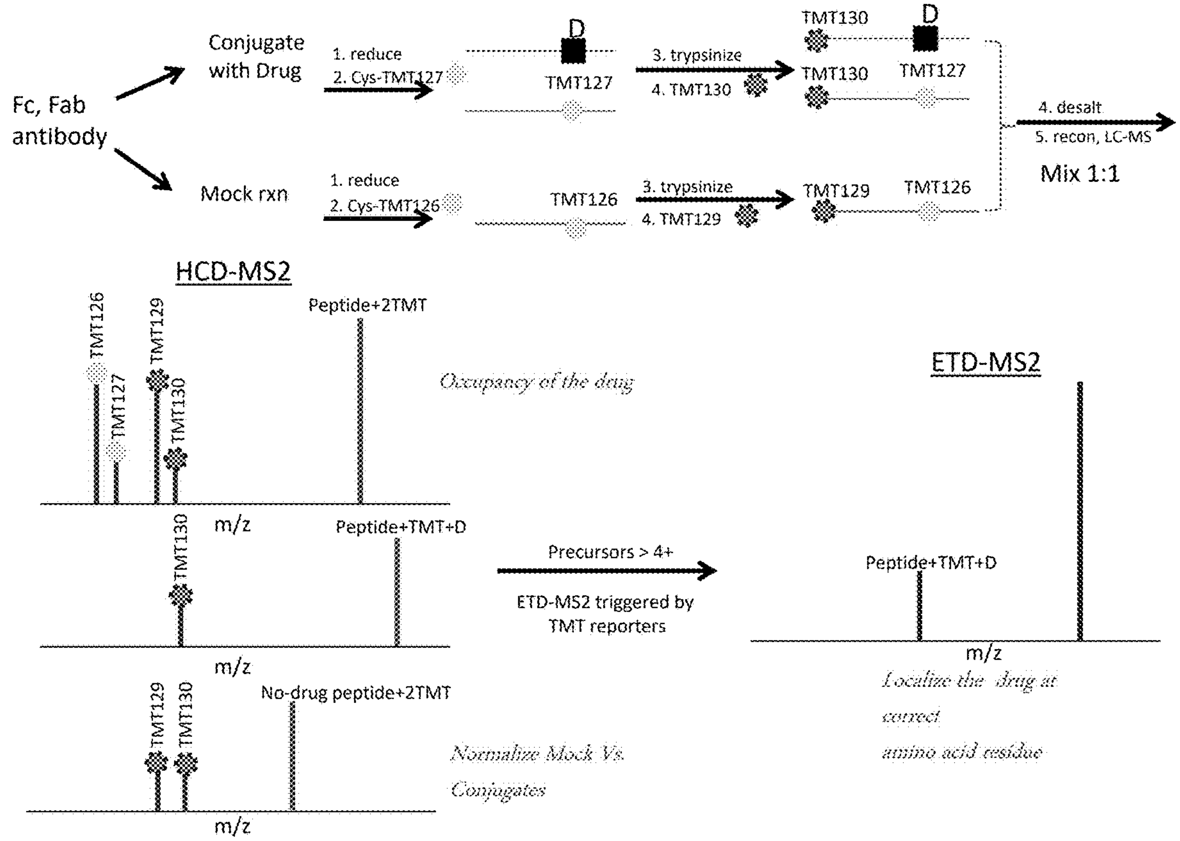
FIG. 3B illustrates a process of using the dual TMTs for quantifying a drug conjugate with one drug (D) conjugated to a peptide obtained by the trypsin digestion, according to an embodiment of the application.
Figure 3C:
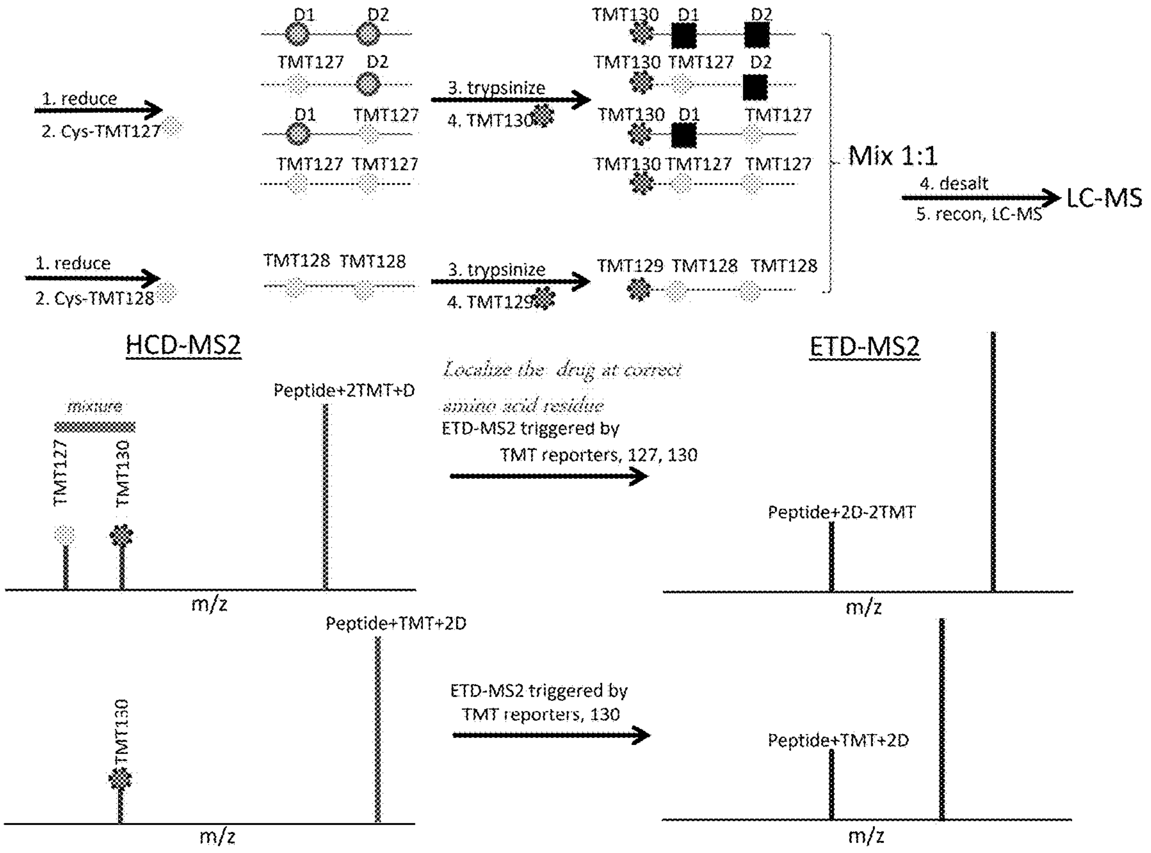
FIG. 3C illustrates a process of using dual TMTs for quantifying a drug conjugate with up to two drugs (D1 and D2) conjugated to a peptide obtained by the trypsin digestion, according to an embodiment of the application.

FIGS. 3A-C demonstrate the dual TMT workflow where IodoTMT6 and TMT6 are used for labeling mAbs and their drug conjugates. In particular, IodoTMT6 is used to multiplex 6 different samples (e.g., cell lysates). In this case, the labeling can be performed on the proteins prior to digestion or on the surrogate peptides that have cysteines after digestion of each sample. Both iodoTMT6 and TMT6 reagents have reporters with the same nominal mass. Isobaric labeled peptides are produced due to the selection of reagents with non-overlap in masses. Sequential labeling is performed first with iodoTMT6 of the mAb followed trypsinization and labeling peptides obtained by trypsin digest with TMT6 labels. Peptides from the conjugate sample and mock are mixed in equimolar ratio and subject to LC-MS. The sequential labeling scheme described here is a novel methodology to interrogate peptides, which facilitates the creation of a mass spec bar code according to an embodiment of the application.

In certain embodiments, an illustrated workflow has two parallel sample preparation arms, for the drug conjugate and unconjugated mock. For example, both IodoTMT6 and TMT6 labels facilitate encoding of unique reporter ion signatures that distinguish the sample and mock or reference, e.g., reference sample produce reference reporter ion channels and conjugate sample produces sample reporter ion channels. Also, the number of channels in the reporter ion region and their ratios encodes for occupancy and the type of experimental measurement that can be obtained, and each experimental measurement has a distinct set of reporter ions or mass barcodes.

Accordingly, an aspect of the application relates to a composition comprising a mixture of peptides labeled with at least one of a first TMT and a second TMT, optionally one or more unlabeled peptides, wherein the first TMT and the second TMT do not have the same reporter ion mass, and the mixture of peptides comprises at least one peptide that is conjugated to a drug and labeled with the at least one of the first TMT and the second TMT. For example, a composition of the application can comprise a mixture of peptides derived from a conjugate sample labeled with at least one of a first TMT and a second TMT, optionally one or more unlabeled peptides. The composition can also comprise a mixture of peptides derived from a conjugate sample described herein and a mixture of peptides derived from a mock sample labeled with at least one of a third TMT and a fourth TMT, optionally one or more unlabeled peptides.

FIG. 3A illustrates drug conjugation at a single cysteine seen in the surrogate tryptic peptide where iodoTMT labeling takes place at the free thiol of the mAb on the fraction that is unconjugated, prior to digestion. The sample preparation and LC-MS can remain the same irrespective of the number of conjugation sites. Data-dependent $MS^2$ or data-dependent SPS-$MS^3$ (synchronous precursor selection and triple-stage mass spectrometry) and TMT reporter ion triggered ETD-MS can take place in a seamless fashion under the complete controls of an instrument software be used to generate mass spec barcodes. This novel automated 3-step method is herein referred to as "triple play," wherein specific reporter ion combinations are used to quantify, normalize and detect a drug polypeptide conjugate. In some embodiments of the application, the triple play is conducted with dual TMT reporters to quantify the drug occupancy, normalize the drug conjugates in multiple samples, and detect or localize the site of conjugation (e.g., by triggering additional MS2). Preferably, the drug polypeptide conjugate is an ADC.

Referring to FIGS. 3A-B, following the work flow depicted in the figures, all peptides that carry a single cysteine conjugation site labeled with the iodoTMT labeling set produce four reporter ions (i.e., IodoTMT-126 and IodoTMT-127 and TMT-129 and TMT-130), while all non-cysteine labeled peptides produce two reporter ions TMT-129 and TMT-130, which can be used to correct for differences in sample mixing and normalizing. A single reporter TMT-130 found uniquely on drug conjugated peptides can be used to trigger additional ETD-$MS^2$ scans for site-localization (see, e.g., FIG. 3B). The TMT-130 reporter ion is agnostic to the drug that is conjugated to the peptide and does not rely on fragments of the drug. Consequently, triggered $MS^2$ can be used for any type of drug conjugate or to screen libraries of drugs that have unique reporter ions to readily identify and localize the drug.

Unlike peptides with a single cysteine, peptides with multiple cysteine residues can have drug covalently linked to one or more of the cysteine residues. For example, the two hinge cysteines of IgG1 and IgG4 mAbs have the possibility of double occupancy and single occupancy of any single cysteine. The four hinge cysteines on IgG2 (with IgG2-A, IgG2-B and IgG2-A/B isoforms) increase the possible combinatorial conjugation possibilities even further (Liu et al., MAbs 4, 17-23 (2012).

Figure 3D:
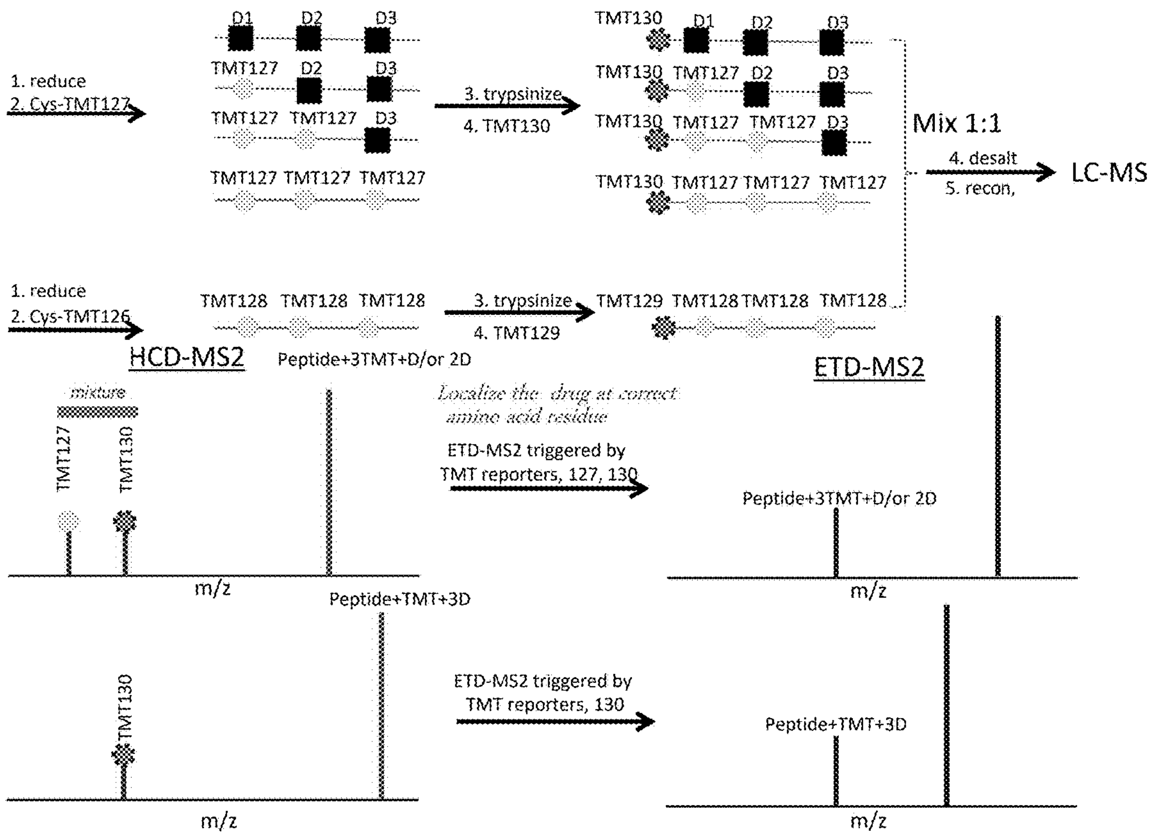
FIG. 3D illustrates using dual TMTs for quantifying a drug conjugate with up to three drugs (D1, D2, and D3) conjugated to a peptide obtained by the trypsin digestion, according to an embodiment of the application.

Methods according to embodiments of the application can be used to study a drug conjugate with one or more drugs conjugated to a polypeptide (such as an antibody). One or more drugs can be within a single digested peptide. The drug molecule(s) can be of the same type or different type. FIGS. 3B to 3D illustrate studies on drug conjugates containing one, two or three drugs on a single digested peptide, wherein D1, D2, and D3 can be identical or unique. The number of barcodes for quantitation and normalization does not change irrespective of the number of conjugate sites available and whether they are completely or partially conjugated. The occupancy in such instances is the total drug occupancy of all positional isoforms and the number of barcodes for normalization remains as two reporters. Moreover, if the number of conjugation sites within a single peptide is greater than 2 per peptide, then partial conjugation creates two reporters, e.g., TMT-127 and TMT-130 ions, and full conjugation creates a single reporter, e.g., TMT-130 ion, for triggering the ETD-MS2 scans for the occupancy study to localize the conjugated drug at the correct amino acid residues. As used herein, a peptide having a "complete conjugation" to a drug or "completely conjugated to a drug" refers to a peptide that covalently binds to the drug at all amino acid residues capable of conjugating to the drug. As used herein, a peptide having an "in complete conjugation" or "incompletely conjugated to a drug" refers to a peptide that covalently binds to the drug at only some but not all amino acid residues capable of conjugating to the drug. A peptide that completely conjugated to a drug can have one, two, three or more drugs conjugated to it.

Although, the sample preparation workflows remain the same for analyzing such conjugation reactions, the mass spectrometry parameters for TMT-triggering requires either 1 of 2 reporters or 2 of 2 reporters to be included in the trigger settings for localization of complete multiple conjugations or partial multiple conjugations respectively, respectively. Similar methods/schemes can be used to study drug conjugates containing more than three drugs using methods of the application in view of the present disclosure.

FIG. 4 shows several exemplary experimental ADC systems that are analyzed by methods of the invention. For example, the NIST mAb-Biotin PEO acetamide ADC has the Biotin PEO acetamide conjugated to the mAb and its mock control containing only the antibody without the conjugated drug. In addition to the antibodies or fragments thereof, drug conjugates with other polypeptides can also be characterized by a method of the application. Human serum albumin (HSA) peptides are used as an example. Unlike NIST, which only has one peptide with two cysteines, a HSA peptide has multiple cysteines on the same peptide. It was used tested in methods according to embodiments of the application, such as in the fluorescence assay as well as IodoTMT labeling.

In the representative structure shown in FIG. 4, two Biotin PEO acetamides are conjugated to the NIST mAb, one in the light chain and one in the heavy chain of the NIST mAb. However, the NIST mAb-Biotin PEO acetamide ADC can have several different isoforms with different combinations of occupancies where the Biotin PEO acetamide is present and attached to different cysteine residues within the NIST antibody with different levels or occupancies. Similarly, although the representative structure of MSQC8 shown in FIG. 4 only has one dansyl fluorophore conjugated to the mAb (MSQC4), it can have different isoforms with dansyl fluorophore conjugated to the mAb at one or more other sites.

Any ADC, including but not limited to any of the ADCs illustrated in FIG. 4, and its mock control can be subject to a tandem mass spectrometry analysis according to an embodiment of the application with dual TMTs, such as TMTs of a Cys reactive IodoTMT, and TMTs reactive to Lys or primary amine at the N-terminus. Examples of mass spectra obtained from the analysis, as well as the results from the analysis, are shown in, e.g., FIGS. 5A, 5B, 5C, 5D, 6A, 6B, 7, 9A-9D, etc.

Figure 5A:
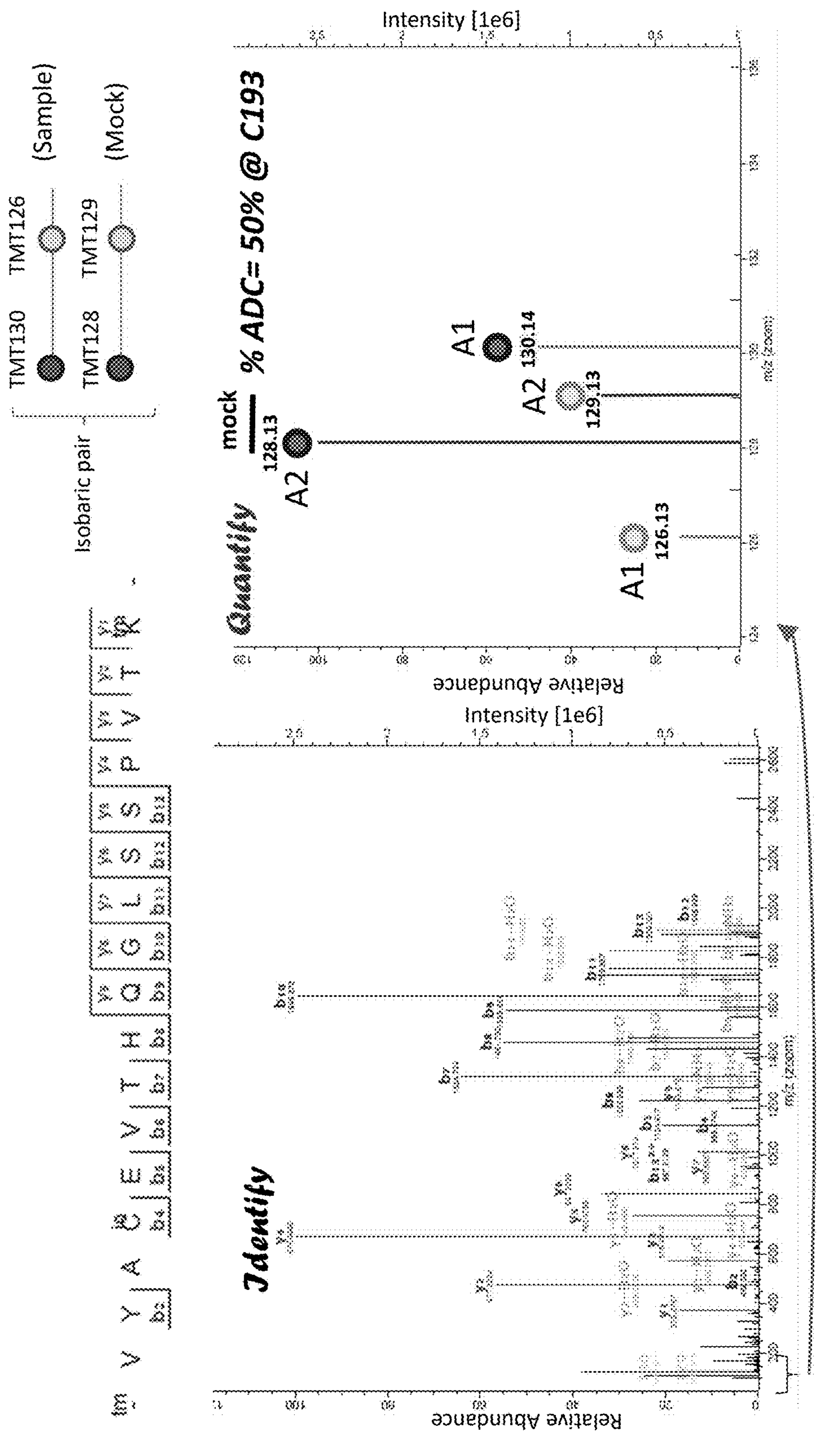
FIG. 5A and FIG. 5B each illustrate an embodiment of the application using dual TMTs for quantifying site-specific ADC on NIST mAbs by performing HCD-$MS^2$, although other $MS^2$ such as ETD-$MS^2$ can also be used, e.g., quantifying the occupancy of the drug on a specific residue using either iodoTMT (io, labeling the Cys residue or C) or TMT (tm, labeling the Lys residue or N-terminal amine) reporter ion intensities and applying to a formula that calculates % occupancies, wherein the ADC is NIST mAb-Biotin-PEO acetamide.
Figure 5B:
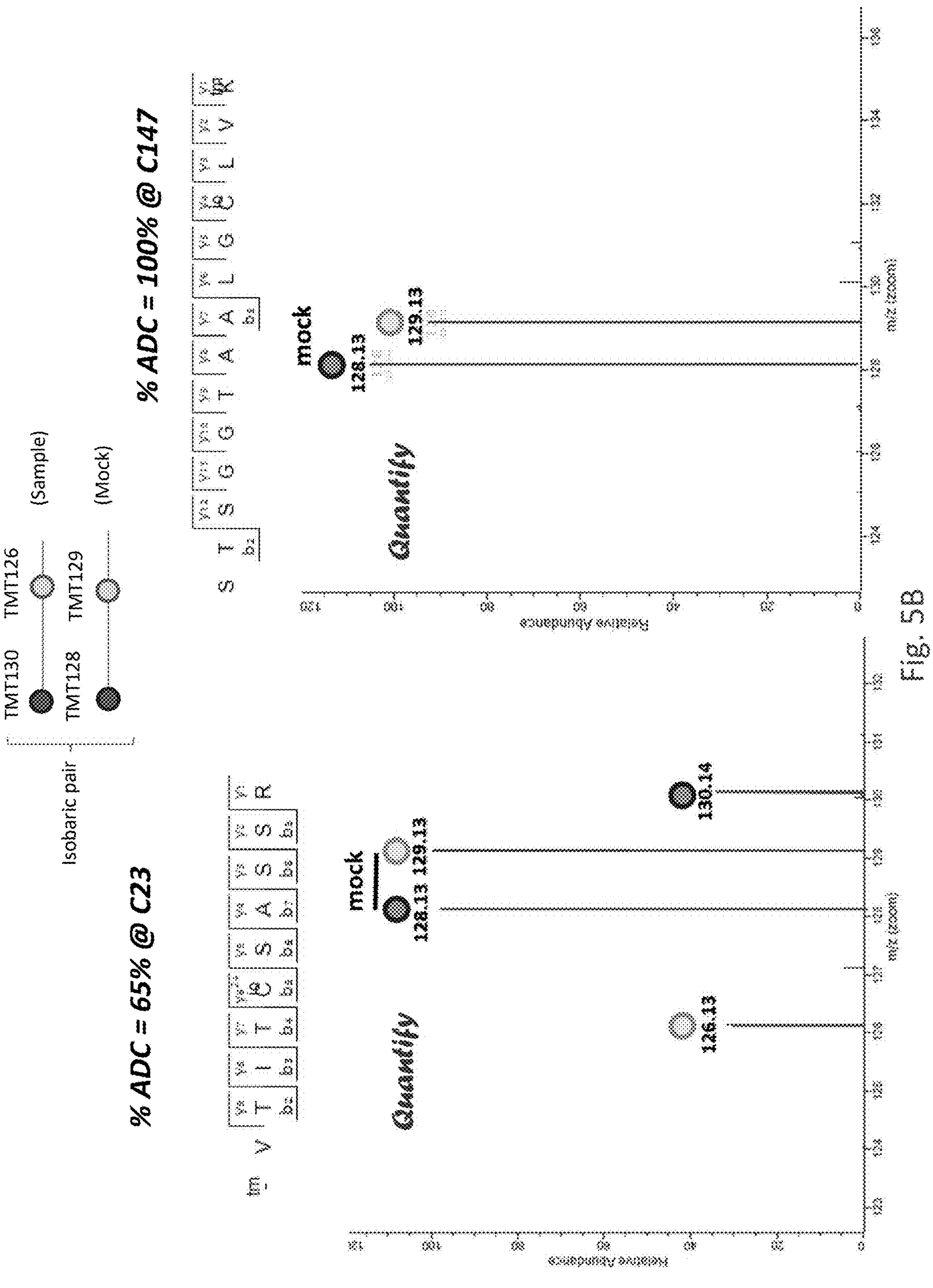
Figure 5C:
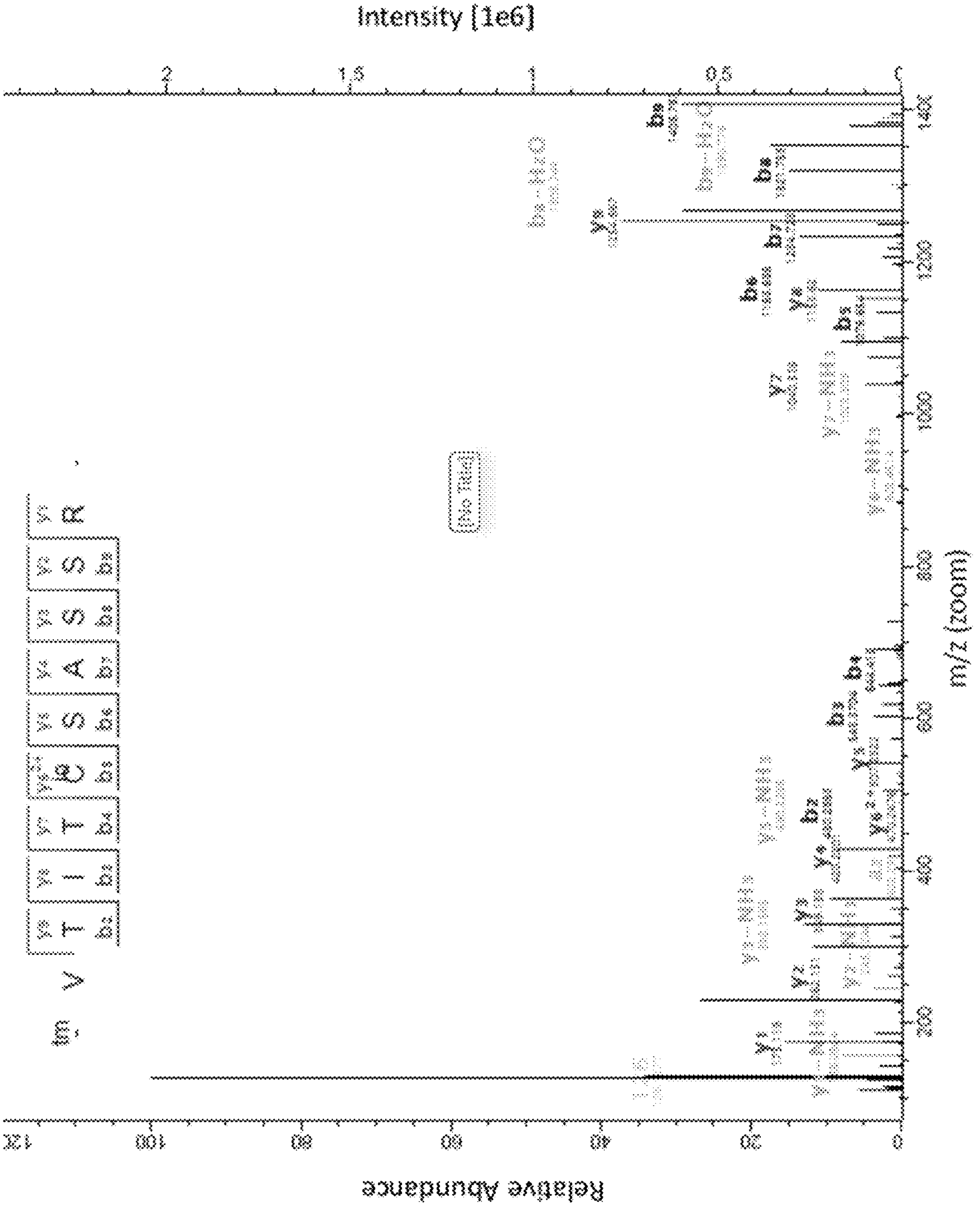
FIGS. 5C and 5D show the corresponding $MS^2$ spectra (with all backbone product ions) of the peptides sequenced by HCD-$MS^2$.
Figure 5D:
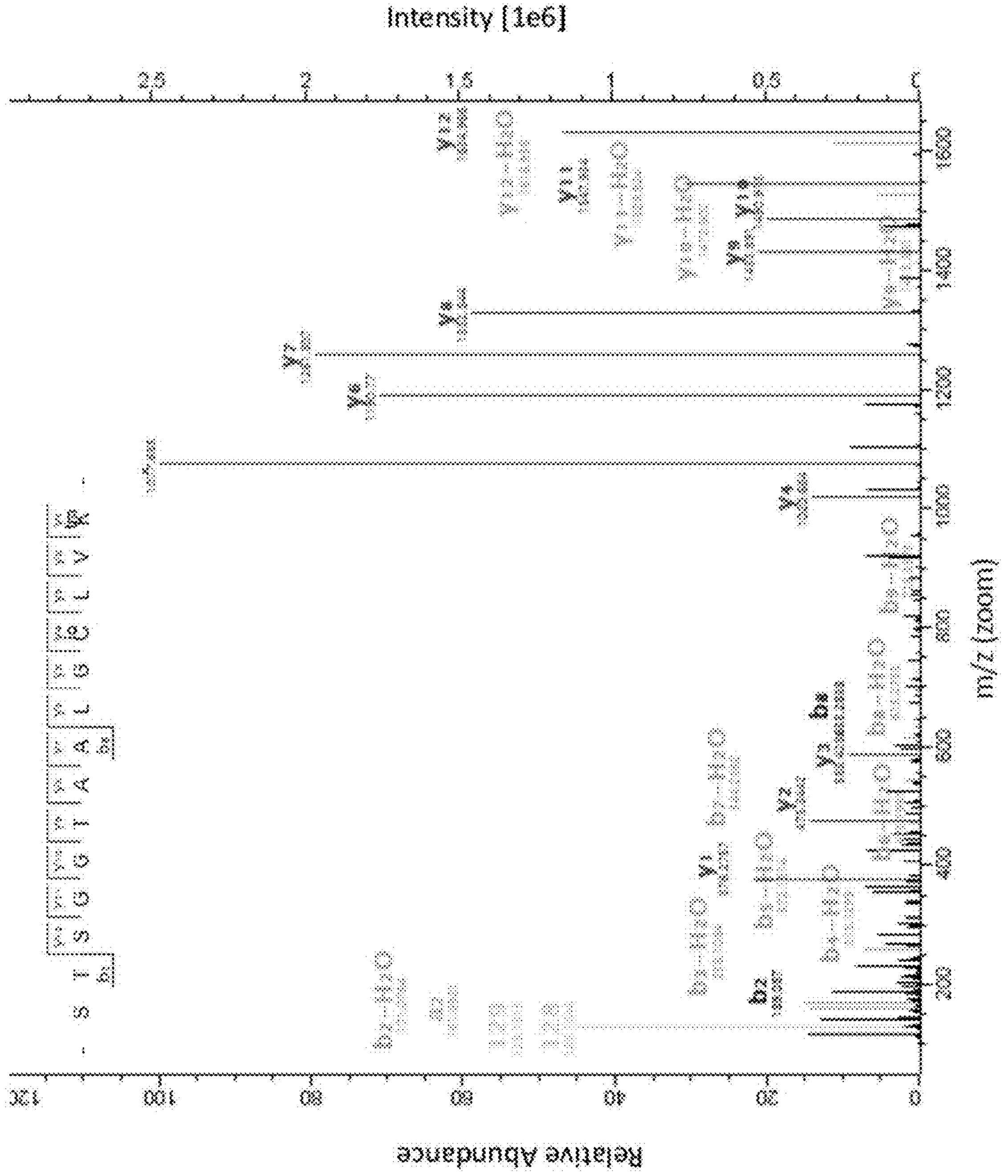

In another embodiment, three different types of reporter barcodes are used to calculate the drug occupancy at each cysteine residue. FIG. 5A shows HCD-$MS^2$ spectra of a dual TMT labeled isobaric peptide of NIST mAb light chain. The peptide has an unoccupied cysteine residue labeled with iodoTMT (io) and the N-terminus and terminal lysine residue labeled with TMT (tm). The HCD spectrum (left side panel) consists of a series of characteristic b and y type backbone product ions that localize the labeling sites with the corresponding TMT label. The lower mass range shows four reporter ions, which are more clearly depicted in the enlarged right side panel, including the reporter ions masses for each dual TMT channel, i.e., the iodoTMT-129 and TMT-128 pair representing the mock channels and the iodoTMT-126 and TMT-130 pair representing the conjugate sample channels. The occupancy can be derived by either the IodoTMT intensities of the mock (A2) and conjugate (A1) or using the TMT intensities of mock (B2) and conjugate (B1). The HCD spectrum provides both sequence ions and in spectral ratios to identify the site conjugation at light chain Cys-193 with Biotin PEO acetamide at an occupancy of ~50%. Similarly, occupancies can be obtained for a given reaction condition for the conjugate production. For example, FIG. 5B shows the reporter ion regions of two additional sites; light chain Cys-63 with Biotin PEO acetamide occupancy of ~65% and heavy chain Cys-147 with Biotin PEO acetamide occupancy of ~100%, and FIGS. 5C and 5D show the corresponding $MS^2$ spectra (with all backbone product ions) of the peptides sequenced by HCD-$MS^2$.

Figure 6A:
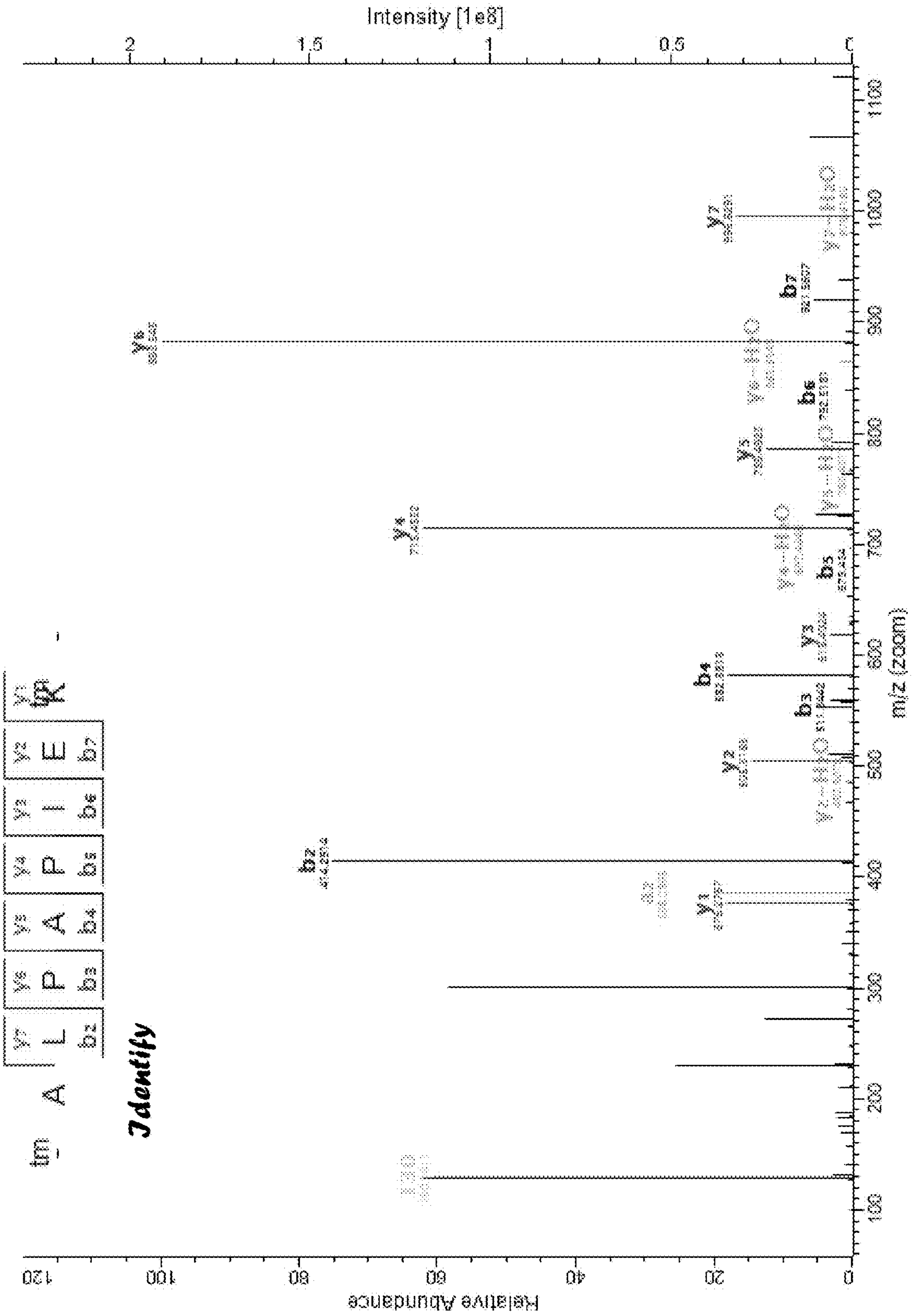
FIGS. 6A and 6B illustrate an embodiment of the application using TMTs for normalizing mixing ratios of NIST mAbs by performing HCD-$MS^2$ across reaction conditions with non-cysteine peptides, although other $MS^2$ such as ETD-$MS^2$, can also be used, and using the Normalization Ratio shown in formula to correct for mixing or digestion biases between ADC (NIST mAb-Biotin-PEO acetamide) containing sample (Sample) and the unconjugated sample (Mock)
Figure 6B:
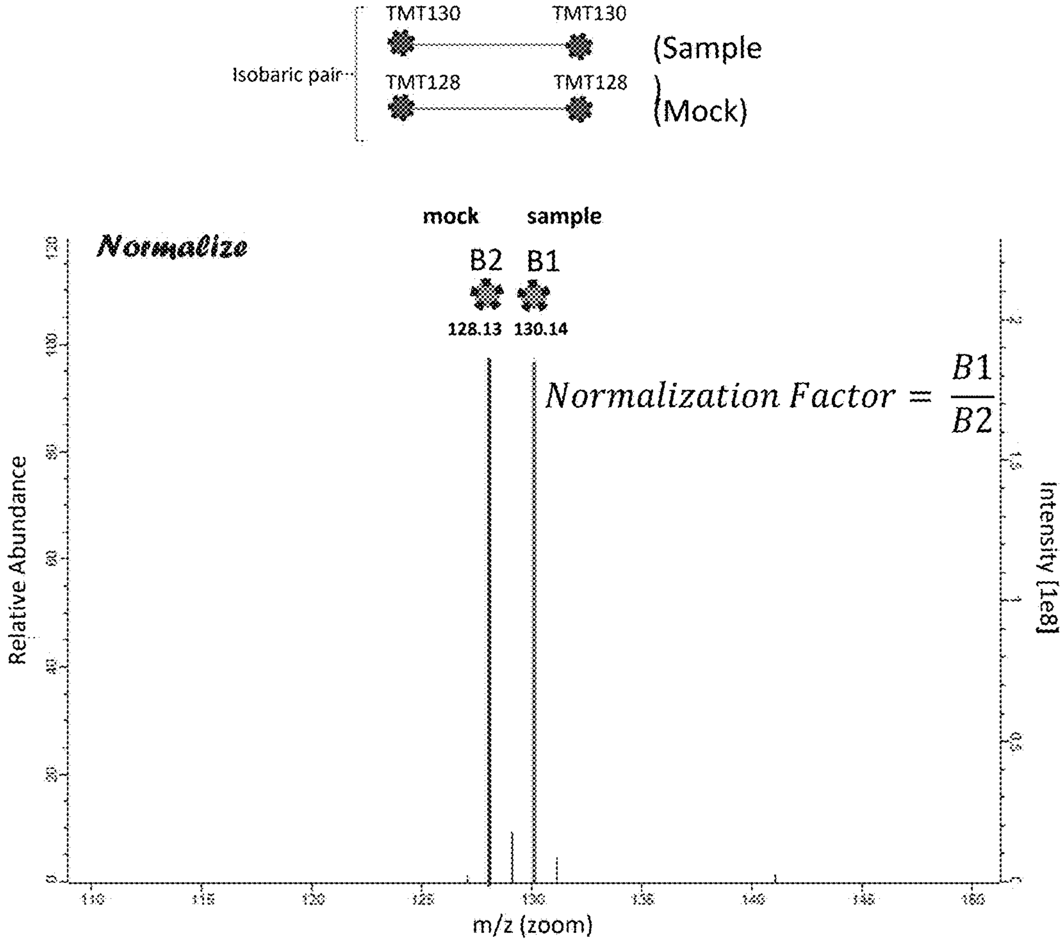

The dual-TMT workflow uses the normalization factor between the conjugate and mock samples to correct for deviations in occupancy estimates. For example, FIGS. 6A and 6B show HCD-$MS^2$ spectra of a dual TMT labeled isobaric peptide of NIST mAb heavy chain. The N-terminus and C-terminus lysine of the peptide is labeled with TMT. The HCD spectrum (FIG. 6A) consists of a series of characteristic b and y type backbone product ions that localize the TMT labeling sites. The lower mass range shows two reporter ions; and the reporter ions TMT-128, TMT-130 pair (FIG. 6B) represent the mock and conjugate sample channels respectively. Peptides that lack cysteine residues exhibit such characteristic mass barcode of two reporter ions where the reporter ion intensities represent the concentrations of mock and conjugate samples. Typically, a ratio of 1 is observed for such non-cysteine peptides that are completely labeled.

Figure 7:
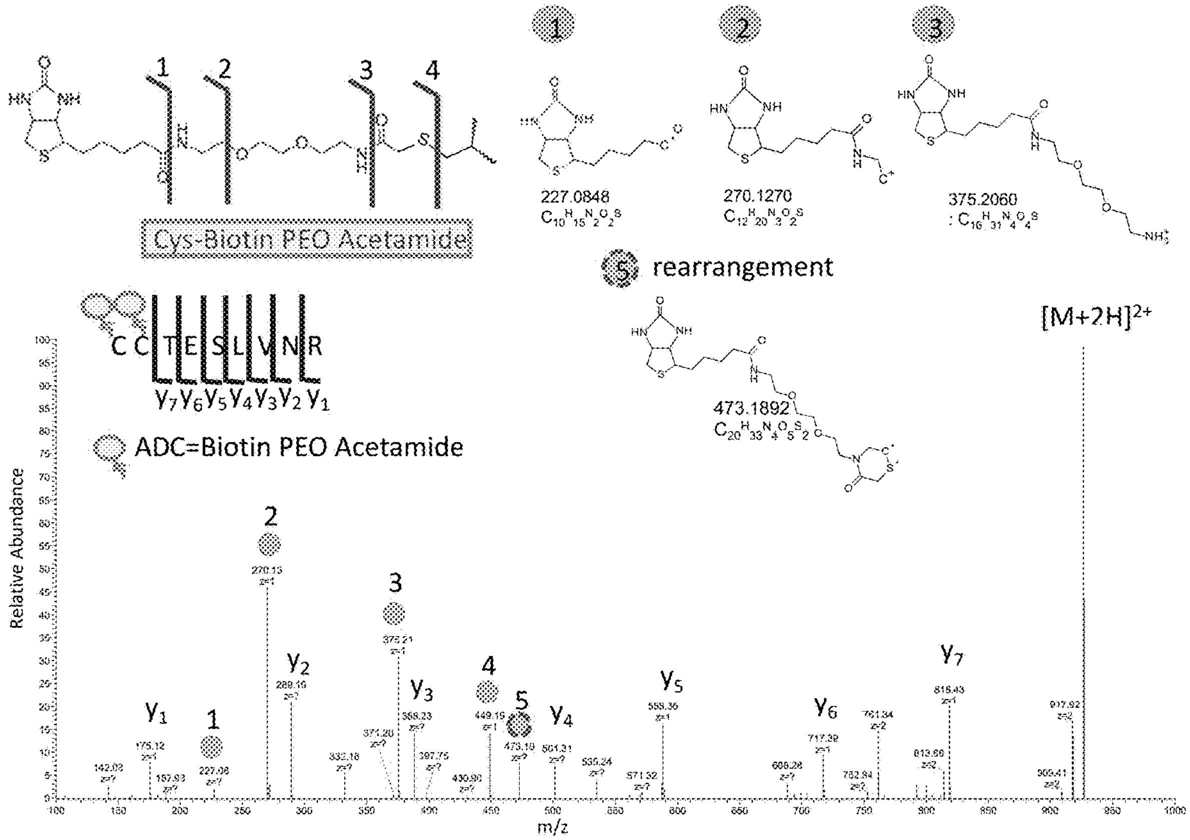
FIG. 7 shows the HCD-$MS^2$ product ion spectrum that contains backbone fragmentation of peptide consisting of the drug and also fragments corresponding to the fragmentation of biotin PEO acetamide molecule using a method according to an embodiment of the application as well as the analysis using ETD-$MS^2$: note small molecule conjugates prone to fragmentation produced complex spectra, and the fragment masses from the drug are specific for each drug.

In another embodiment, the sequence ions and immonium ions of corresponding drug fragments aid in determining site of occupancy of the conjugated peptide (see, e.g., FIG. 7). It is difficult to determine site localization using conventional methods when multiple potential conjugation sites are present on the same peptide. Sequence ions specific to the site are often absent and the localization of the peptide is challenging to determine when the mass to charge ratio of the peptide sequence is indistinguishable. Consequently, determining the precise localization of conjugated sites often requires site-specific sequence ions that are obtained by additional complementary dissociation methods known in the art. For example, ETD-MS2 is complementary to HCD-MS2. One can use two methods to create sequence ions, which can make the sites distinguishable or in other words localize the modified residue. For example, drug conjugated cysteine can be localized from unconjugated cysteines. Methods accordingly to embodiments of the application allow one to determine the site of occupancy of the conjugated peptide, including those with multiple conjugation sites, without using the complementary dissociation methods. For example, dissociation can be done to identify and localize the payload.

Figure 8A:
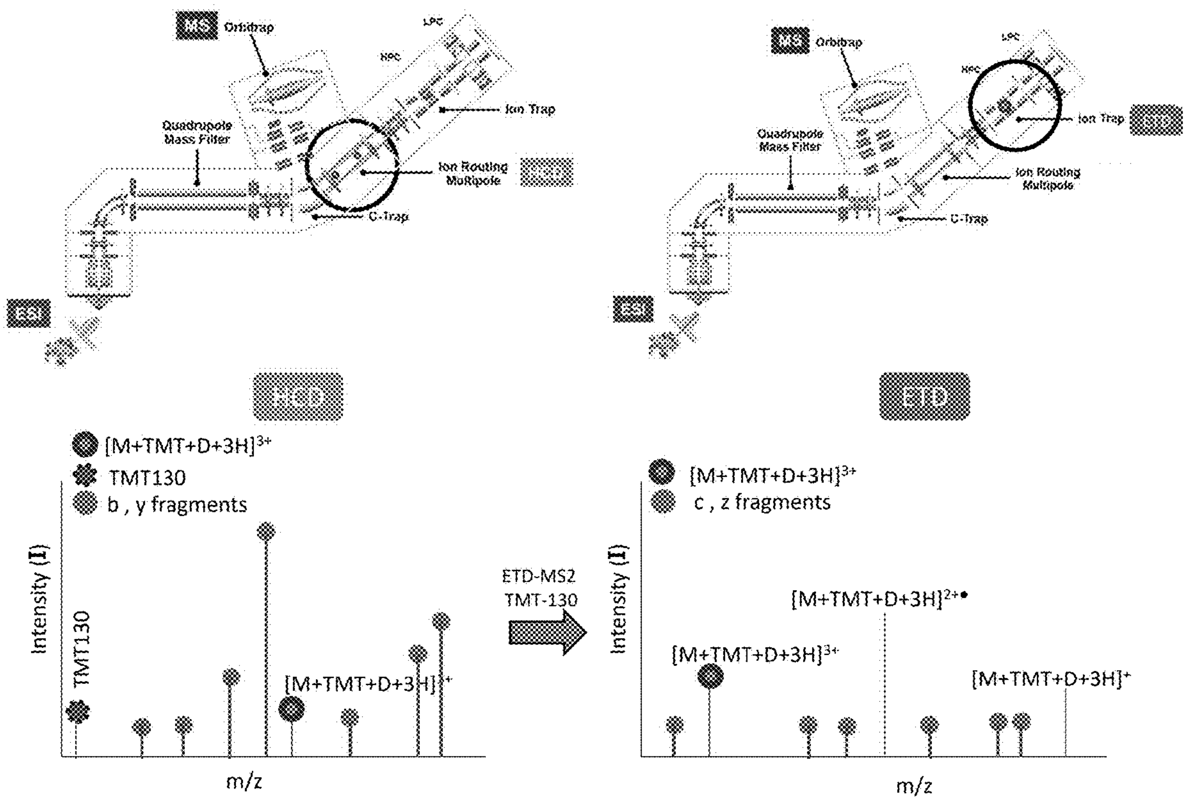
FIG. 8A illustrates TMT-130 reporter triggering for NIST triple play workflow.
Figure 8B:
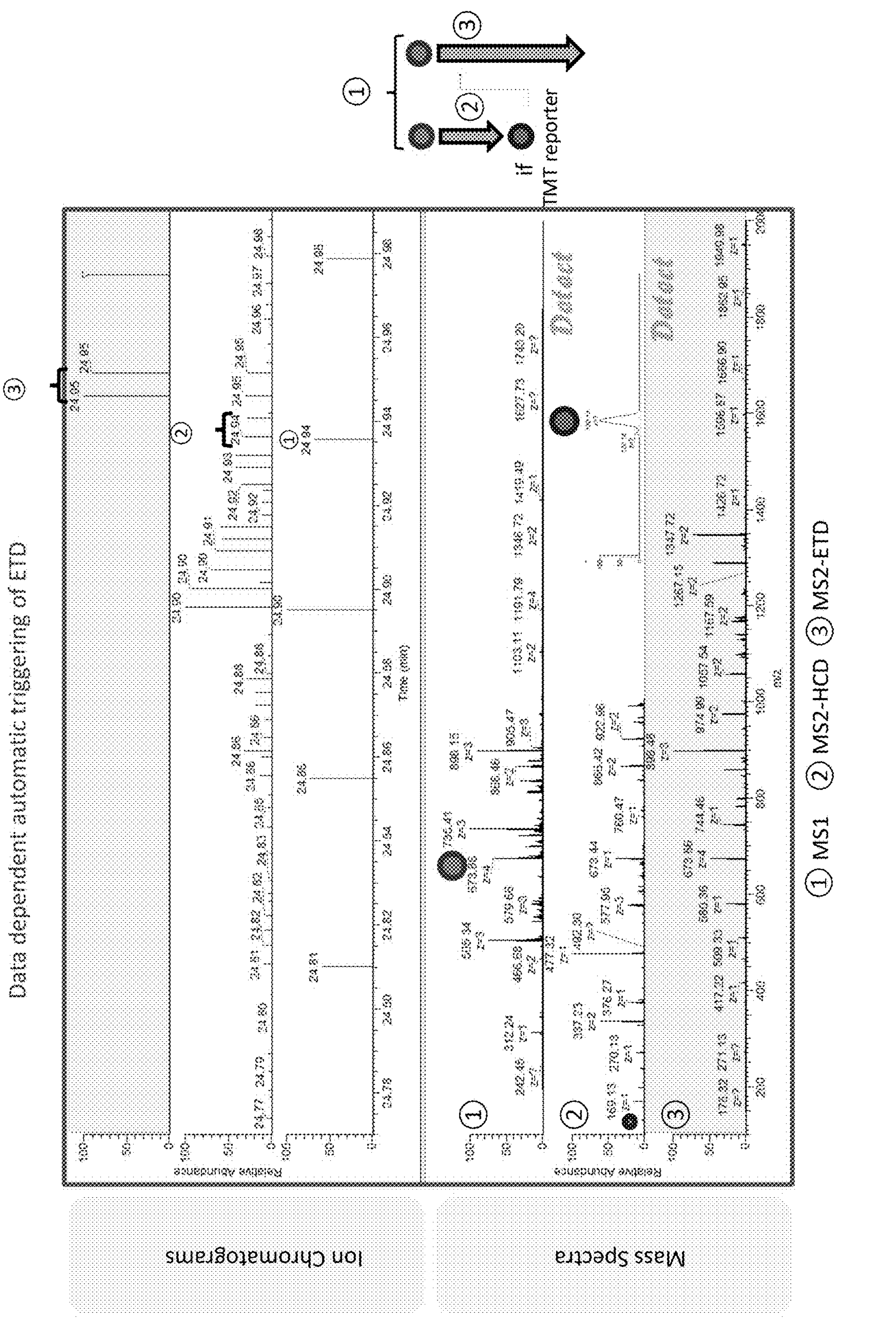
FIG. 8B shows using TMT-130 signature ion (Barcode) to trigger ETD-$MS^2$ to localize the conjugated drug using a method according to an embodiment of the application and the observed total ion chromatograms (TIC)

Methods of the application can further include steps to improve the mass triggering, quantification sensitivity, and accuracy using methods known in the art in view of the present disclosure. For example, HCD-$MS^2$ can be performed on a mass selected precursor ion of a TMT labeled peptide conjugate in an ion-routing multipole (see, e.g., FIGS. 8A and 8B). The produced ions spectrum is acquired in the Orbitrap where TMT reporter ions are detected. A reporter ion mass (130.14 Da in FIG. 8A) can be used as a trigger mass selection of same precursor ions and transfer to the ion trap. Subsequently, ETD-$MS^2$ is performed in the ion trap and the resulting product ions are mass analyzed in the Orbitrap. For example, FIG. 8B demonstrates the TICs and corresponding mass spectra for data-dependent scans that occur sequentially from MS, $MS^2$, and triggered $MS^2$ of the NIST light chain cys-193 Biotin PEO acetamide conjugate peptide. The TIC labeled 1 is the full MS scan collected in the Orbitrap. TIC labeled 2 is the HCD-$MS^2$ of the mass selected precursor ion which is acquired in the Orbitrap in two consecutive scans and TIC labeled 3 is the TMT-130 triggered ETD-$MS^2$ spectrum that is obtained within the same scan cycle and mass analyzed in the Orbitrap. The time penalty incurred for high resolution Orbitrap mass analysis sequence for both $MS^2$ product ion spectra likely does not impact the relatively small subset of drug conjugate peptides.

Figure 9A:
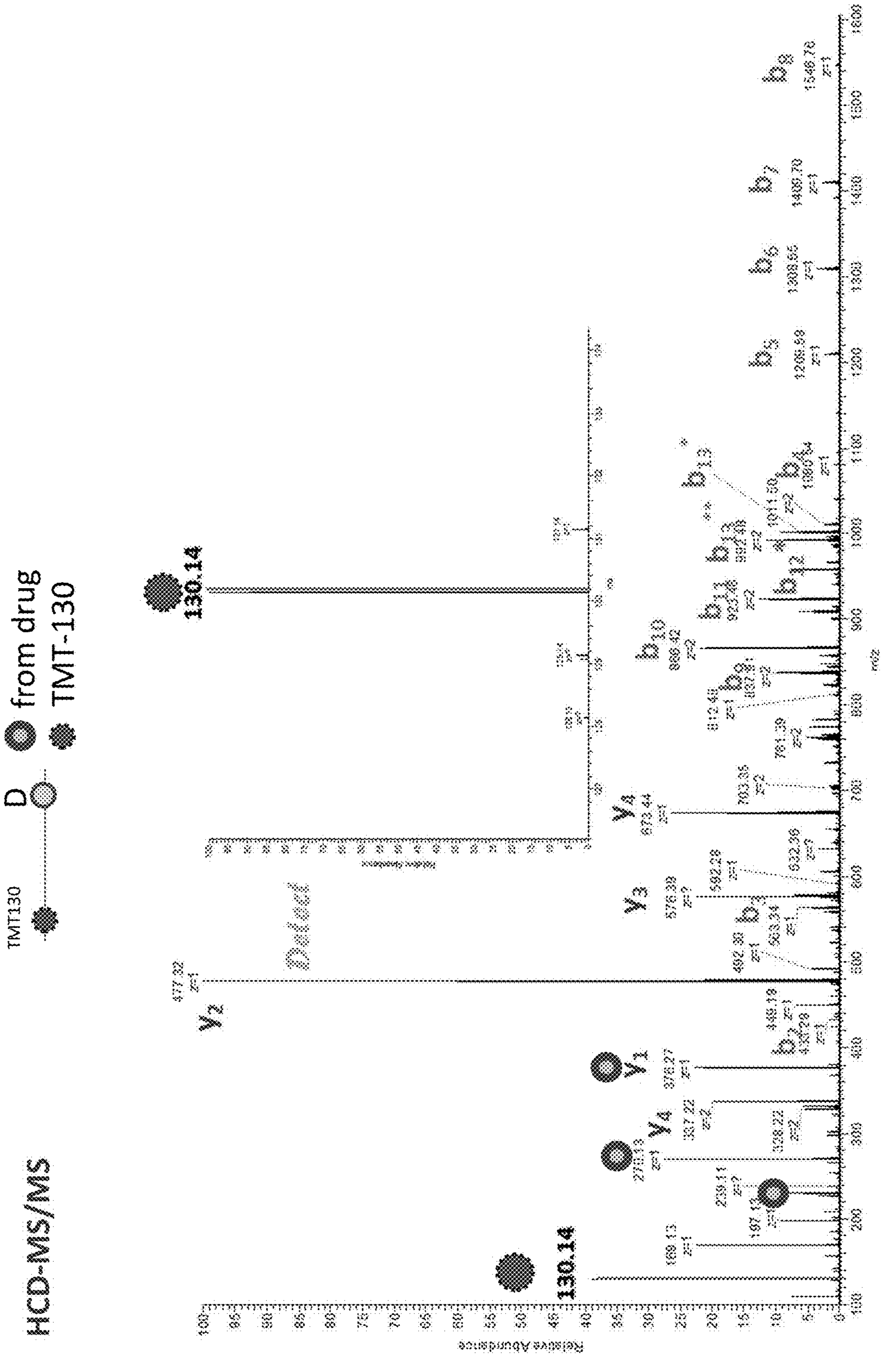
FIGS. 9A&9B illustrate localizing biotin PEO acetamide via mass triggerring of TMT-130 using a method according to an embodiment of the application: TMT-130 from HCD-$MS^2$ is unique and triggering is agnostic of the type of ADC, and the ETD-$MS^2$ localized the drug with no fragmentation of the drug; D=Biotin-PEO acetamide
Figure 9B:
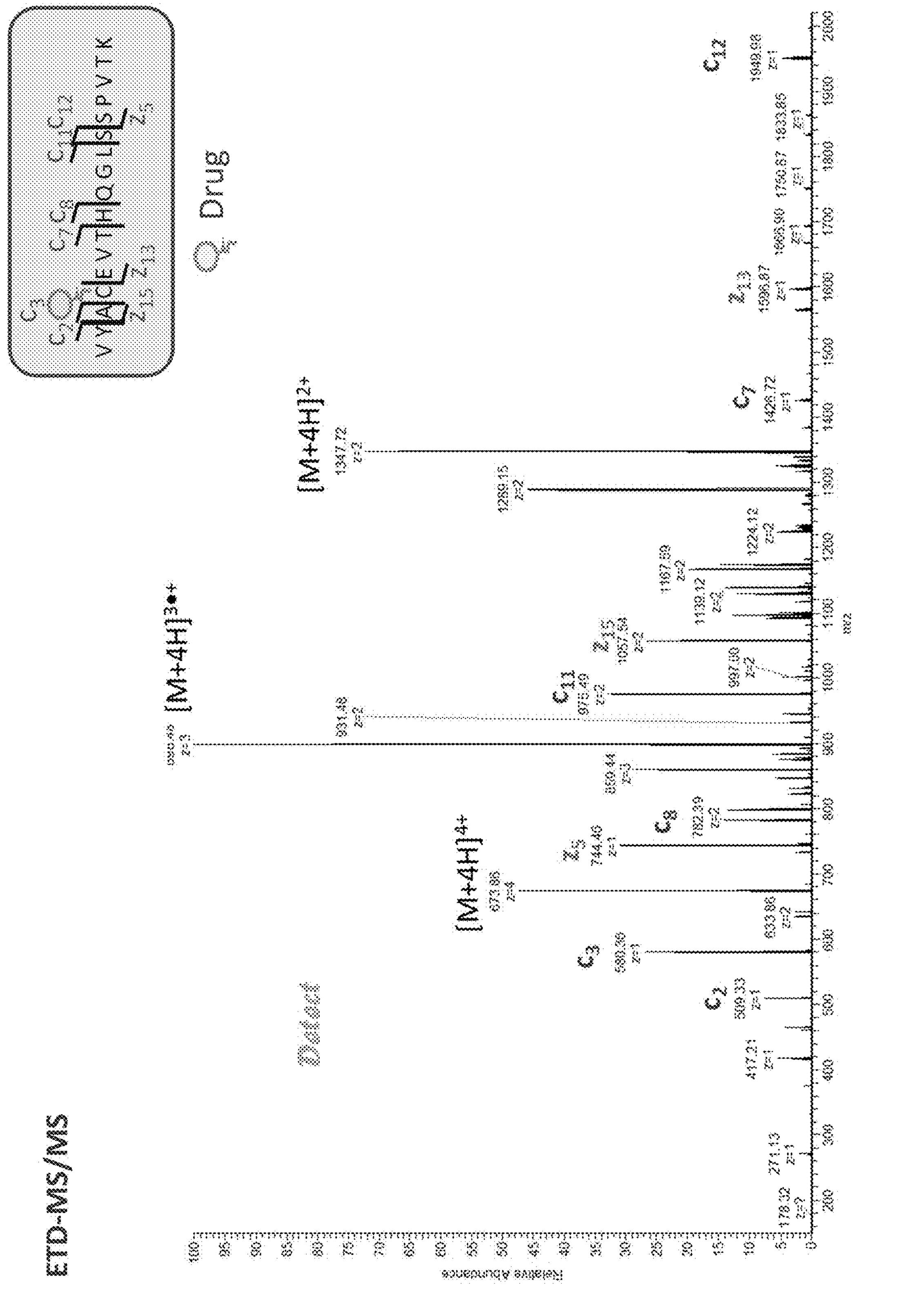
Figure 9C:
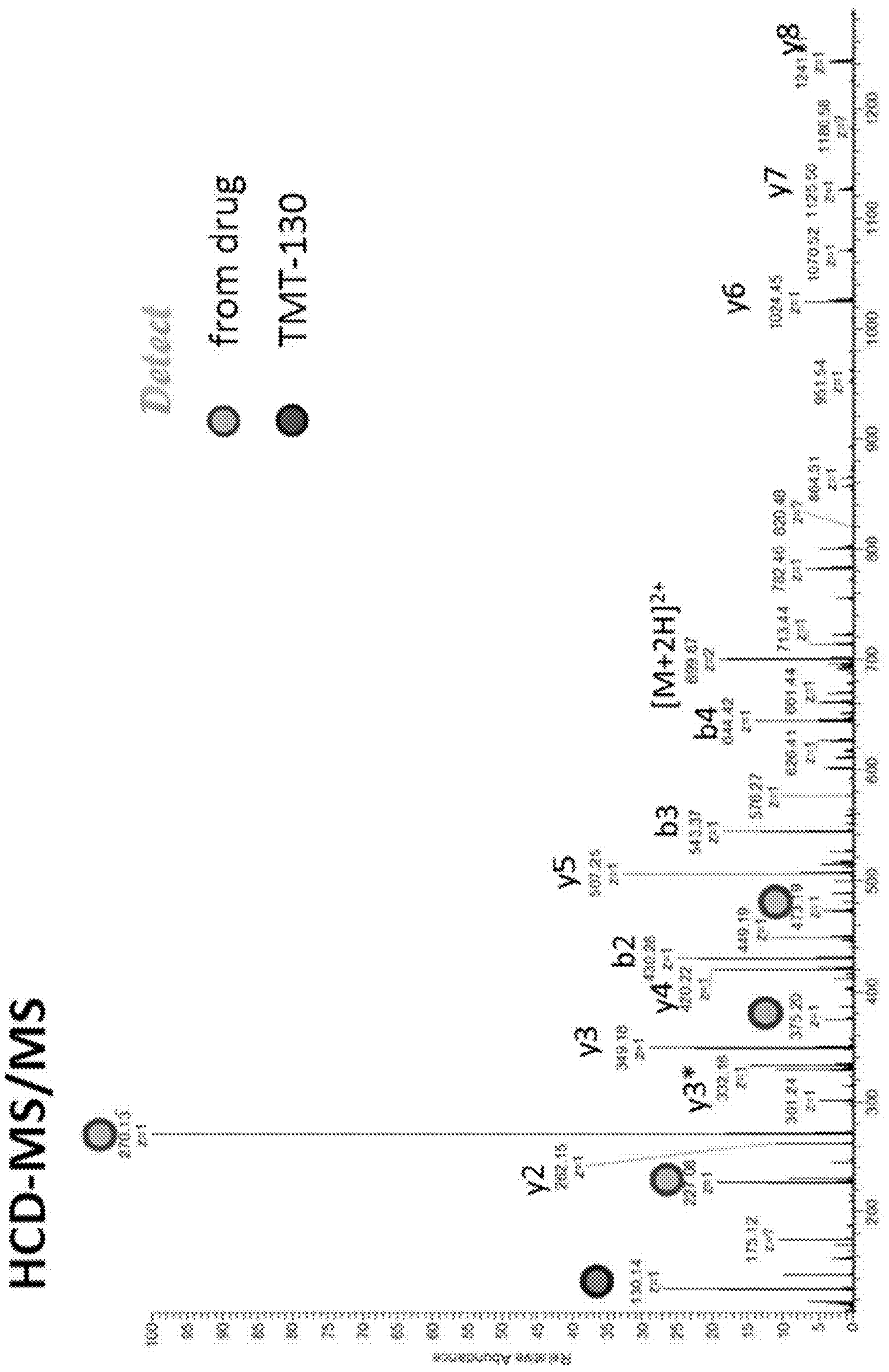
FIGS. 9C&9D show the triggered mass detection of the peptide corresponding to biotin PEO acetamide conjugated at Cys-23 where TMT130 was less abundant compared to immonium ions produced by biotin PEO acetamide.
Figure 9D:
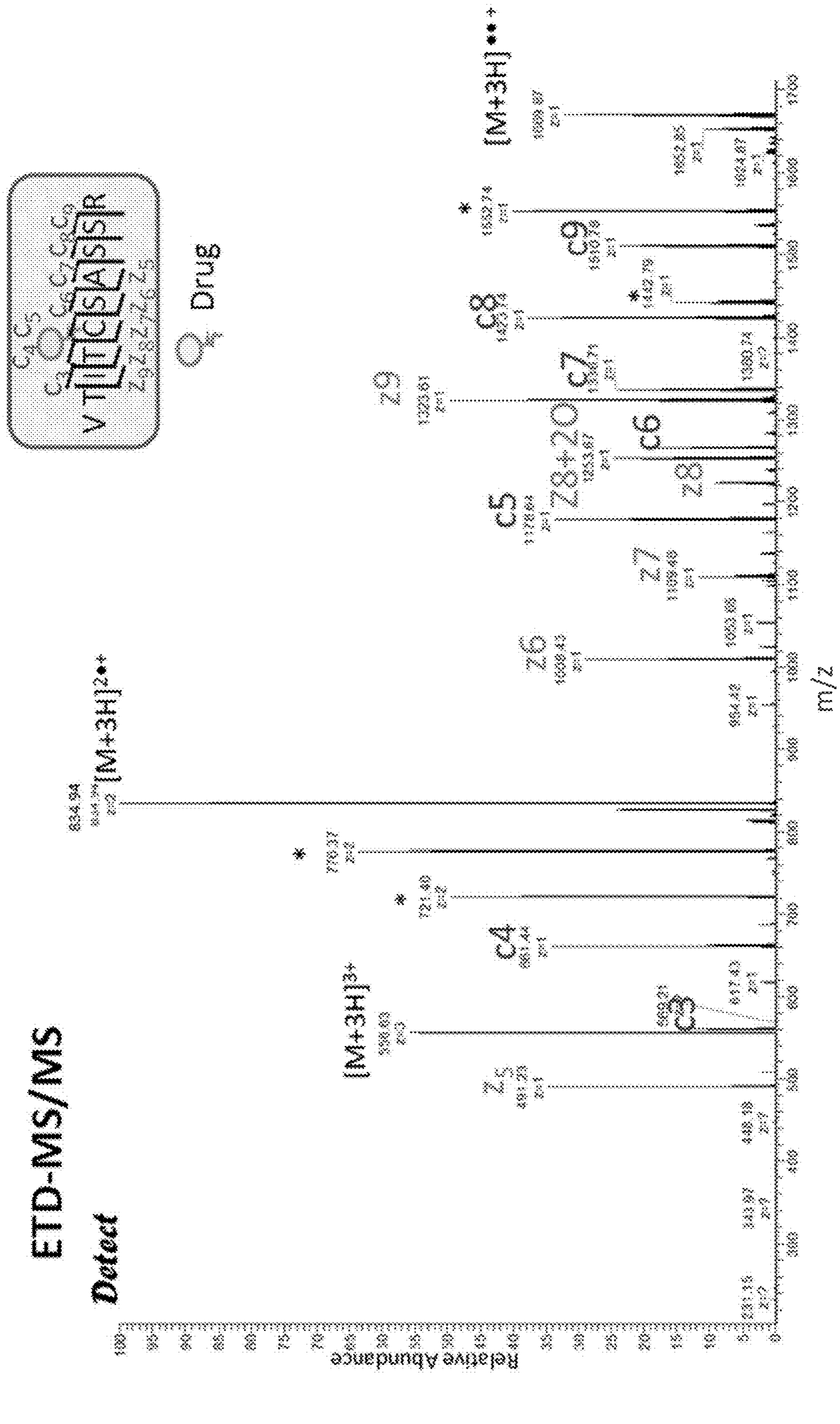

Charge-loss ion generated by HCD-MS2, such as the reporter ion TMT-130, can be used to trigger ETD-MS2 and generate an ETD spectrum. FIGS. 9A and 9B show the annotated HCD and ETD spectra for Cys-193 Biotin PEO acetamide conjugate peptide, respectively. It is important to note a highly selective TMT130 ion and immonium ions from the drug are readily observed in the spectra. In addition, characteristic neutral loss of the reporter and the entire tag were observed in the ETD spectra, shown with asterisks in FIGS. 9B and 9D. The backbone fragments from both ETD and HCD are complementary and localize Biotin PEO acetamide on Cys-193. TMT130 is shown to be a useful immonium ion, despite not being the most abundant immonium ion. For example, FIGS. 9C and 9D show the triggered mass detection of the peptide corresponding Biotin PEO acetamide conjugated at Cys-23, where TMT130 was less abundant compared to immonium ions produced by Biotin PEO acetamide. The specificity of generating TMT130 mass trigger can also be controlled for interfering peptides by reducing the mass selection window of the precursor ion.

Figure 10A:
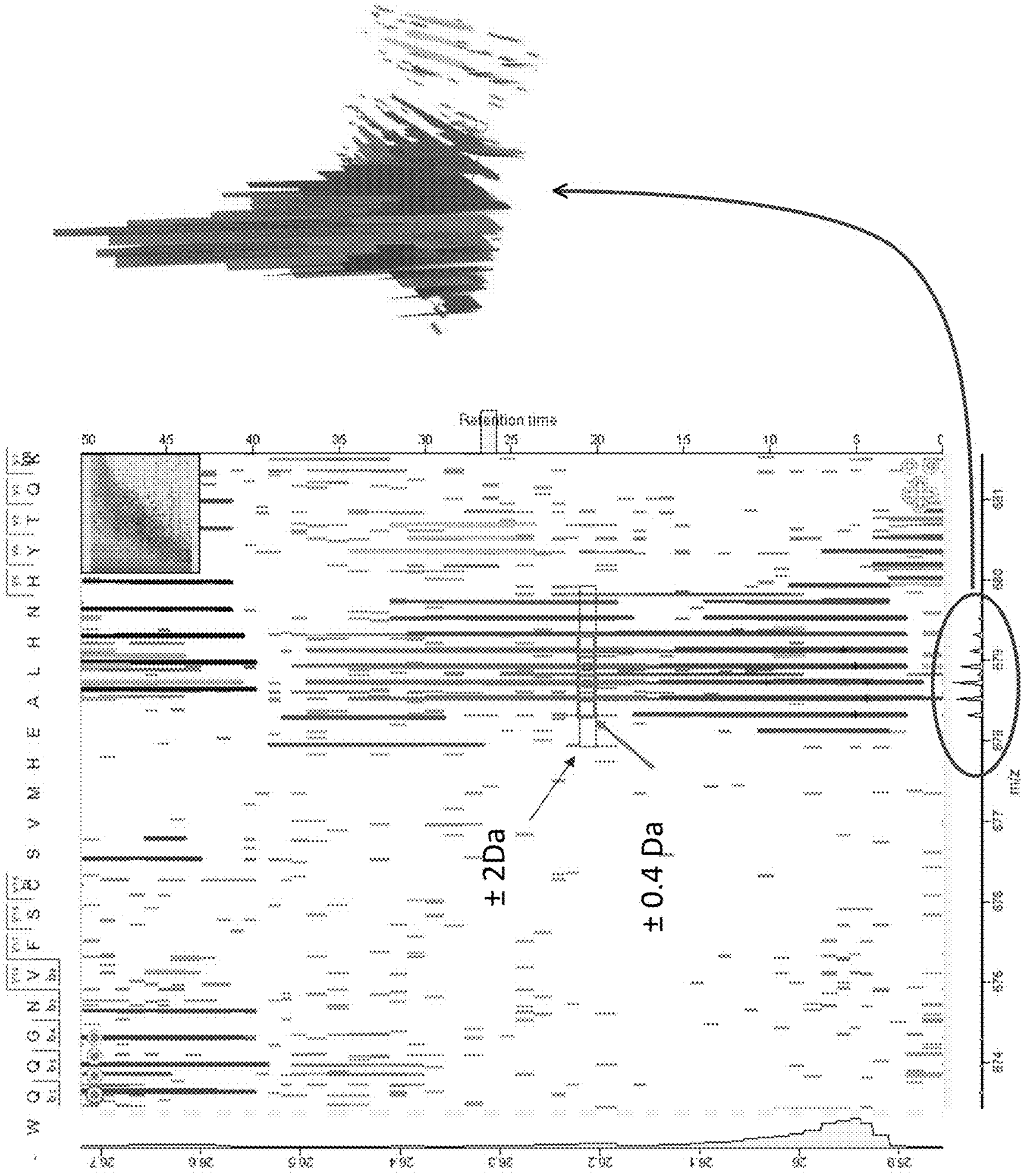
FIGS. 10A&10B show a method of improving specificity of triggerring TMT-130 according to an embodiment of the application: co-isolation and co-fragmentation of peptides resulted in loss of specificity of TMT-130, and higher trigger intensity thresholds or narrow isolation windows resulted in improved mass triggering.
Figure 10B:
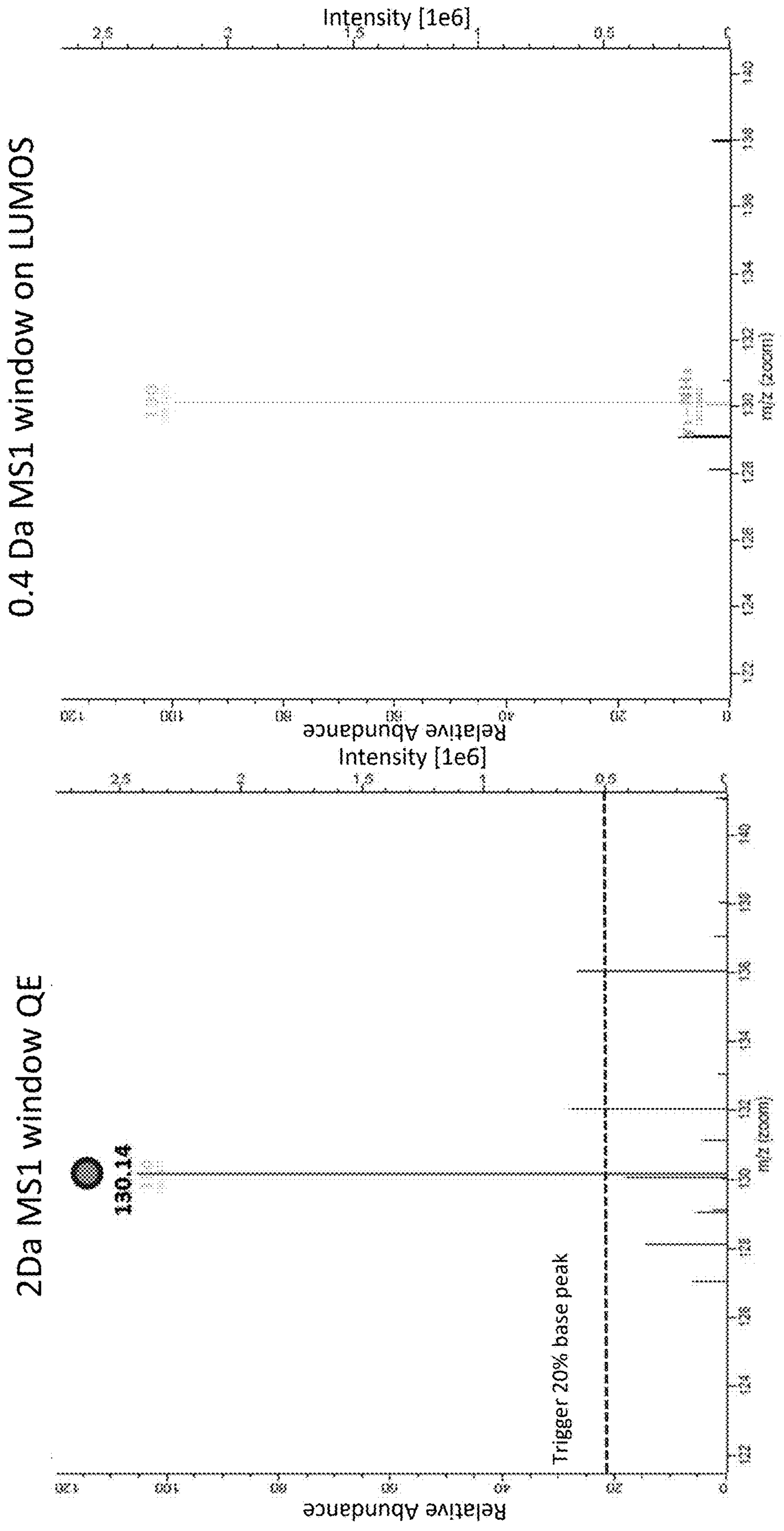

For example, co-isolation and co-fragmentation of peptides can result in loss of specificity of the reporting ion of TMT-130 that serves to trigger the ETD-$MS^2$ analysis on the ADC-peptide to localize the conjugation site on the polypeptide. Higher trigger intensity thresholds or narrow isolation windows (e.g., 0.4 Da) can be used to improve the mass triggering (see, e.g., FIGS. 10A and 10B). Various reporter ions can affect the barcode type for triggering, particularly where co-isolation occur and co-fragmentation occur due to peptides that co-elute with the same isolation window size (e.g., 2 Da) (FIG. 10B).

Figure 11:
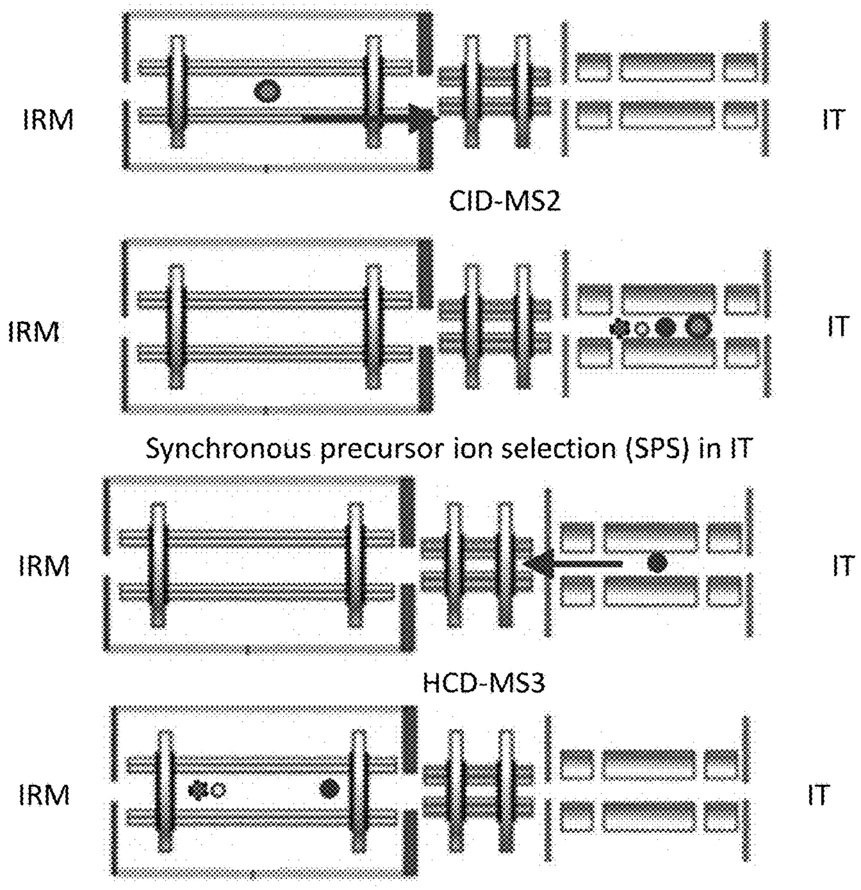
FIG. 11 illustrates how Sample Prep Station (SPS-3) is used for isobaric labeling experiments according to an embodiment of the application, wherein the precursor ions are transferred from Ion Routing Multipole (IRM) to Ion trap (IT), and synchronous precursor selection (SPS) is conducted in IT.

In another embodiment, SPS-$MS^3$ can be used to further improve specificity and accuracy of the detection and quantification (see, e.g., FIG. 11). Precursor ions are dissociated by collision induced dissociation (CID) in an ion trap and several product ion masses are synchronously isolated using a notch wave form that is applied to the ion trap. The isolated product ions are transferred to an ion routing multipole where HCD-$MS^3$ fragmentation is performed. Due to the SPS, any interferences due to co-fragmentation during standard HCD is mitigated, which results in reporter ions with few to no interferences.

Figure 12A:
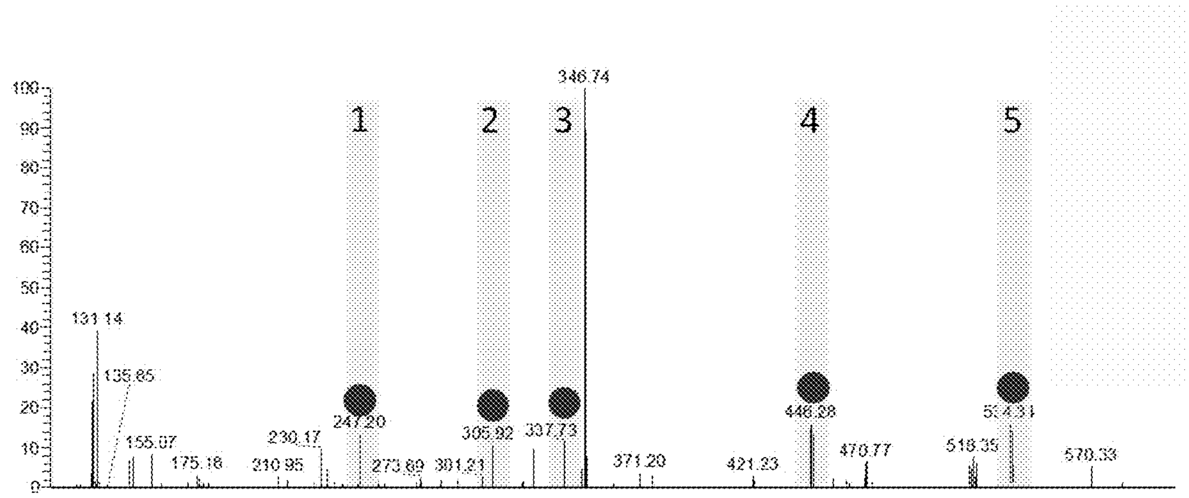
FIGS. 12A-C show the improved specificity and accuracy of TMT quantification using synchronous precursor selection according to an embodiment of the application.
Figure 12B:
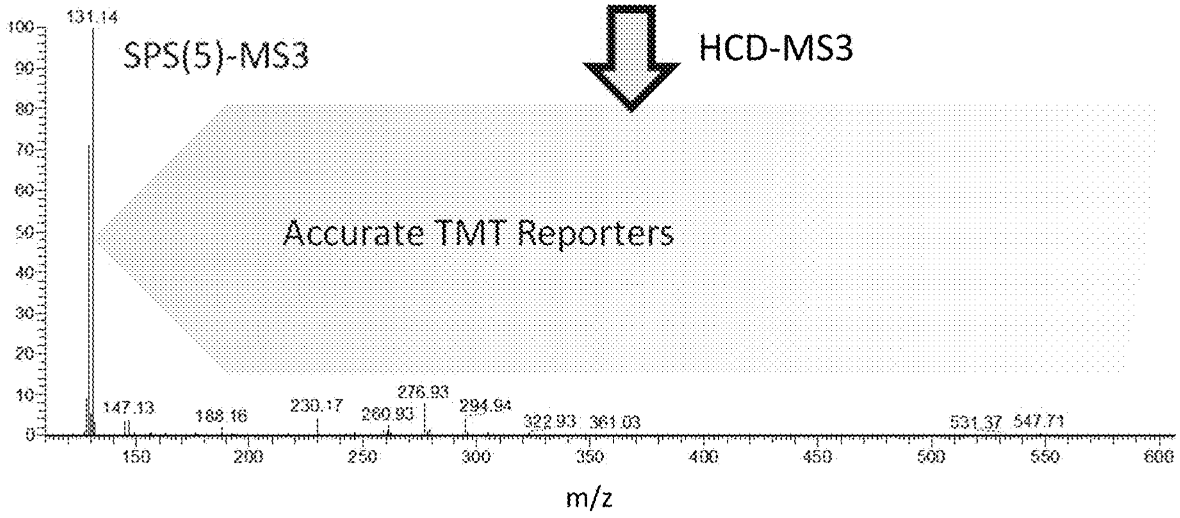
Figure 12C:
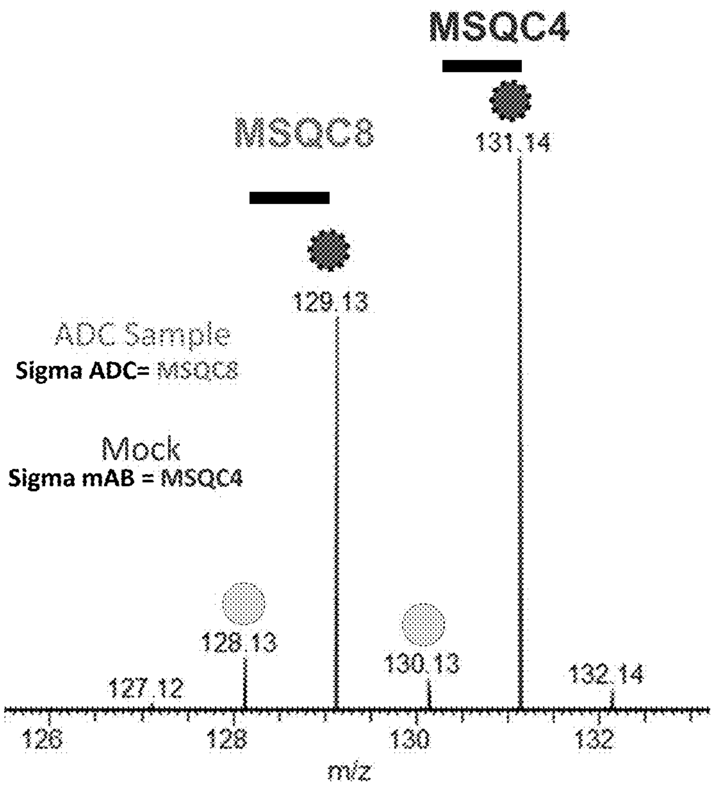

For example, synchronous precursor selection was used in reporter quantification of a study on the ADC of MSQC8 having the structure shown in FIG. 4 and its mock control MSQC4, the antibody without the conjugated drug using a method according to an embodiment of the application. As shown in FIGS. 12A-C, the application of synchronous precursor selection allowed accurate TMT reporting, which improved quantification sensitivity and accuracy. Accurate reporter ion ratios were observed after SPS-$MS^3$ using N=5 ions with iodoTMT-128, TMT-129 reporter ion pair representing MSQC8 and iodoTMT-130, TMT-131 reporter ion pair representing MSQC4 (mock). The reporter ion ratio for MSQC8:MSQC4 was 1, indicative that the cysteine residue was unconjugated.

Figure 13A:
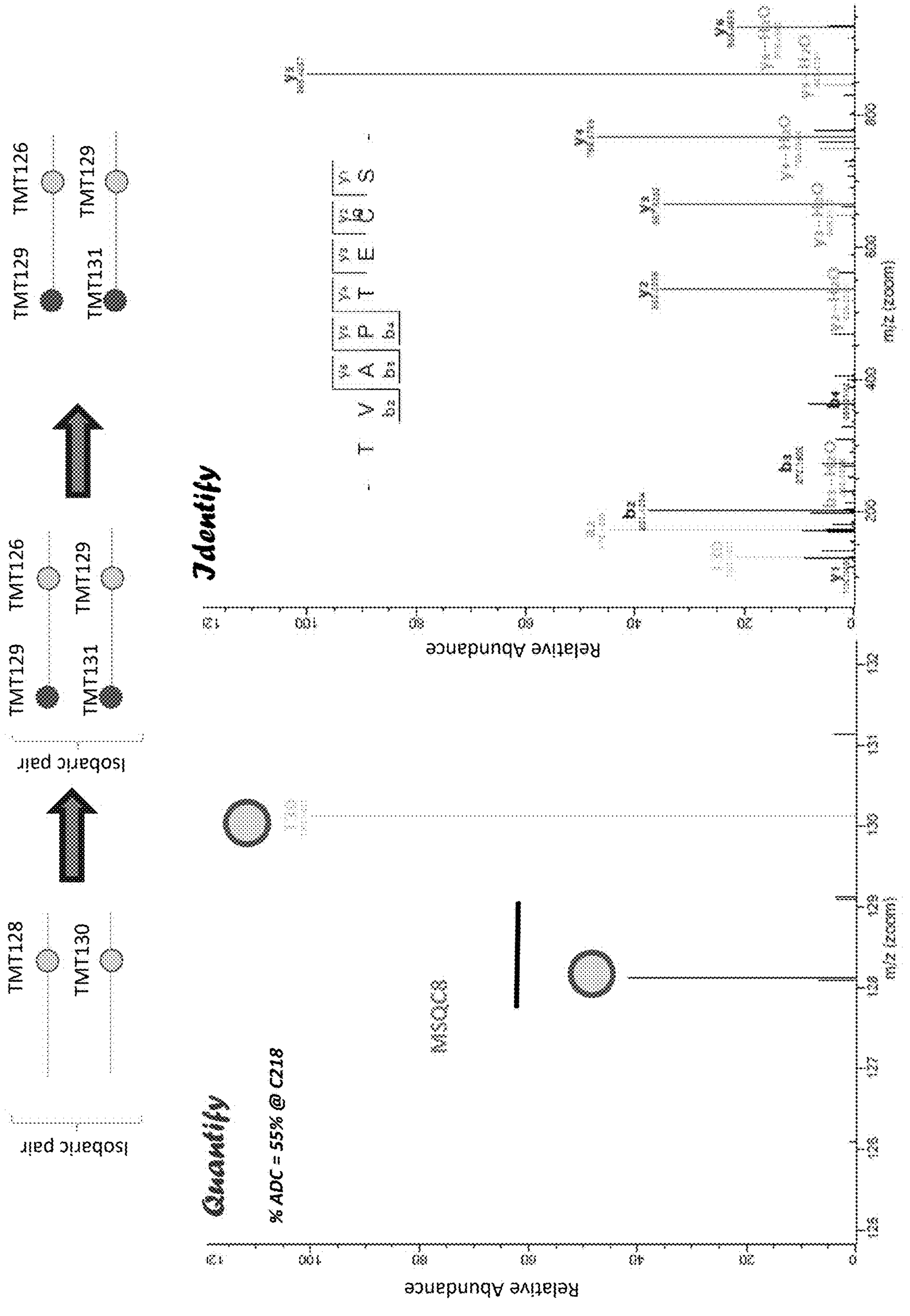
FIGS. 13A to 13F illustrate the experiments and results of using dual TMTs for quantifying site-specific ADC (dansyl fluorophore) on MSQC8 (mAb antibody-drug conjugate mimic) using a method according to an embodiment of the application, including the MS-based bar codes for site-specific conjugation occupancies.
Figure 13B:
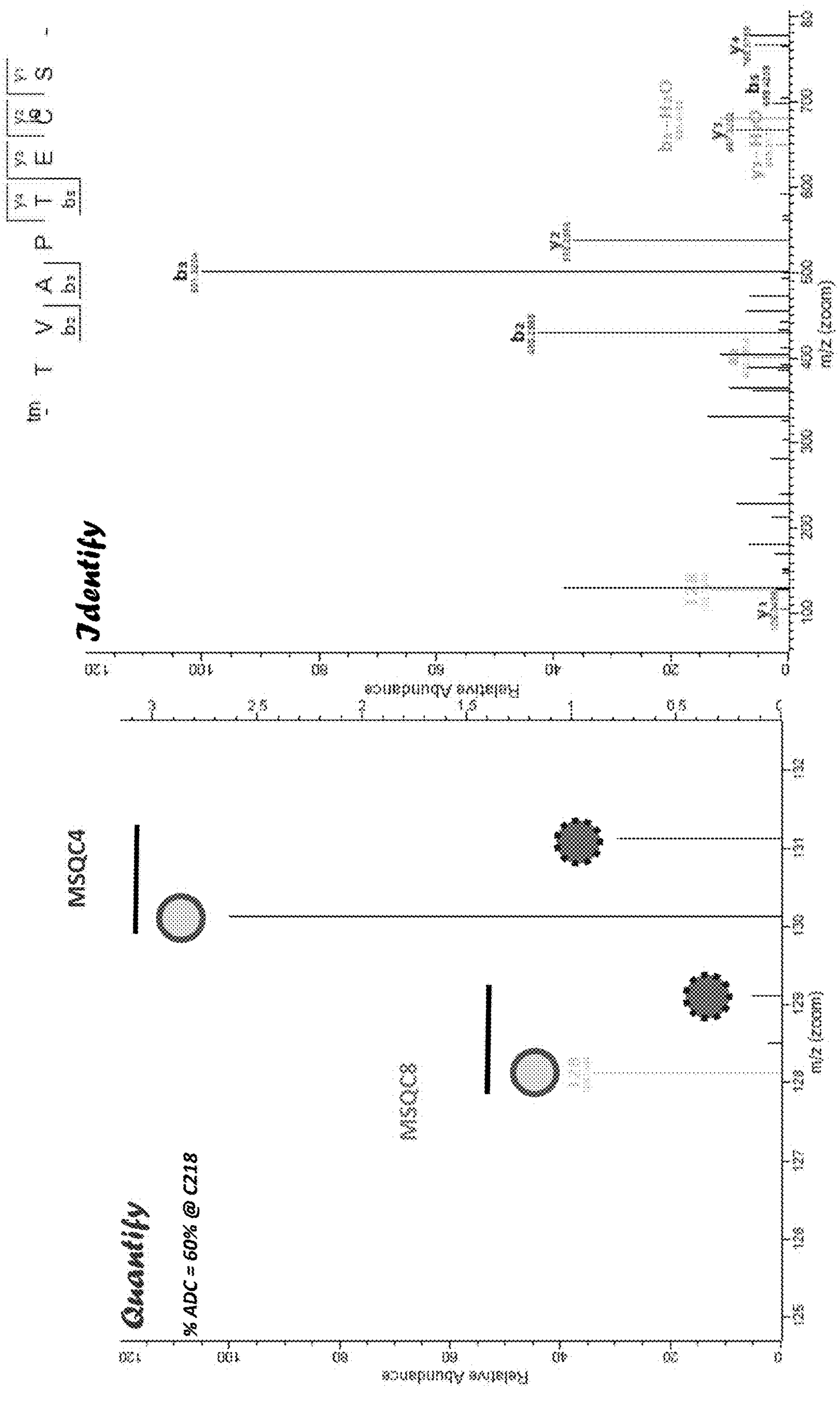
Figure 13C:
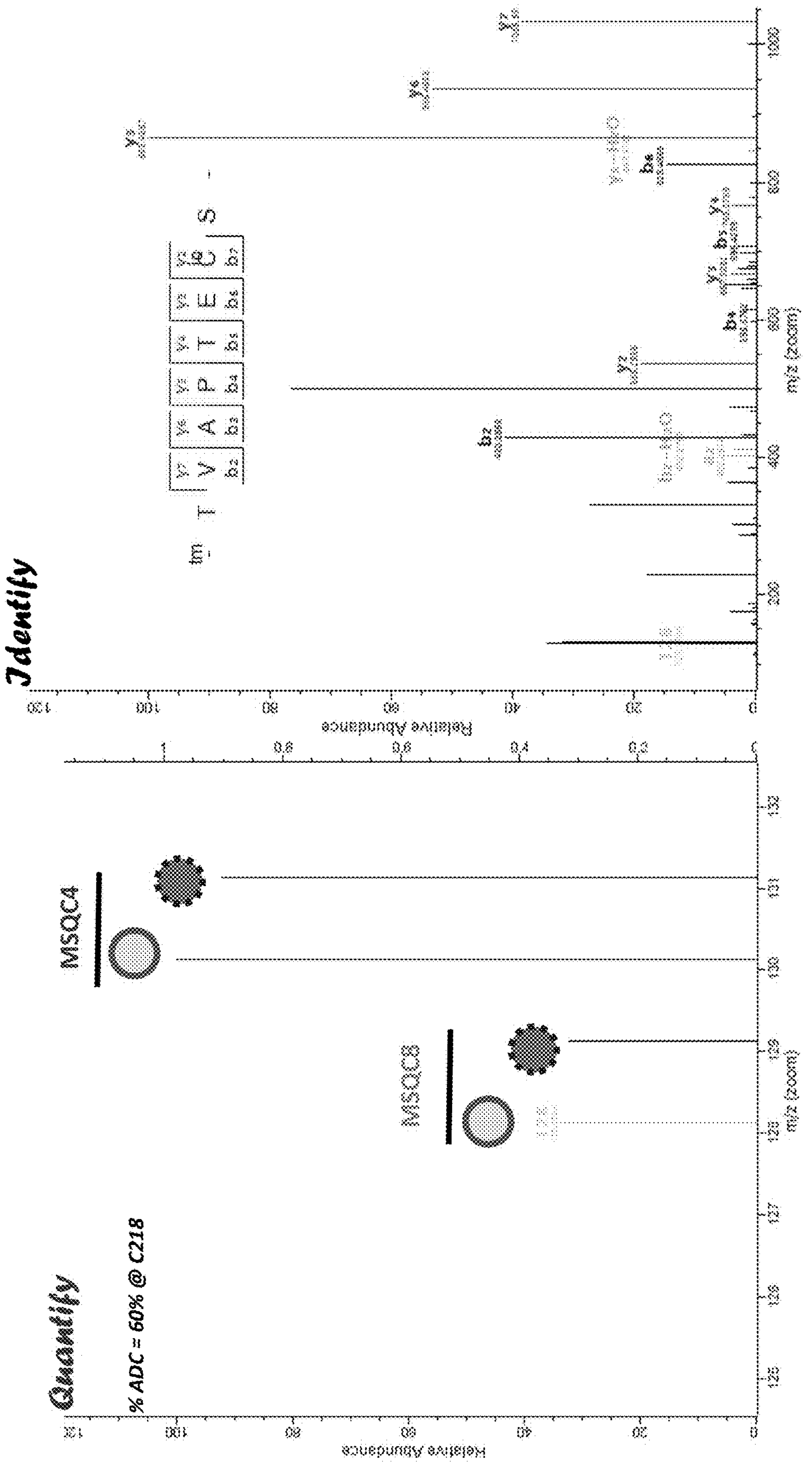
Figure 13D:
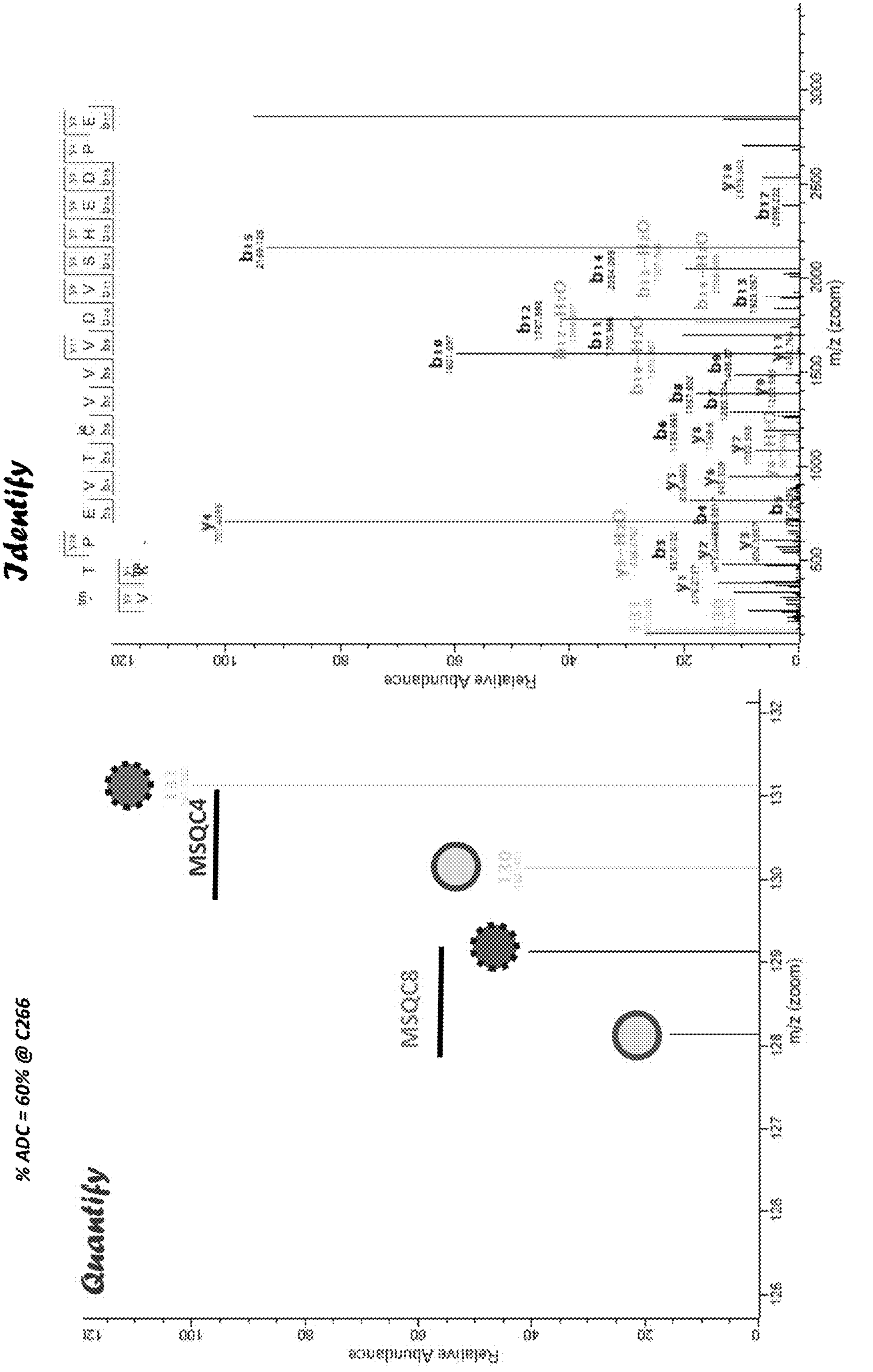
Figure 13E:
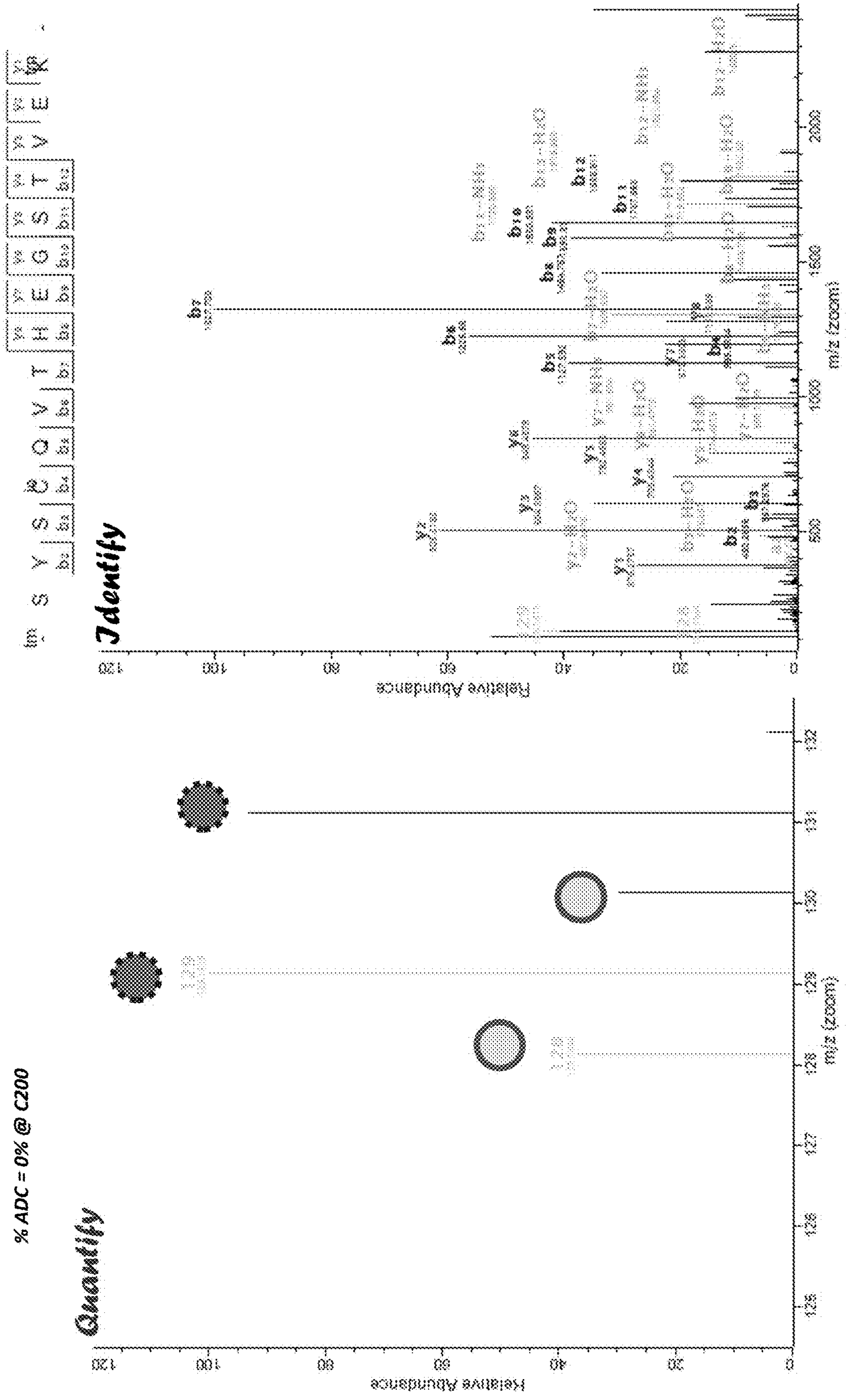
Figure 13F:
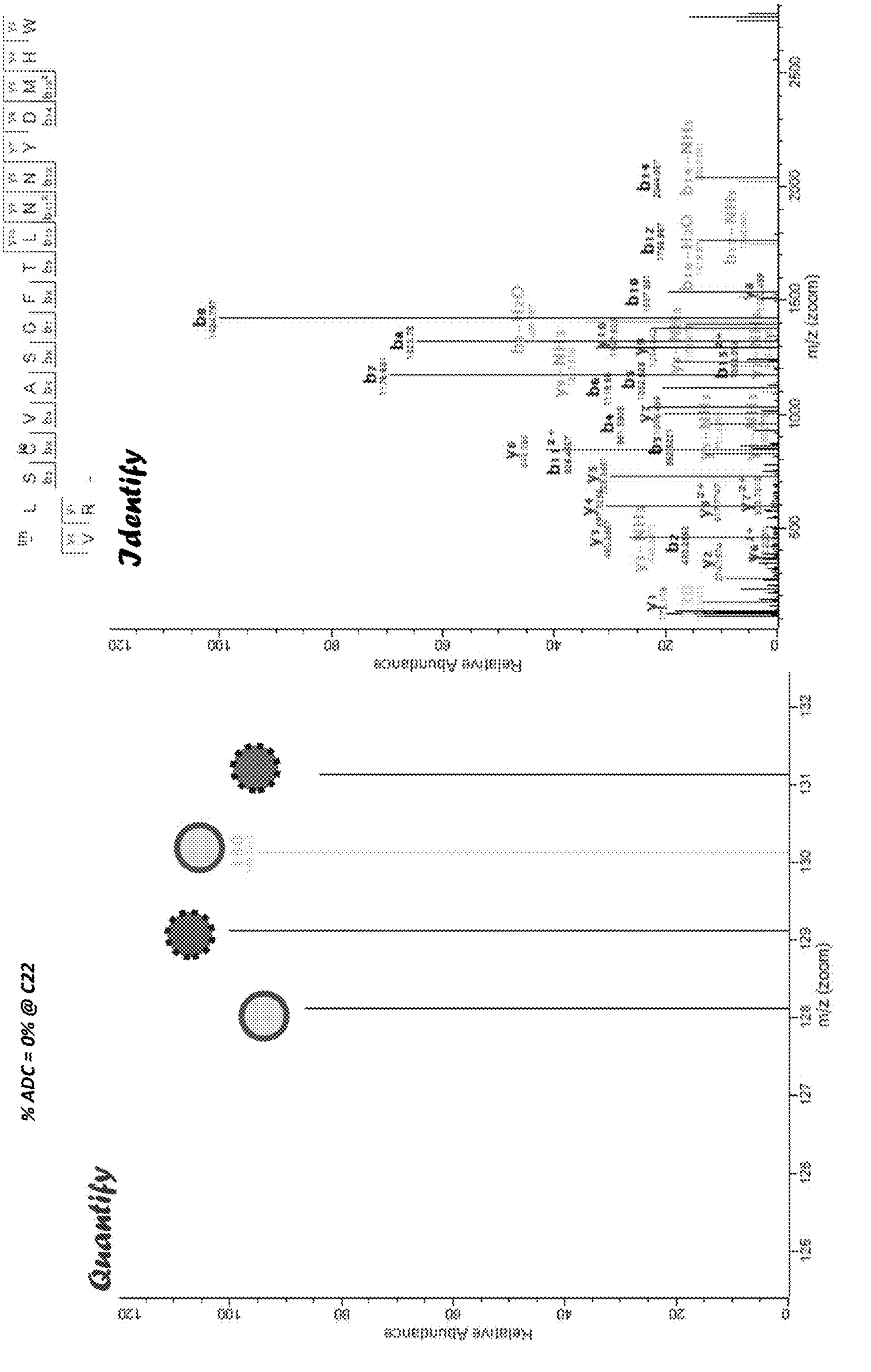
Figure 14A:
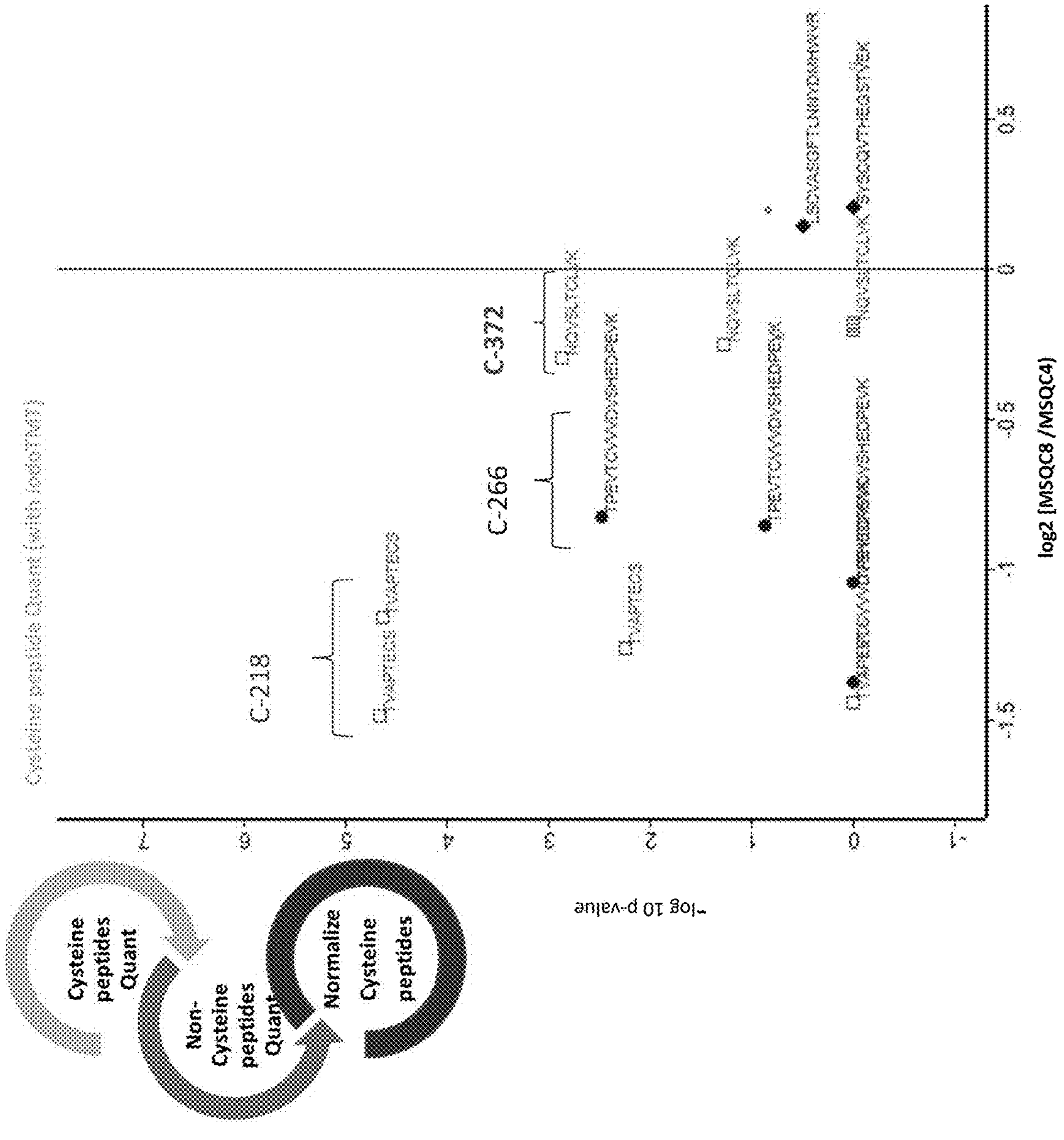
FIGS. 14A-14C show that MSQC8 site-wide ADC quantification using a method according to an embodiment of the application correlates with a known method: MSQC8 light chain conjugation at Cys-218=60% based on triple play quant and correlate with light chain SLIM-IMS DAR0/DAR1 ratio of 1:2, and occupancies at Cys-266 (max)=60% and Cys-372=15% were estimated while all other cysteines showed 0% conjugation.
Figure 14B:
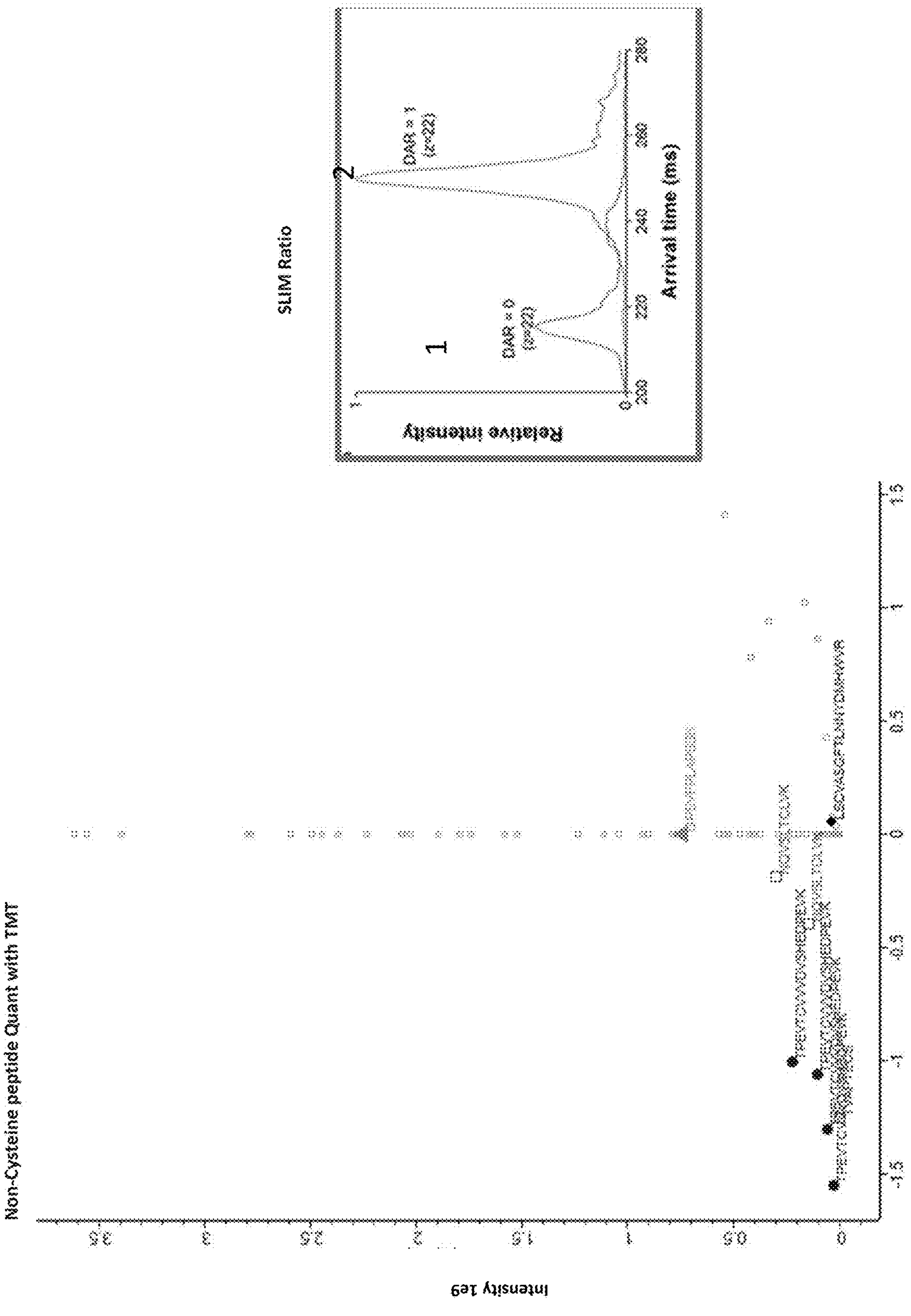
Figure 14C:
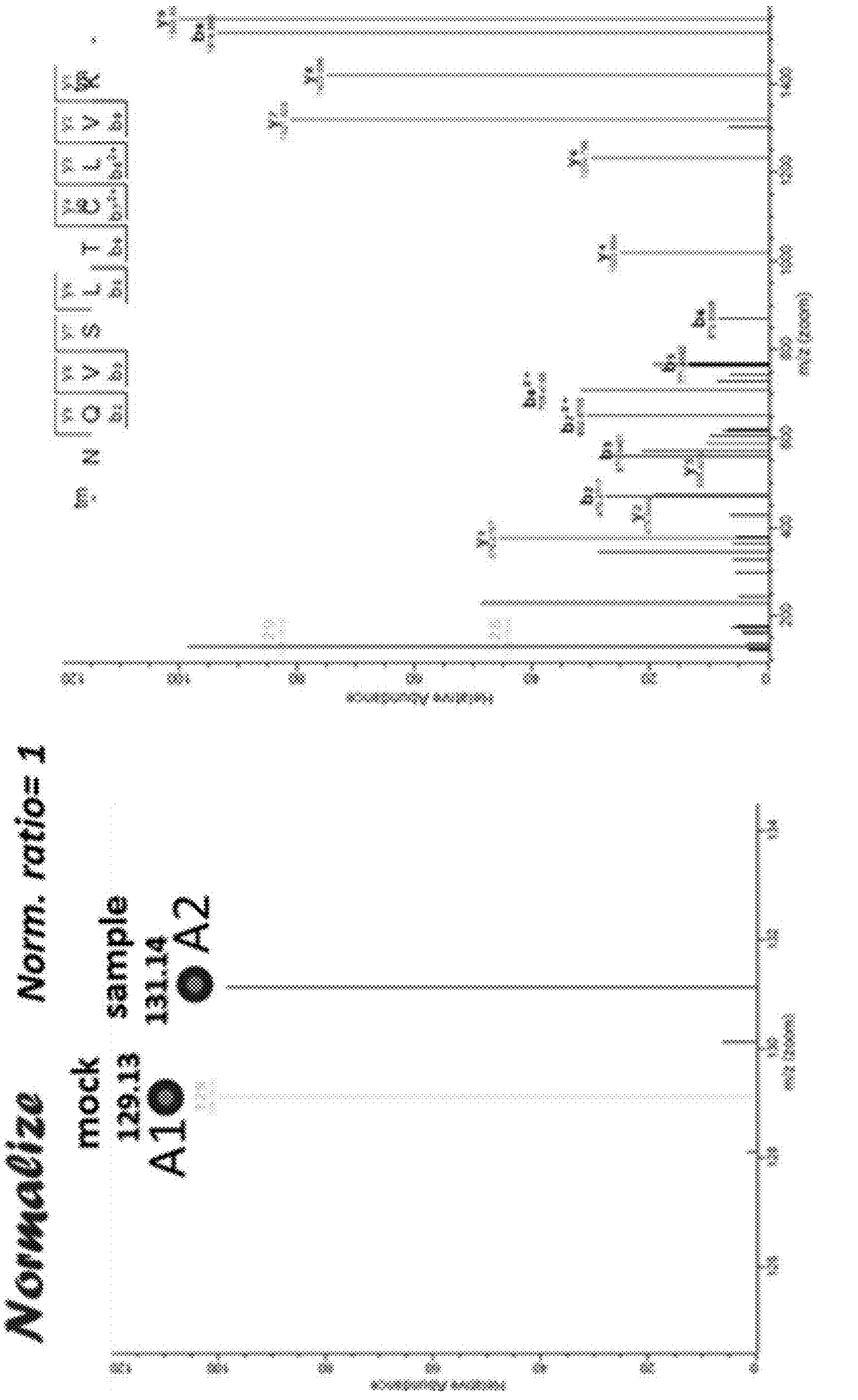

FIGS. 13A, 13B, and 14 illustrate an experiment and results of using dual TMTs for quantifying site-specific ADC on MSQC8 using a method according to an embodiment of the application. As shown in FIGS. 13A and 13B, when the labeling of the ADC was not complete, e.g., the conjugate was only labeled with the Cys reactive TMT, but not the Lys reactive TMT, the detected occupancy (% ADC) was only slightly lower than that with the complete labeling. Interestingly, similar site occupancies 55-60% were observed despite finding the peptide with incomplete labeling, which demonstrates the robustness of a method of the application.

Preferably, the conjugate is completely labeled with both TMTs. The completion of the labeling can be measured by the intensity of the reporting ion for the TMT on the mass spectrum. Results shown in FIGS. 13C-13F indicate that in MSQC8, the drug is conjugated to the antibody at Cys-266 and Cys-372. It was also observed that Cys-218 was the only conjugation site of dansyl-cadavarine-SMCC on the light chain with a site occupancy 60% is in close agreement with average DAR of 1 observed by SLIM-IMS (Nagy et al., *Anal*

*Chem* 92, 5004-5012 (2020)), as well as reduced mass analysis of MSQC8 (data not shown). Occupancies at Cys-266 (max) of 60% and Cys-372 of 15% were estimated, while all other cysteines showed 0% conjugation (see, e.g., FIGS. 14A to 14C). Such results are consistent with the DAR0/DAR1 ratio of 1:2 obtained from an existing method, e.g., light chain structures for lossless ion manipulation combined with ion mobility spectrometry (SLIM-IMS). Furthermore, using a large number of peptides to normalize for differences in mixing between two samples (i.e., MSQC8 ADC sample and MSQC4 mock) ensures that the occupancy estimates for each conjugation site is accurate.

Figure 15:
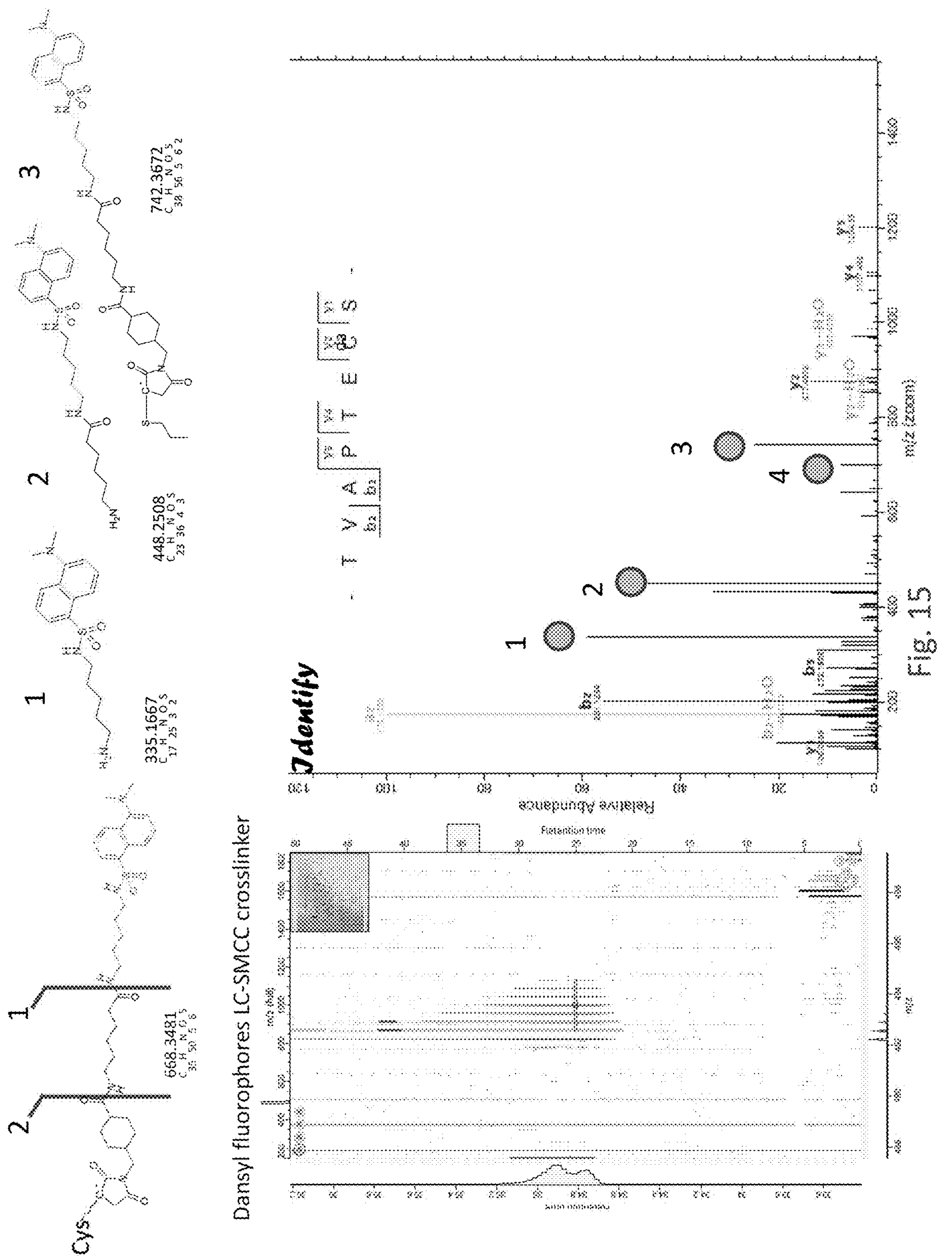
FIG. 15 illustrates the identification of dansyl fluorophore in MSQC8 using a method according to an embodiment of the application, which showed that small molecule conjugates prone to fragmentation producing complex spectra and the fragment masses from the drug are specific for each drug.

Methods according to embodiments of the application can also be used to characterize or identify the structure of the drug conjugated to a polypeptide. As shown in FIG. 15, small molecule conjugates prone to fragmentation producing complex spectra. The fragment masses from the drug are specific for each drug and can be used for the identification of the drug. FIG. 15 shows a series of immonium ions of SigmMAb dansyl-cadavarine-SMCC conjugate, which are drastically different from immonium ions of Biotin PEO acetamide. Similar to the results of FIGS. 8A and 8B, by using a specific reporter ion m/z to trigger ETD, a method of the invention allows for unambiguous site localization using ETD-$MS^2$ agnostic of the structure of the small molecule drugs propensity to generate fragments. In other words, TMT reporter m/z is specific whereas reporters from the drug varies m/z depends on the structure of the molecules.

According to other embodiments of the application, a dual TMTs mass spectrometry analysis according to the invention can also be used for profiling reaction time course for a conjugation reaction (see, e.g., FIGS. 16A-16B, 17A and 17B). In the dual TMT experimental scheme for FIGS. 16A and B, a single TMT was used on synthetic peptide standard (such as a HSA peptide) with different numbers of cysteine residues for multiplex reaction time course experiments combining TMT with fluorescence.

Figure 18A:
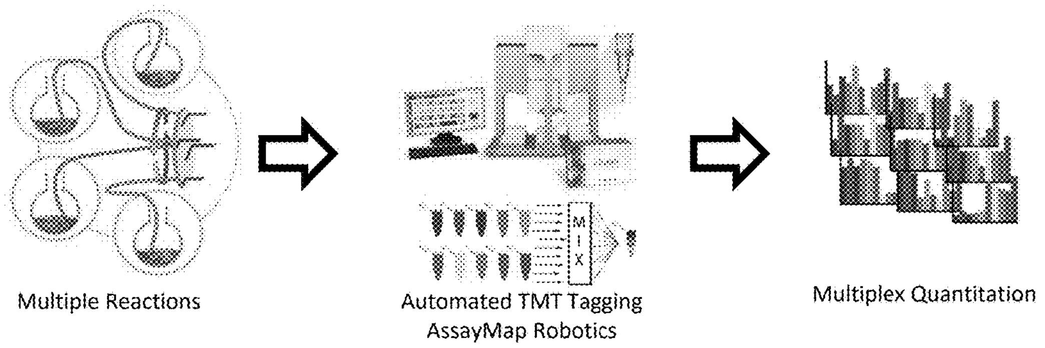
FIG. 18A describes a multiplexing scheme on how TMT are used in various combinations for the triple play analysis of up to 4 ADC samples using dual TMTs according to an embodiment of the application.

In further embodiments of the application, a dual TMTs mass spectrometry analysis according to the invention can be used in multiplex quantification of drug polypeptide conjugates to increase the throughput and reduce the costs. FIG. 18A illustrates a multiplex format where an additional drug conjugate sample is added to the original workflow. Multiplexing allows for multiple reaction conditions to be monitored in a single analysis which is advantages over separate workflows for each sample. The careful selection of TMT reagents with non-overlapping reporter ion masses allows for even higher number of sample multiplexing. Multiplexing also changes the reporter ion signatures for occupancy where the number of reporters in the barcode is (2n+2) for n number of samples. In the example of FIG. 18A, addition of a second sample results in a total of 6 reporters. Also, these reporters are from equal number of IodoTMT and TMT reagents. The number of reporter ions in the barcode for normalizing is half the number as the barcodes for occupancy and is (2n+2)/2. This is always the case in a dual TMT strategy where normalizing across sample is performed using only the amine reactive TMT reporter ions. It is important to note that the number of reporter ions in the barcode for mass triggering of the peptide drug conjugate is independent of the number of samples. Rather, the number of reporters for mass triggering is dependent on the number of possible conjugation sites: m. Typically when m=1, a single reporter is observed and when m>1, and the drug is not conjugated at all sites, two reporter ions are observed.

Figure 16A:
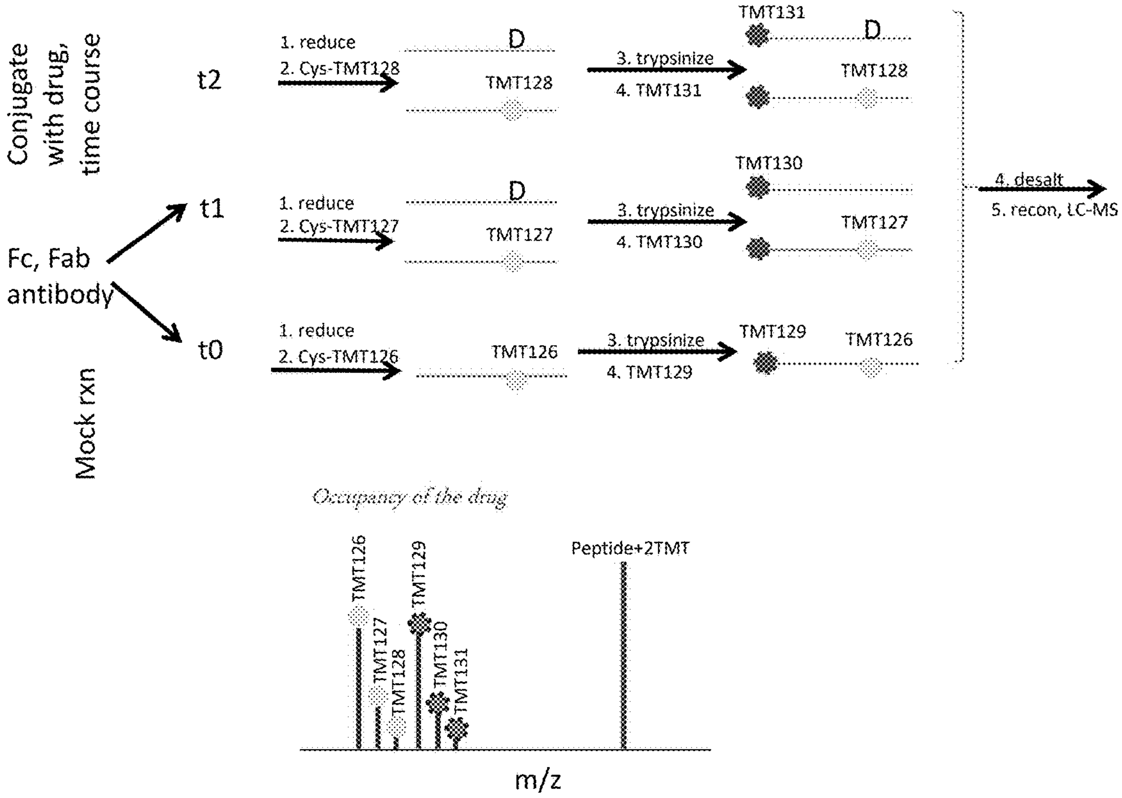
FIGS. 16A and 16B illustrate using TMT for profiling the reaction time course using a method according to an embodiment of the application.
Figure 16B:
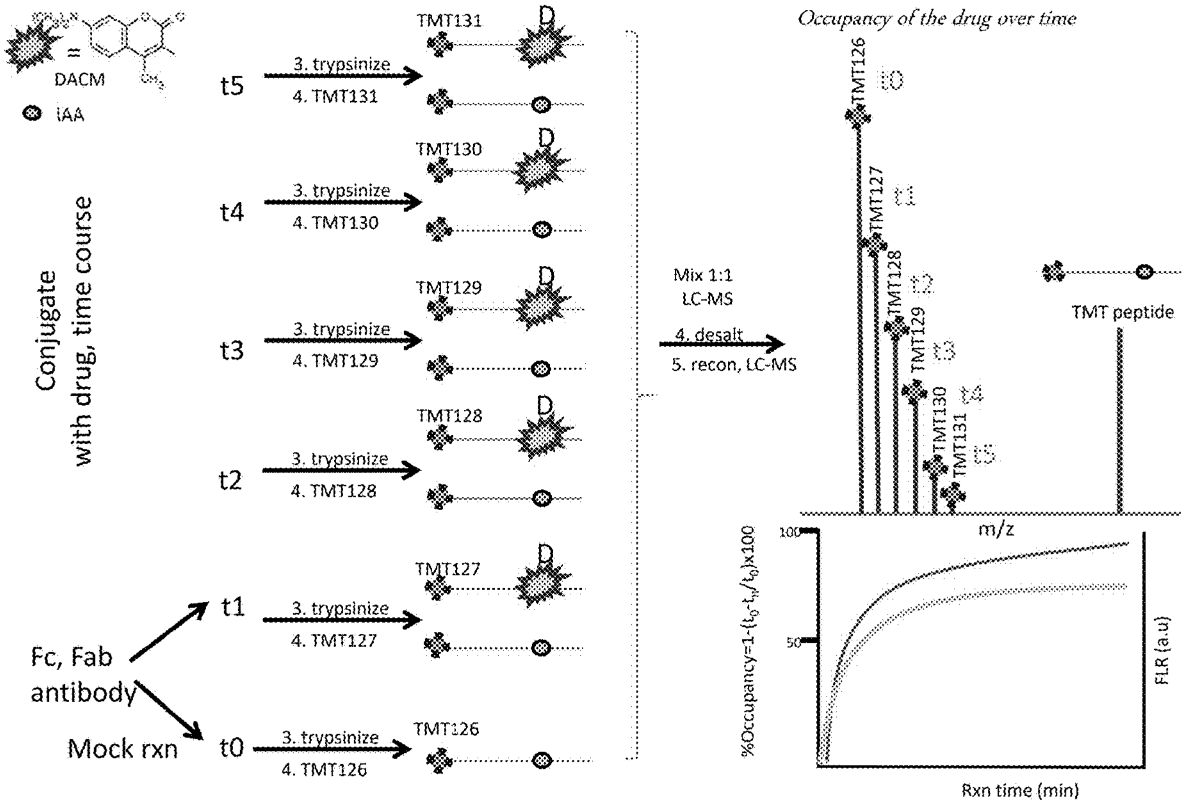
Figure 16C:
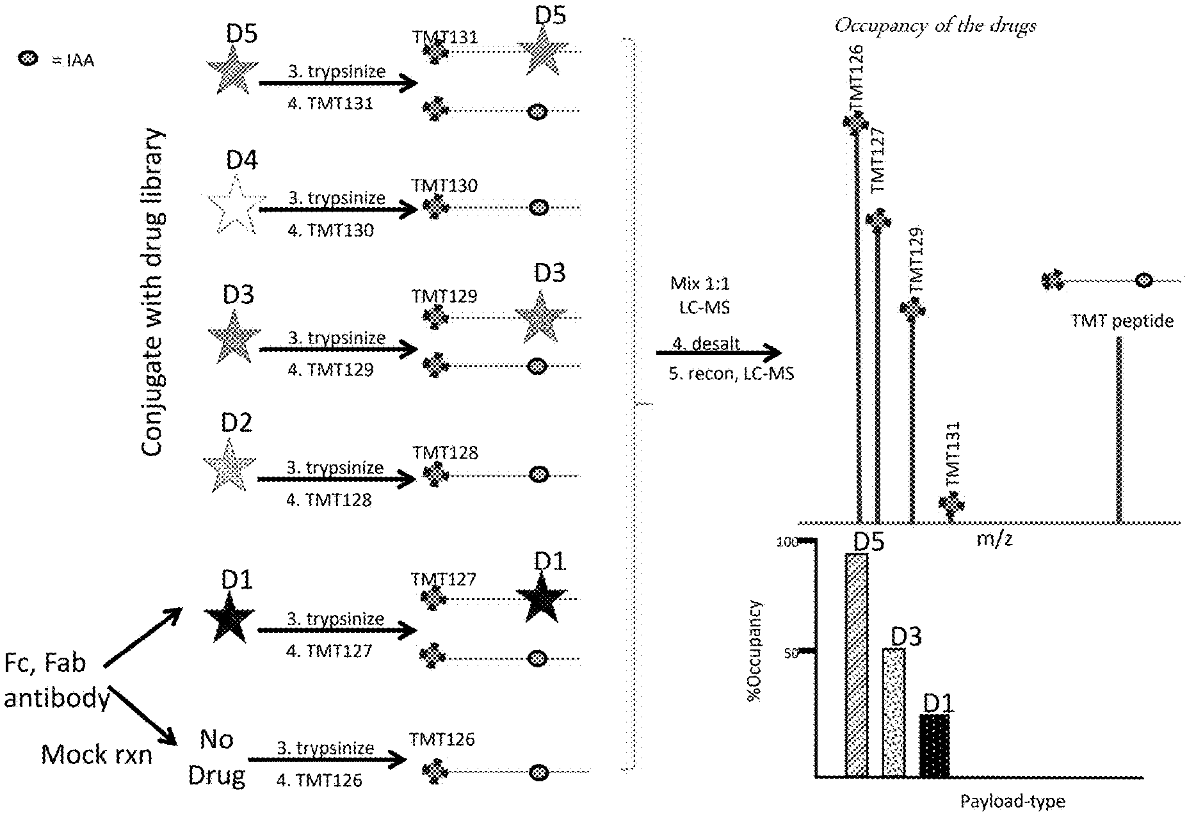
FIG. 16C illustrates a triple play workflow applied to monitoring the reaction of multiple drugs (D1, D2, D3, D4, and D5) in a multiplexed fashion according to an embodiment of the application.
Figure 16D:
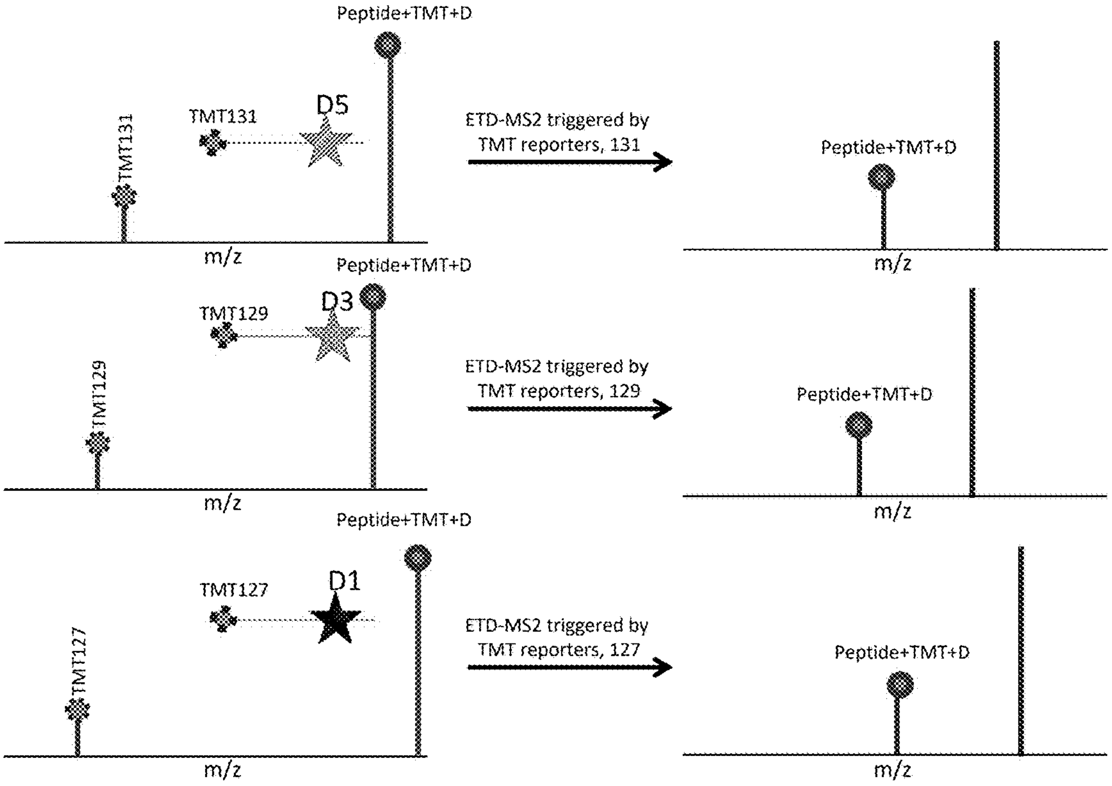
FIG. 16D illustrates mass triggering via a single TMT reporter ion that is specific to each drug molecule.

In certain embodiments of the application, a multiplexed triple play analysis can be used to analyze multiple samples containing conjugates having more than one conjugation sites. For example, synthetic peptides having 1-3 cysteine residues that are conjugated with the fluorescent molecule DCAM-3 are analyzed using a method of the application. FIG. 16B illustrates using a method of the application to monitor time points of a reaction using $iodoTMT^6$ in combination with IAA that blocks unreacted cysteines. In this method, $IodoTMT^6$ was not used as dual labeling approach in conjunction with $TMT^{10}$ as the upper limit for multiplexing is 4 under the assay condition. Currently the availability of $TMT^{16}$ (16-plex) and future n-plex reagents where n>16 would greatly facilitate the number of samples for a dual TMT approach. Fluorescence-based quantitation was used as the standard and compared with the TMT based occupancy estimation. FIG. 16C illustrates a triple play workflow of the application applied to monitoring the reaction of multiple drugs: D1-D5 in a multiplexed fashion. The scheme represents TMT labeling with IAA or iodoTMT to achieve dual labeling. The occupancy can be estimated for each drug using the reporter intensities to show the rank order for reactivity D5>D3>D1 and failed reactions of D2, D4 where occupancy was zero. FIG. 16D shows mass triggering via a single TMT reporter ion specific to each drug molecule i.e., TMT127 for D1 TMT129 for D2 and TMT130 for D3.

Figure 17A:
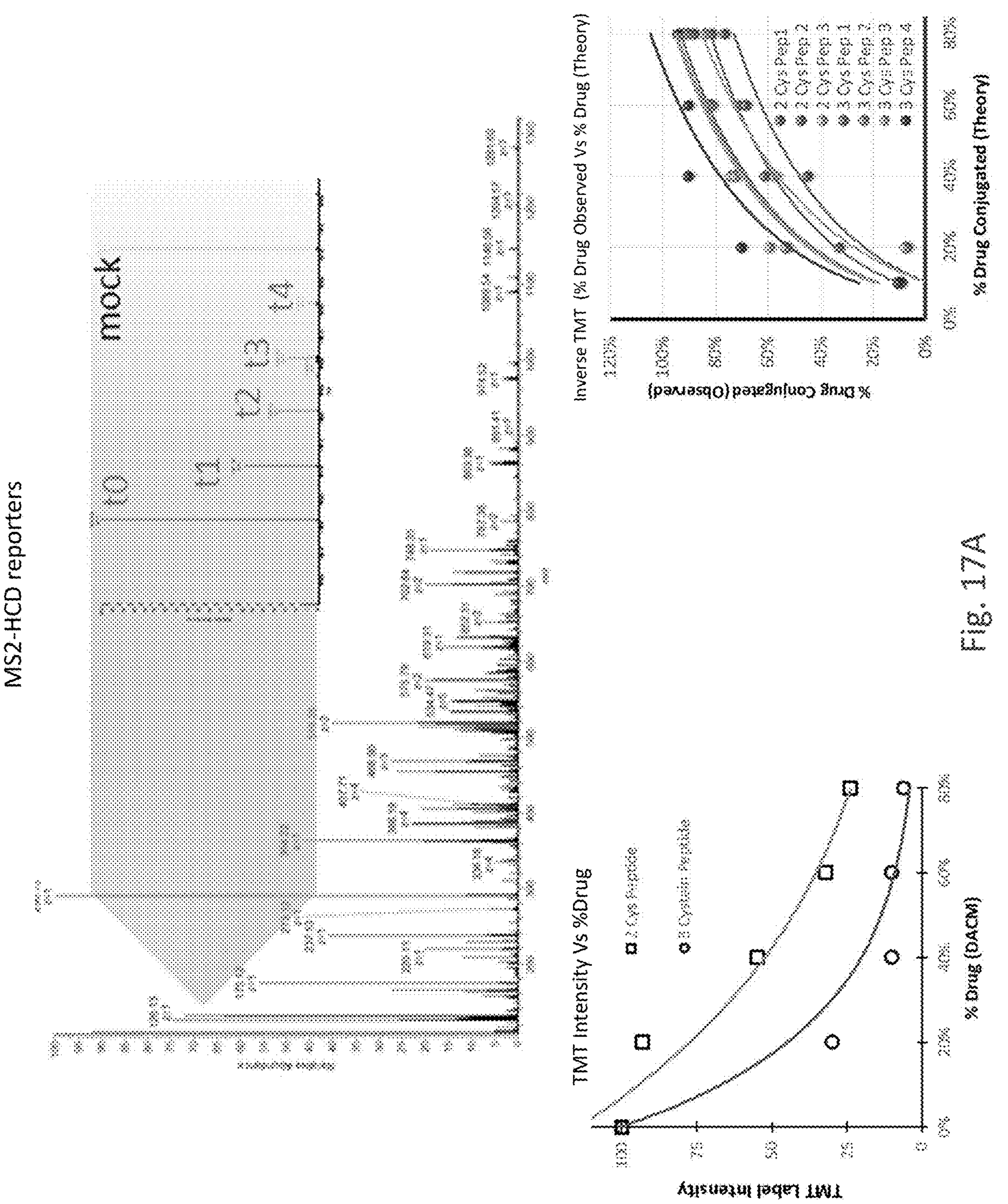
FIGS. 17A and 17B show that results from the TMT analysis correlated with that from fluorescence quantification at high occupancies.
Figure 17B:
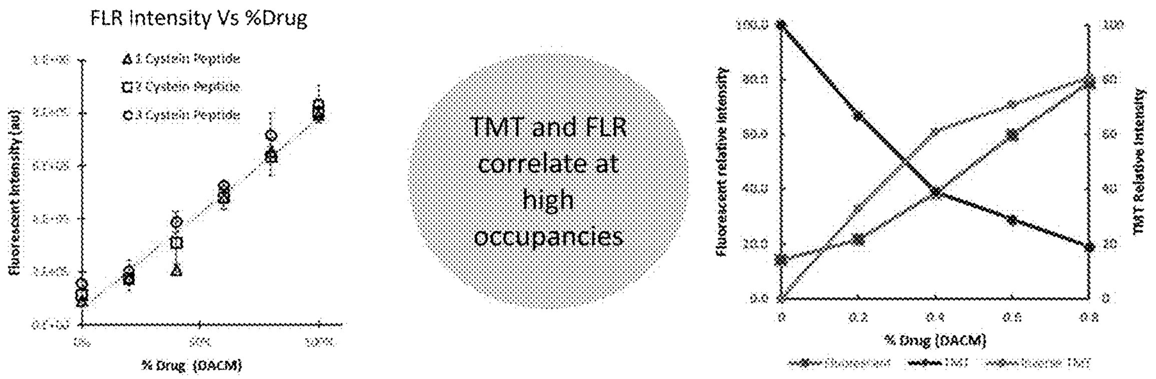

FIGS. 17A and 17B show the results from a multiplexing experiment, where reaction time points were simulated by mixing peptide-DACM-3 conjugated percent ratios of: 0, 20, 40, 60 and 80. Each peptide mixture was prepared separately such that unconjugated peptide counterpart was reduced first and all free-thiols were blocked with IAA. The conjugated peptide mixtures and the unconjugated counterparts of each peptide sequence was used for two parallel experiments. First, Fluorimetric measurements were performed to ensure DACM conjugation and mixing was accurate. The fluorescence intensity of all peptides having 1-3 cystine residues show a linear response from no conjugation (mock) to 80% conjugation. Next, the five peptide-DACM conjugate ratios of 0, 20, 40, 60, 80 and a mock and each sample was labeled with iodoTMT126, 127, 128, 129, 130 and 131 respectively and equimolar amount were mixed for reporter ion quantification. The HCD-MS2 reporter ions reflect a unique barcode for a reaction where the reactants deplete as the reaction proceeds and reaches a plateau. The reporter intensities of the of the peptide mixtures relative to its mock decreases with increased conjugation as expected. The correlation of the observed conjugation-levels to the expected or theoretical conjugation-levels was obtained based on TMT reporter ions. It is important to note that TMT reporter ion intensities are inversely related the conjugation levels. The dynamic compression of TMT ratios especially for low-intensity reporter ions affect mostly the high-drug conjugates.

An algorithm, such as that reported by Savisky et al., can be used to correct for ratio compression (Savisky et al., 2013, *Journal of proteome research* 12, 3586-3598), the entire content of which is incorporated herein by reference. SPS-MS3 routine available on current instrumentation can also ameliorate ratio compression (McAlister, et al., *Anal Chem* 86, 7150-7158 (2014). Nevertheless, a method of the application, without any correction, can provide an accurate estimation of low-level conjugation where TMT response is a linear function of conjugation. The detection of low-stoichiometries of conjugates is beneficial as most off-target conjugations is undesirable and can be monitored more accurately. The multiplex TMT ratios and or the inverse TMT ratios (site-occupancy) were compared with fluorescence-based yield estimates. The linear dynamic range for fluorescence-based measurement is high compared to dynamic range for occupancy of TMT reporters due to ratio compression. However, TMT reporters with high-intensity are also channels that have low-level conjugation that can be measured with less ratio compression effects and missing values (Lim et al., *Journal of proteome research* 16, 4217-4226 (2017)).

In another embodiment, a method of the application comprises using a robotic system. For example, a Triple Play workflow of the application can be implemented on AsayMap Bravo liquid handling robotic system where dual labeling and sample multiplexing with TMT reagents can increase the accuracy and precision of TMT based quantitation. FIG. 18A illustrates the overall scheme where automation can benefit especially for the robust monitoring of reactions at the point of synthesis. Simultaneous analysis of multiple drug conjugation reactions can be useful when reaction conditions need to be optimized rapidly. Also, sequential conjugation reactions that require estimation of drug occupancies of intermediate steps in addition to the final product to optimize the overall yield. The speed and reproducibility that any automation platform provides with multiplexing is necessary to reduce human error during sample handling.

Figure 18B:
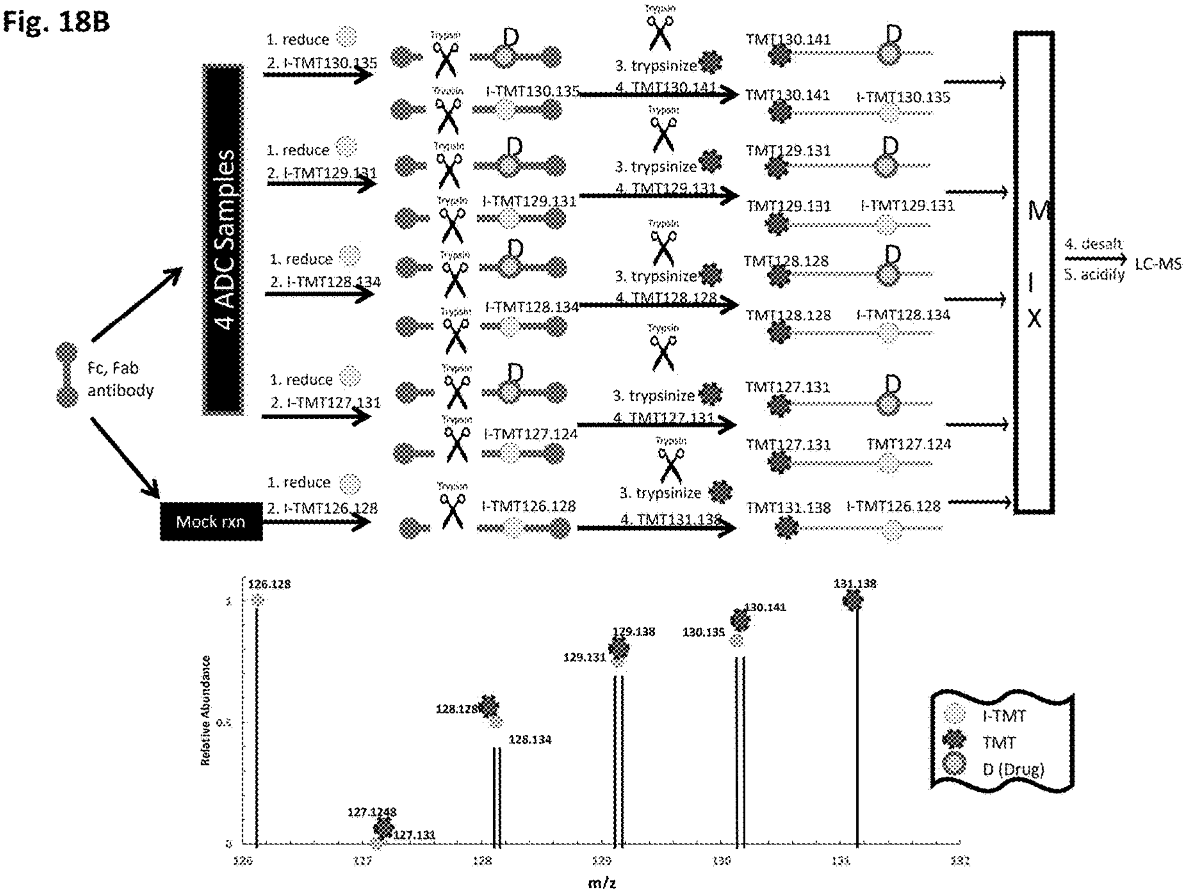
FIG. 18B illustrates multiplexed analysis of 4 ADC samples with 4 different site-specific ADC occupancies according to an embodiment of the application; the TMTs of TMT10plex reagents were used.

In one embodiment, a sample multiplexing scheme of the application can analyze up to four ADC samples using dual TMT labeling of the sample, such as MSQC8, at two different concentrations in duplicate. FIG. 18B illustrates the selection of dual TMT reporters from $TMT^{10}$ and $IodoTMT^{6}$ reagents such that all masses are unique. The $TMT^{10}$ (10-plex) reagents have 6 of the 10 isotopes that have isotopologues labeled as $TMT^{10}$ xN or $TMT^{10}$ xC that differ by 6.32 mDa (milli Dalton) where a $C^{12}$, $N^{15}$ atom pair is substituted with $C^{13}$, $N^{14}$. $TMT^{10}$xC isotopologues masses are identical masses to iodoTMT reagents and cannot be used concurrently. Once samples are multiplexed with the correct combination of reporter ions, high-resolution mass spectrometry allows for base line separation of reporter ion masses and their isotopologues. Four different ADC samples and a mock or unconjugated sample are dual TMT labeled as shown in the scheme such that cysteine containing tryptic peptides is an isobaric mixture of 5 TMT reporters and 5 iodoTMT reporters. Upon MS2, a barcode consists of 10 reporter ions.

Figure 19A:
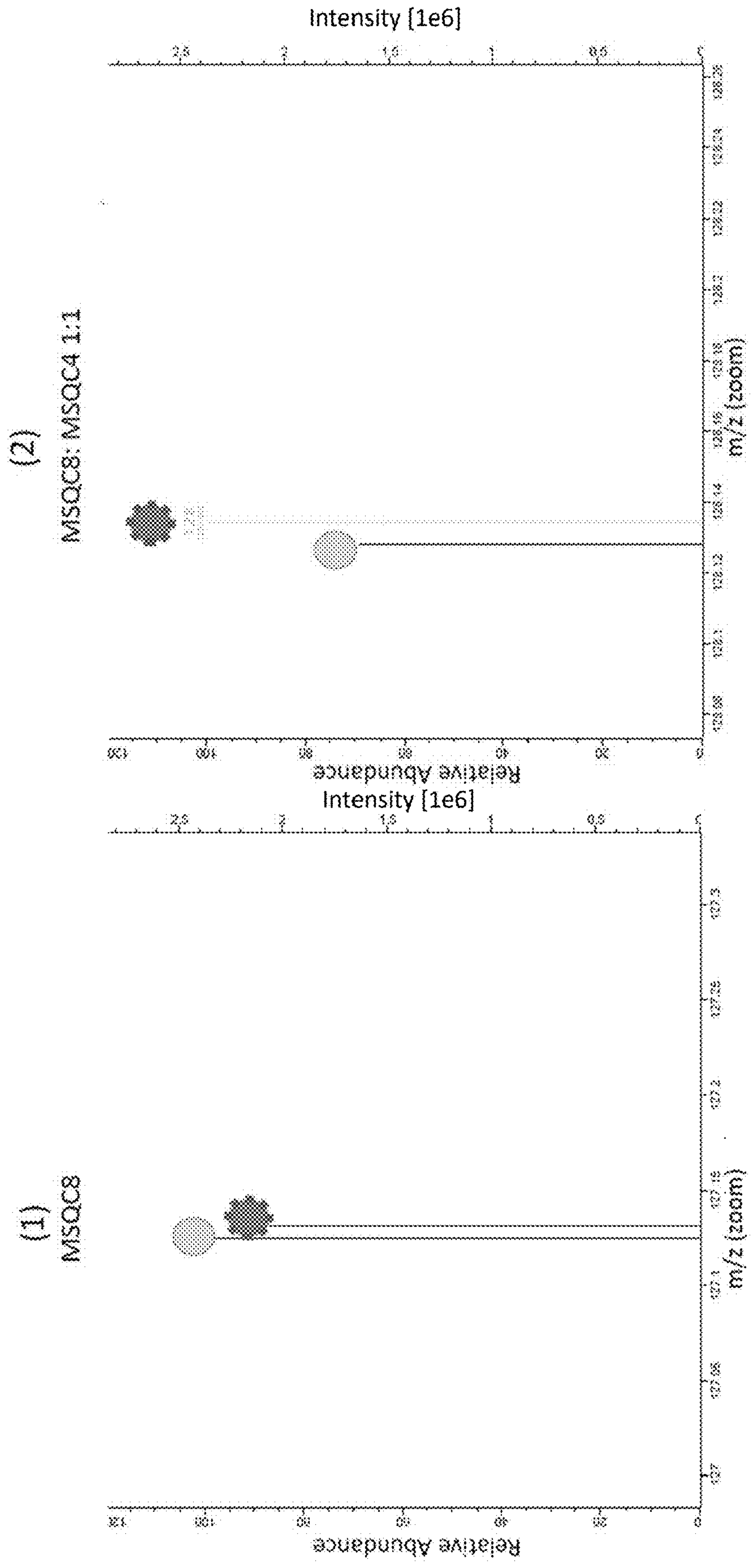
FIGS. 19A-19C illustrate the result of using a method of the invention to analyze at high throughput, e.g., analyzing 4 ADCs, which had achieved triple play, dual TMT quantification of four ADC samples in a single run.
Figure 19B:
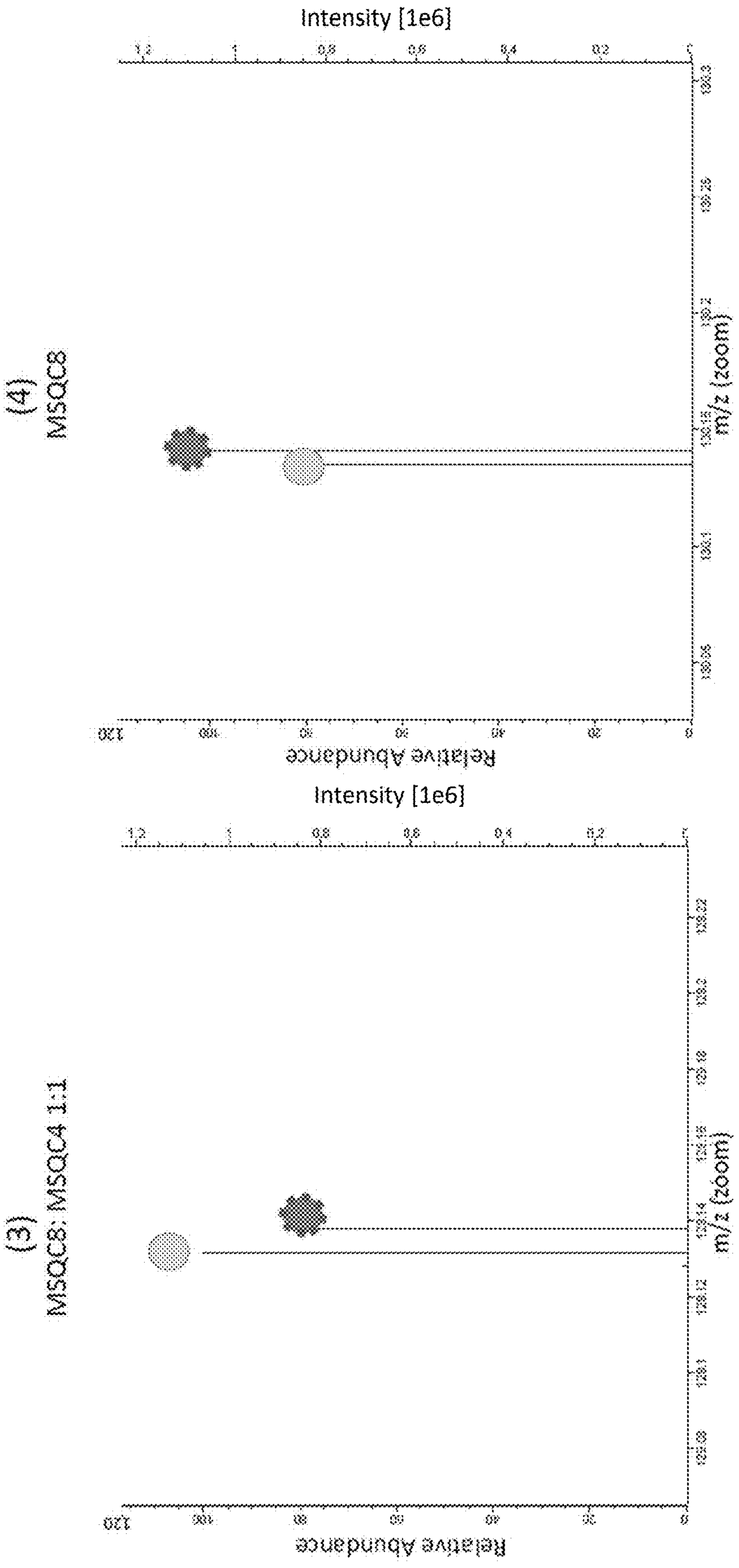
Figure 19C:
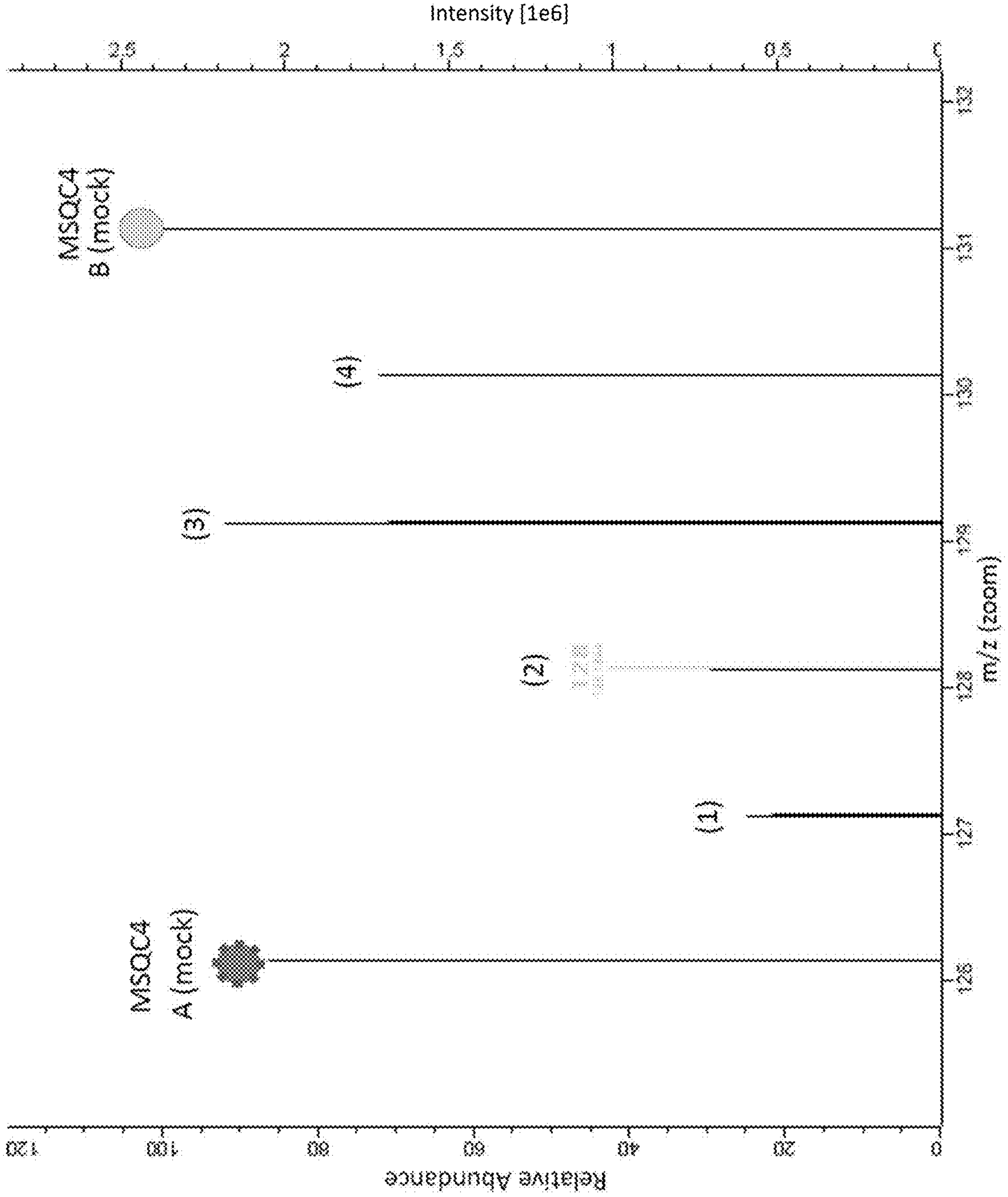
Figure 20A:
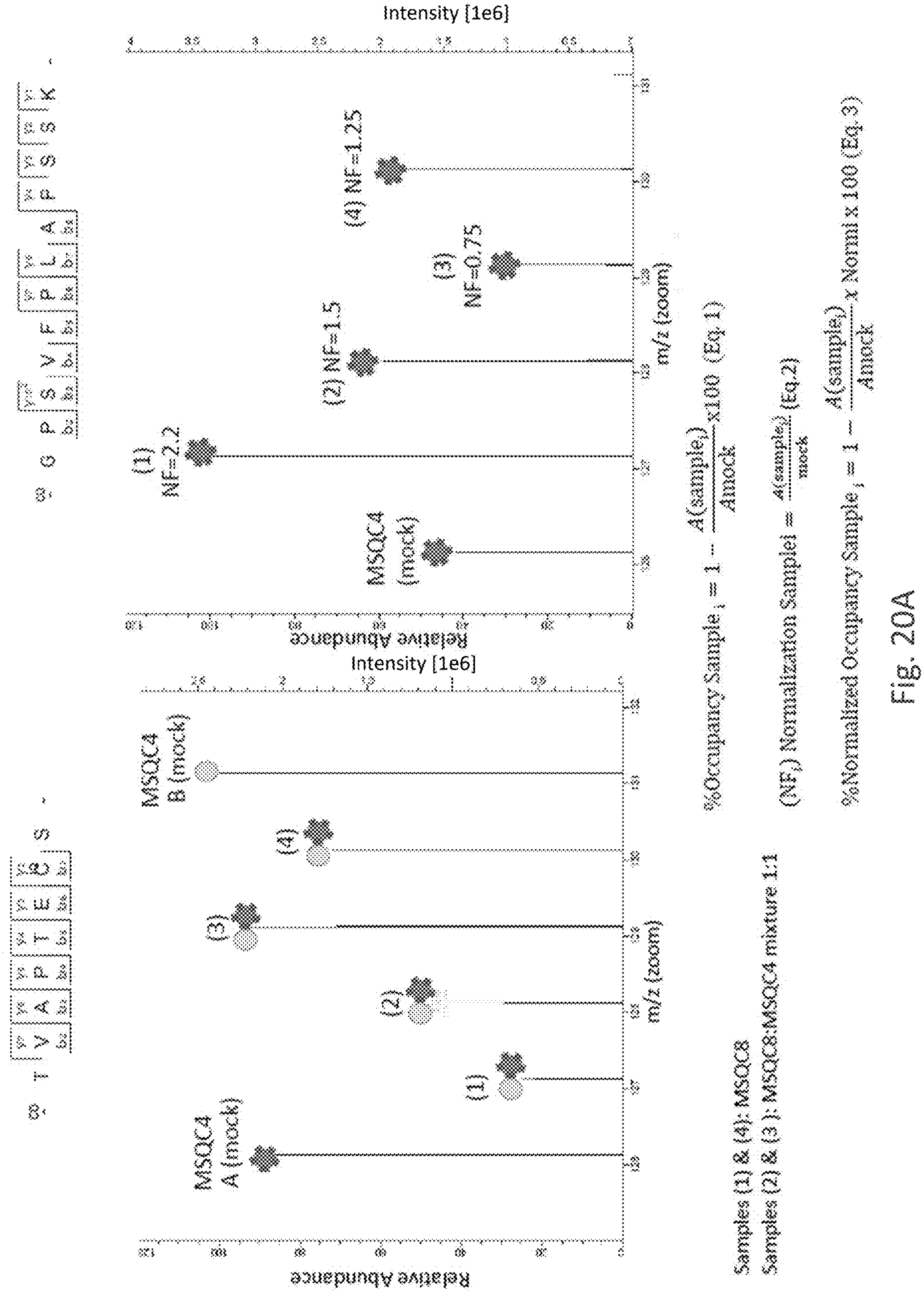
FIG. 20A shows the use of a non-cysteine peptide sequence, now having a barcode of five $TMT^{10}$ reporter ions upon MS2-HCD (one mock (B) and four conjugate samples (1) to (4)) to correct for sample concentrations in the multiplexed experiment: the normalization factors for the $i^{th}$ sample is given by Eq 2, and the corrected occupancies for each ADC sample can be obtained by Eq 3.

Four MSQC8 drug conjugate mimics were prepared at two concentrations; the original sample and another at half the concentration by diluting with MSQC8 with MSQC4. Each of these samples was a sample duplicated in the dual TMT labeling. FIG. 19 shows the reporter ions of Cys-218 peptide after HCD-MS2. The reporters of the mock (MSQC4) was dual labeled with $TMT^{10}$-126 and $IodoTMT^{6}$-130 pairs, while the four samples were labeled with $TMT^{10}$ xN, $IodTMT^{6}$x reagents where x range from 127-130. The replicate 1 of MSQC8 was labeled with dual reagents x=127, and the replicate of MSQC8 was labeled with dual reagents x=130. Likewise, the two replicates for equimolar mixture of MSQC8 and MSQC4 labeled reagents where x=128 and 129. The site occupancy at Cys-218 for the $i^{th}$ sample is given in Eq. 1. FIG. 20A shows the use of a non-cysteine peptide sequence, now having a barcode of five $TMT^{10}$ reporter ions upon MS2-HCD (one mock and four samples) to correct for sample concentrations in the multiplexed experiment. The normalization factor for $i^{th}$ sample is given by Eq 2. The corrected occupancies for each ADC sample can be obtained by Eq 3. FIG. 20B shows the Normalized occupancies obtained for the four samples in a single acquisition. These multiplex experiments in principal can also be used to identify the drug conjugate using trigger masses.

In one embodiment of the application, the relative occupancies between any two reaction steps can be determined when a reaction proceeds via an intermediate step or where the reference material is unavailable (see, e.g., FIGS. 20A and 20B). As shown in FIGS. 16A and 16B, occupancy can be estimated for a peptide conjugated to the fluorophore drug mimic, DACM-3 via two step antibody conjugation reactions. An example of a two-step antibody conjugation reaction is a transglutaminase reaction followed by click addition of a cytotoxic payload. See also, e.g., Huggins, et. al., *Molecules.* 2019 September; 24(18): 3287, the content of which is incorporated herein by reference in its entirety. Any of the ADCs prepared by a two-step antibody conjugation reaction, can be analyzed by a method of the application.

The invention will now be described in further detail with reference to the following specific, non-limiting examples. It should be appreciated by those of skill in the art that the techniques disclosed in the examples which follow represent techniques discovered by the inventor that function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1: Dual TMT Labeling and Conjugation for Unconjugated mAbs

Four different ratios (1:1, 1:9, 9:1, and 1:3) of reduced and drug conjugated NIST monoclonal antibody ((mAb), Sigma Aldrich, Catalog No. 8671) (Sample #1) to non-reduced and IodoTMT™-tagged NIST mAb (Sample #2) were prepared. NIST mAb was conjugated by using either iodoacetamide (IAA) (Sigma Aldrich, Catalog No. 16125) or Biotin PEO Iodoacetamide (Sigma Aldrich, Catalog No. B2059). For Sample #1, 2 aliquots of 100 μg of NIST (50 μl of 2 mg/ml NIST) were prepared by combining 10 μl of stock (10 mg/ml) with 40 μl of a solution that comprised 8M guanidine hydrochloride (GuHCl) (Sigma Aldrich, Catalog No. G3272), and 4 mM ethylenediaminetetraacetic acid (EDTA) (Sigma Aldrich, Catalog No. 03620). The NIST aliquots were then reduced by the addition of 10 μl of 1M DTT (Sigma Aldrich, Catalog No. 1019777001) and incubated at 37° C. for 1 hour. Alternatively, TCEP can also be used as a reducing agent instead of DTT. While DTT is usually active at neutral-basic pH conditions, TCEP has a wide pH range and a stronger reducing agent.

NIST was conjugated with 1M IAA. 1M IAA was prepared by adding 300 μl of trimethyl ammonium bicarbonate (TEAB) (ThermoFisher, Part of TMT labeling kit) to an Eppendorf tube, which was vortexed and sonicated for 20 minutes to equilibrate TMT reagents to room temperature prior to use. Then 24 μl of 1M IAA was added to the reduced NIST samples, which were incubated in the dark at room temperature for 1 hour. Following the incubation period, 15 μl of 1M DTT was added to the samples to quench the conjugation reactions. The samples were desalted by combining them with a buffer exchange solution (8M GuHCl+4M EDTA) and placed through a Zebra™ spin desalting column with a molecular weight cut off of 7 kDa (ThermoFisher, Catalog No. 89882).

To conjugate the reduced NIST samples with Biotin PEO Iodoacetamide, the samples were buffer exchanged to sulfhydryl-free PBS (phosphate-buffer saline) at a pH of about 7.5. Immediately before use, a 20 mM stock solution of Biotin PEO Iodoacetamide was prepared (190 µl of PBS was added to 2 mg of Biotin PEO Iodoacetamide in an Eppendorf tube). The reduced NIST samples in PBS were combined with 5 µl of 20 mM Biotin PEO Iodoacetamide and mixed. The reactions were incubated on ice or at room temperature for 2 hours. Following the incubation period, the samples were desalted. The samples were placed into a buffer exchange solution (8M GuHCl+4M EDTA) and run through a Zebra™ spin desalting column with a molecular weight cut off of 7 kDa.

Sample #2 (IodoTMT™-tagged non-reduced NIST samples) was prepared by generating 3 aliquots of NIST (50 µl of 2 mg/ml NIST combined with 10 µl of stock (10 mg/ml)) and added to 40 µl of a solution (8M GuHCl+4 mM EDTA)). Each aliquot was combined with 50 ul of the solution that contained 8M GuHCl and 4 mM EDTA to offset the volume. To reduce the samples for subsequent iodoTMT labeling, 10 µl of DTT was added to each aliquot and the samples were incubated at 37° C. for 1 hour. The following four ratios of Sample #1 and Sample #2 were prepared: 1) 1:9 ratio (10 µl of reduced NIST: 90 µl of non-reduced NIST), 2) 1:3 ratio (25 µl of reduced NIST: 75 µl of non-reduced NIST), 3) 1:1 ratio (50 µl of reduced NIST: 50 µl of non-reduced NIST), and 4) 9:1 ratio (90 µl of reduced NIST: 10 µl of non-reduced NIST). Each mixed sample contained 100 µg of NIST and 2 µl of IodoTMT™-LabelA1 (10 µl methanol was added to 200 µg of IodoTMT™) was added to all of the samples. The samples were then incubated in the dark at 37° C. for 1 hour. To quench the labeling reaction, 4 µl of 0.5M DTT was added to each sample and incubated for an additional 15 minutes at 37° C. in the dark. The samples had their buffer exchanged with TEAB and the IodoTMT™-labeled proteins were digested with 4 µl of trypsin (1 mg/ml) for 4 hours to overnight at 37° C. The trypsin was quenched with 2 µl of 98% formic acid and 2 µl of TMT-LabelB1 (800 µg dissolved in 40 µl of anhydrous acetonitrile) was added to each of the 4 samples. The samples were incubated in the dark at 37° C. for 1 hour and the reactions were quenched by the addition of 8 µl of 5% hydroxylamine for 15 minutes at room temperature.

In addition to Sample #1 and Sample #2, a reference or mock sample, termed Sample #3, was prepared and tagged with IodoTMT™ tag. Sample #3 was prepared similar to the protocol used for Sample #2, except 4 instead of 3 samples were generated. Sample #3 was separately trypsinized and labeled with TMT-LabelB2. Sample #1 and Sample #2 each were mixed with 132 µl of Sample #3 at a volume ratio of 1:1, which resulted in TMT labeled proteins with unique isobaric reporter ion masses that formed four multiplexed samples for mass spectrometry. A maximum of four reaction mixtures can be multiplexed with dual-labeling with five unique reporter masses from IodoTMT™ and amine reactive TMT10Plex™ reagents (ThermoFisher, Catalog No. 90110). Dual labeled four conjugated samples and a single mock/reference control sample were combined at a volume ratio of 1:1:1:1:1, which created a single multiplexed sample for liquid chromatography-mass spectrometry.

FIGS. 13A, 13B, and 14 illustrate an experiment and results of using dual TMTs for quantifying site-specific ADC on MSQC8 using a method according to an embodiment of the application. As shown in FIG. 13A, when the labeling of the ADC was not complete, e.g., the conjugate was only labeled with the Cys reactive TMT, e.g., IodoTMT128 and IodoTMT130, but not the Lys reactive TMT, e.g., TMT129 and TMT131, for each of MSQC-4 and MSQC-8 respectively, the detected site occupancies (e.g., 55-60% ADC) in the single labeling was slightly less than that with dual labeling. Non-conjugated peptide with dual labels, e.g., IodoTMT128 and TMT129 for MSQC-4, and IodoTMT130 and TMT131 for MSQC-8, provide more precise estimate of 60% (measurement estimate coming from two reporters instead of one). The completion of the labeling was measured by the intensity of the reporting ion for the TMT on the mass spectrum. It was known that MSQC8 had several conjugation sites. Results shown in FIG. 13B indicate that in MSQC8, the drug was conjugated to the antibody at Cys-266 and Cys-372. Cys-218 was the only conjugation site of dansyl-cadavarine-SMCC on the light chain with a site occupancy 60% is in close agreement with average DAR of 1 observed by SLIM-IMS (e.g., Nagy, G. et al. *Anal Chem* 92, 5004-5012 (2020), which found drugs bound to both chains of the antibody). In addition, reduced mass analysis of MSQC8 Occupancies at Cys-266 (max) of 60% and Cys-372 of 15% were estimated, while all other cysteines showed 0% conjugation (see, e.g., FIG. 14). Such results were consistent with the DAR0/DAR1 ratio of 1:2 obtained from an existing method, e.g., light chain structures for losseless ion manipulation combined with ion mobility spectrometry (SLIM-IMS). It is important to note that using a large number of peptides to normalize for differences in mixing between two samples (i.e., MSQC8 ADC sample and MSQC4 mock) ensures that the occupancy estimates for each conjugation site is accurate.

Example 2: Dual TMT Labeling of Conjugated mAbs

Conjugated mAbs were labeled with a dual TMT labeling protocol. MSQC8 (Sigma Aldrich mAb antibody-drug conjugate mimic) and MSQC4 (Sigma Aldrich mAb standard) were used as the conjugated sample and the reference or mock sample, respectively. The samples were tagged with distinct IodoTMT™ tags following the sample protocol used as described for tagging NIST mAB and separately trypsinized to create peptides. The resulting peptide mixtures from MSQC8 and MSQC4 were separately labeled with distinct amine reactive TMT tags following the same protocol used to label NIST mAb with TMT or IodoTMT™. Following TMT dual labeling, the samples were mixed at a volume ratio of 1:1, which created a multiplexed single sample for mass spectrometry.

Example 3: Automatic of TMT Labeling in AssayMap Bravo

The dual TMT labeling protocol was implemented in an AssayMAP Bravo (Agilent) robotic system, which automates protein sample preparation prior to analysis with LC-MS. Dual TMT labeling of conjugation of unconjugated NIST mAb was performed as previously described. The In-Solution Digestion Single Plate Protocol was used according to the manufacturer's instructions, which is incorporated herein by reference in its entirety (see, worldwide web: agilent.com/cs/library/applications/application-protease-digestion-in-solution-assaymap-5994-1682en-agilent.pdf). The automated sample preparation was programmed to dispense a minimum volume of 5 µl and the samples were desalted with reverse phase protein clean up using RP-W cartridge application as known in the art. The different sample ratios (e.g., 1:1, 1:9, 9:1, and 1:3) were performed with the reformatting utility in the AssayMAP Bravo robotic system.

Example 4: Multiplex TMT Labeling of Conjugated Peptides

Synthetic mAbs with 1-3 cysteine residues were separately conjugated with N-(7-Dimethylamino-4-Methylcoumarin-3-yl)Maleimide (DACM-3; ThermoFisher, Catalog No. D10251) via an adapted manufacturers' protocol for protein labeling. A stock solution of 16.76 mM DACM-3 was prepared. 1 mg of each peptide was dissolved in 1 mL of a solution that comprised 100 mM PBS, 0.1M NaCl, 10 mM EDTA (pH 8.0) and 50 μl of 16.76 mM DACM-3. The peptides were sealed with a light protective cover and incubated for approximately 5 minutes at ambient temperature. Mass spectrometry was used to confirm that the peptides were completely conjugated. The relative fluorescence (relative fluorescent units or RFUs) of the samples and of a standard curve of N-acetyl-L-Cysteine (cysteine peptides standards from NIST monoclonal antibody were synthesized to 99.99% purity by Biomatik Corporation) was measured (Excitation=385 nm, Emission=465 nm, 455 nm cutoff) with a fluorescent plate reader (Spectramax M5, Molecular Devices). The relative concentration of free-thiol or conjugated thiol for each peptide was calculated from a regression analysis of the internal N-acetyl-L-Cysteine curve. N-acetyl-L-cysteine was determined to be essentially 100% reactive with DACM-3.

Following DACM-3 conjugation of the peptides, the peptides were labeled with TMT. Each DACM-3 conjugated peptide was mixed with an unlabeled peptide counterpart to create five mixtures at various stoichiometric ratios (0, 0.2, 0.4, 0.6 and 0.8). The unlabeled peptide served as a control. The samples were evaluated with a fluorescence assay as known in the art in view of the present disclosure to ensure that the DACM-3 label worked appropriately prior to TMT labeling. Amine reactive 6-plex TMT labeling was performed on each sample as previously described for TMT labeling of tryptic peptides. Finally, the labeled five mixtures and control were combined each at a volume ratio of 1:1 and analyzed with LC-MS using method known known in the art in view of the present disclosure.

Example 5: LC-$MS^2$ (LC-MS/MS) Analysis

Samples that were analyzed with LC-$MS^2$ were separated on an Agilent Infinity 12900 UHPLC with an AdvanceBio Peptide Mapping column (Agilent, Catalog No. 864600-911) at 65° C. A 50 minute liquid chromatography (LC) gradient program that used LC-MS grade water with 0.1% formic acid as mobile phase A and acetonitrile as mobile phase B was conducted according to the following protocol: 0 min, 2% B; 35 min, 30% B; 40 min, 80% B; 45 min, 85% B; 45.5 min, 2% B; and a subsequent re-equilibration for 5 min at 2% B. The flow rate was set to 0.2 mL/min and the injection volume was 2 μl. The mass spectrometer was operated in positive ionization mode with a data dependent (dd) $MS^2$ HCD (MS/MS-HCD) and electron transfer dissociation (ETD) methods as known in the art. The following interface conditions were used: emitter voltage, +2600 V; vaporizer temperature, 325° C.; ion transfer tube, 325° C.; sheath gas, 55 (arb (arbitrary unit)); aux gas, 10 (arb); and sweep gas, 1 (arb).

The following internal mass spectrometer settings were used for MS scans: RF (radio frequency) lens, 60%; AGC (automatic gain control) target, 1e6; maximum injection time, 50 ms; and 1 μscan in profile mode at 70K resolution on the Orbitrap (OT) mass analyzer. The method sequentially included a series of filters prior to any $MS^2$ HCD events as known in the art. A monoisotopic peak selection filter was included and set as peptide for all methods and an intensity filter of 1e5 was used. Some methods used an optional charge state filter to select precursor charge states 2-6. Additionally, certain methods used an optional dynamic exclusion (DE) filter to more efficiently identify peptides in the samples with either a 12 s or 3 s exclusion window and exhibited the following common parameters: exclude n=1 times; +/−3 ppm; exclude isotopes; and single charge state per precursor. One method involved Apex detection, which used the following parameters: expected peak width, 6 s; desired apex window, 30%.

Five dd$MS^2$ OT-HCD (Data Dependent MS/MS-Orbitrap Detection-Higher Energy Collision Dissociation) scans were performed with the following settings: quadrupole isolation, 1.6 m/z isolation window; detector type, Orbitrap, auto m/z normal scan range, 70 K resolution, 100 m/z first mass; AGC Target, 2e5, inject ions for all available parallelizable time, 50 ms maximum injection time; 1 μscan, profile. Following dd$MS^2$ OT-HCD, a targeted mass trigger (TMT) was implemented, which is a scan that is only triggered if the system detects a product ion from the user defined list. Targeted ion masses included TMT reporter ion-specific to detecting a payload from the list of reporter masses (e.g., 126 to 131 Da) and only ions within the top 10 most intense mass-to-charge ratios were used for all mass triggers. The following conditions were used for dd$MS^2$ OT-ETD (Data Dependent MS/MS-Orbitrap Detection-Electron Transfer Dissociation): $MS^n$ Level, 2; quadrupole isolation, 1.6 m/z isolation window; ETD reaction time of 50 ms; detector type, Orbitrap, auto m/z normal scan range, 30 K resolution; AGC Target, 5e4, inject ions for all available parallelizable time, 22 ms maximum injection time; 1 μscan, profile. The number of dependent scans between dd$MS^2$ OT-HCD and dd$MS^2$ OT-ETD was set to 1.

Data from the various mass spectrometry analyses were processed with Xcalibur™ Data Acquisition and Interpretation Software (ThermoFisher, Catalog No. OPTON-3096 7, MaxQuant and Perseus source proteomics data analysis software (MaxPlanck Institute), and R 3.6 statistical programming software (R Foundation for Statistical Computing, Vienna, Austria). The site occupancy was estimated by Equation 1 with IodoTMT reporter ions peak areas where A2 is the area of unconjugated sample and A1 is the area of conjugated sample. A normalization factor was calculated by Equation 2 using TMT reporter ions where B1 is the peak area of a conjugated sample and B2 is the peak area of an unconjugated sample:

$$\%\ \text{Occupancy}\ Drug_{peptide} = \frac{A2 - A1}{A2} \times 100 \tag{1}$$

$$\text{Normalization Factor} = \frac{B1}{B2} \tag{2}$$

It is understood that the examples and embodiments described herein are for illustrative purposes only, and that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

The invention claimed is:

1. A method of analyzing a conjugate comprising a drug covalently linked to a polypeptide, comprising:

(i) contacting a sample comprising the conjugate with a first tandem mass tag (TMT) to thereby label the polypeptide of the conjugate with the first TMT;

(ii) digesting the polypeptide of the conjugate labeled with the first TMT to generate a first mixture comprising one or more unlabeled peptides and one or more peptides labeled with the first TMT;

(iii) contacting the first mixture with a second tandem mass tag (TMT) to thereby obtain a second mixture comprising one or more peptides labeled with at least one of the first TMT and the second TMT, optionally one or more unlabeled peptides, wherein the first TMT and the second TMT do not have the same reporter ion mass;

(iv) subjecting the second mixture to a liquid chromatography (LC) to generate elutes of the LC; and (v) subjecting the elutes to a tandem mass spectrometry to obtain a mass spectrum of a peptide comprising at least one reporter ion of the first TMT and the second TMT; and (vi) detecting the mass-to-charge ratio (m/z) associated with the at least one reporter ion to thereby analyze drug occupancy of the conjugate in the sample.

2. A method of analyzing a conjugate comprising a drug covalently linked to a polypeptide, comprising:

(i) contacting a sample comprising the conjugate with a first tandem mass tag (TMT) to thereby label the polypeptide of the conjugate with the first TMT;

(ii) digesting the polypeptide of the conjugate labeled with the first TMT to generate a first mixture comprising one or more unlabeled peptides and one or more peptides labeled with the first TMT;

(iii) contacting the first mixture with a second tandem mass tag (TMT) to thereby obtain a second mixture comprising one or more peptides labeled with at least one of the first TMT and the second TMT, optionally one or more unlabeled peptides;

(iv) contacting a control sample comprising the polypeptide not covalently linked to the drug with a third TMT to thereby label the polypeptide not covalently linked to the drug with the third TMT;

(v) digesting the polypeptide not covalently linked to the drug labeled with the third TMT to generate a third mixture comprising one or more unlabeled peptides and one or more peptides labeled with the third TMT;

(vi) contacting the third mixture with a fourth tandem mass tag (TMT) to thereby obtain a fourth mixture comprising one or more peptides labeled with at least one of the third TMT and the fourth TMT, optionally one or more unlabeled peptides;

(vii) combining the second mixture with the fourth mixtures and subjecting the combination to a liquid chromatography (LC) to generate elutes of the LC; and (viii) subjecting the elutes to a tandem mass spectrometry to obtain a mass spectrum of a peptide comprising at least one reporter ion of the first TMT, the second TMT, the third TMT and the fourth TMT; and (ix) detecting the mass-to-charge ratio associated with the at least one reporter ion to thereby analyze drug occupancy of the conjugate in the sample, wherein none of the first TMT, the second TMT, the third TMT and the fourth TMT has the same reporter ion mass, the first TMT and the third TMT are selected from a first isobaric set of TMTs, the second TMT and the fourth TMT are selected from a second isobaric set of TMTs, and the first isobaric set of TMTs are reactive to an unconjugated amino acid residue that is capable of forming a covalent bond with the drug, and the second isobaric set of TMTs are reactive to lysine or free amine at the N-terminus of a peptide.

3. A method of determining the occupancy ratio of a site of conjugation in the conjugate, comprising:

1) Obtaining a mass spectrum for a peptide labeled with both of the first TMT and the second TMT and a peptide labeled with both of the third TMT and the fourth TMT using the method of claim 2, wherein the mass spectrum comprises a reporter ion of the first TMT, a reporter ion of the third TMT, a reporter ion of the second TMT and a reporter ion of the fourth TMT;

2) Detecting the mass-to-charge ratio (m/z) associated with the reporter ions in the mass spectrum; and 3) Determining the occupancy ratio of a site of conjugation in the conjugate based on the intensity of the reporter ion of the first TMT and the intensity of the reporter ion of the third TMT, or the intensity of the reporter ion of the second TMT and the intensity of the reporter ion of the fourth TMT in the mass spectrum, preferably the occupancy ratio is determined by the following equation:

(the intensity of the reporter ion of the third TMT—the intensity of the reporter ion of the first TMT)/the intensity of the reporter ion of the third TMT, or (the intensity of the reporter ion of the fourth TMT—the intensity of the reporter ion of the second TMT)/the intensity of the reporter ion of the fourth TMT.

4. The method of claim 3, wherein the occupancy ratio of the site of conjugation in the conjugate is determined at various time points, wherein additional TMTs are used to label the polypeptides at different time points.

5. A method of normalizing the sample comprising the conjugate with the control sample, comprising:

1) Obtaining a mass spectrum for a peptide labeled with only the second TMT and a peptide labeled with only the fourth TMT using the method of claim 2, wherein the mass spectrum comprises a reporter ion of the second TMT and a reporter ion of the fourth TMT, but not a reporter ion of the first TMT or third TMT;

2) Detecting the mass-to-charge ratio (m/z) associated with the reporter ions; and 3) normalizing the sample with the control sample by the ratio of the intensity of the reporter ion of the second TMT to that of the reporter ion of the fourth TMT.

6. A method of localizing the drug conjugation site in the conjugate, comprising:

1) Obtaining a mass spectrum of a peptide labeled only with the second TMT using a method of claim 2, wherein the mass spectrum comprises only a reporter ion of the second TMT, but not a reporter ion of the first, third or fourth TMT; and 2) triggering a second tandem mass spectrometry analysis on the peptide labeled only with the reporter ion of the second TMT to thereby localize the drug conjugation site.

7. The method of claim 6, wherein the peptide is completely conjugated to the drug.

8. The method of claim 1, wherein the tandem mass spectrometry is a high energy collision-induced dissociation tandem mass spectrometry (HCD-MS2).

9. The method of claim 6, wherein the second tandem mass spectrometry is an electron transfer dissociation tandem mass spectrometry (ETD-MS2) or an electron-capture dissociation tandem mass spectrometry (ECD-MS2).

10. The method of claim 6, wherein a higher trigger intensity threshold and/or a narrow isolation window is used to improve the triggering of the second tandem mass spectrometry.

11. The method of claim 1, wherein synchronous precursor selection with tribrid technology is applied to the tandem mass spectrometry to improve the specificity and accuracy of the detection and quantification.

12. The method of claim 1, wherein each of the first TMT and the third TMT comprises a mass reporter, a mass normalizer and a cysteine reactive group that are covalently linked to each other, and each of the second TMT and the fourth TMT comprises a mass reporter, a mass normalizer and an amine reactive group that are covalently linked to each other.

13. The method of claim 12, wherein each of the first TMT and the third TMT is selected from the isobaric set of IodoTMTsixplex, or wherein each of the second TMT and the fourth TMT is selected from an isobaric set of TMT6plex, TMT10plex or TMT pro16 plex.

14. The method of claim 1, wherein the conjugate is an antibody drug conjugate (ADC).

15. The method of claim 1, wherein a multiplex of samples comprising one or more conjugates are analyzed.

16. The method of claim 1, wherein the conjugate or the ADC comprises one or more drugs conjugated to a cysteine residue of the polypeptide or the antibody, or wherein the conjugate or the ADC comprises one or more drugs conjugated to a lysine residue of the polypeptide or the antibody.

17. The method of claim 2, wherein each of the first TMT, second TMT, third TMT and fourth TMT comprises a mass reporter, a mass normalizer and an amine reactive group that are covalently linked to each other, or wherein each of the first TMT, second TMT, third TMT and fourth TMT is selected from TMT6plex, TMT10plex or TMT pro16 plex.

18. The method of claim 1, wherein the drug conjugation site in the conjugate is characterized by a mass spec bar code comprising (2n+2) reporter ions, and the conjugate is normalized by a mass spec bar code comprising n+1 reporter ions, and n is the number of samples analyzed by the method.

19. A system for conducting the method of claim 1.

* * * * *